(12) United States Patent
Gruber et al.

(10) Patent No.: US 6,617,431 B1
(45) Date of Patent: Sep. 9, 2003

(54) RECOMBINANT COLLAGEN AND DERIVED PROTEINS PRODUCED BY PLANTS, METHODS FOR OBTAINING THEM AND USES

(75) Inventors: Veronique Gruber, Chamalieres (FR); Jean-Yves Exposito, Bonnefamille (FR); Florence Ruggiero, Villeurbanne (FR); Jeanne Comte, Sainte Foy les Lyon (FR); Robert Garrone, Bron (FR); Bertrand Merot, Volvic (FR); Philippe Bournat, Clermont-Ferrand (FR)

(73) Assignee: Meristem Therapeutics S.A., Clermont-Ferrand (FR)

( * ) Notice: Subject to any disclaimer, the term of this patent is extended or adjusted under 35 U.S.C. 154(b) by 0 days.

(21) Appl. No.: 09/331,347

(22) PCT Filed: Dec. 17, 1997

(86) PCT No.: PCT/FR97/02331

§ 371 (c)(1),
(2), (4) Date: Aug. 17, 1999

(87) PCT Pub. No.: WO98/27202

PCT Pub. Date: Jun. 25, 1998

(30) Foreign Application Priority Data

Dec. 17, 1996 (FR) .............................................. 96 16224

(51) Int. Cl.$^7$ ................................................ C07K 14/00
(52) U.S. Cl. ........................................................ 530/356
(58) Field of Search ................................. 530/356, 354; 514/2, 460; 424/456, 492

(56) References Cited

PUBLICATIONS

Haralson et al. 1978; Fed. Proc. 37(6):1408.*
Okada et al. 1993; J. Biomed. Materials Res. 27:1509–1518.*
Tromp et al. 1988; Biochem. J. 253:919–922.*

* cited by examiner

Primary Examiner—Karen Cochrane Carlson
(74) Attorney, Agent, or Firm—Hoffmann & Baron, LLP; Irving N. Feit

(57) ABSTRACT

The invention concerns the use of a recombinant nucleotide sequence containing a cDNA coding for one or several mammalian collagen chains or derived proteins and elements enabling a plant cell to produce the collagen chains(s) or derived proteins, coded by said cDNA, particularly a transcription promoter and terminator identified by the transcription machinery of the plant cells, for transforming the plant cells so as to obtain from these cells, or plants obtained from them, the collagen chain(s) or derived proteins. The invention also concerns the resulting proteins and transformed plant material as well as their uses.

10 Claims, 10 Drawing Sheets

FIG. 7A ADEFG CONSTRUCT, COMPLETE PROα1 (I)

Protein Sequence

Figure 1:
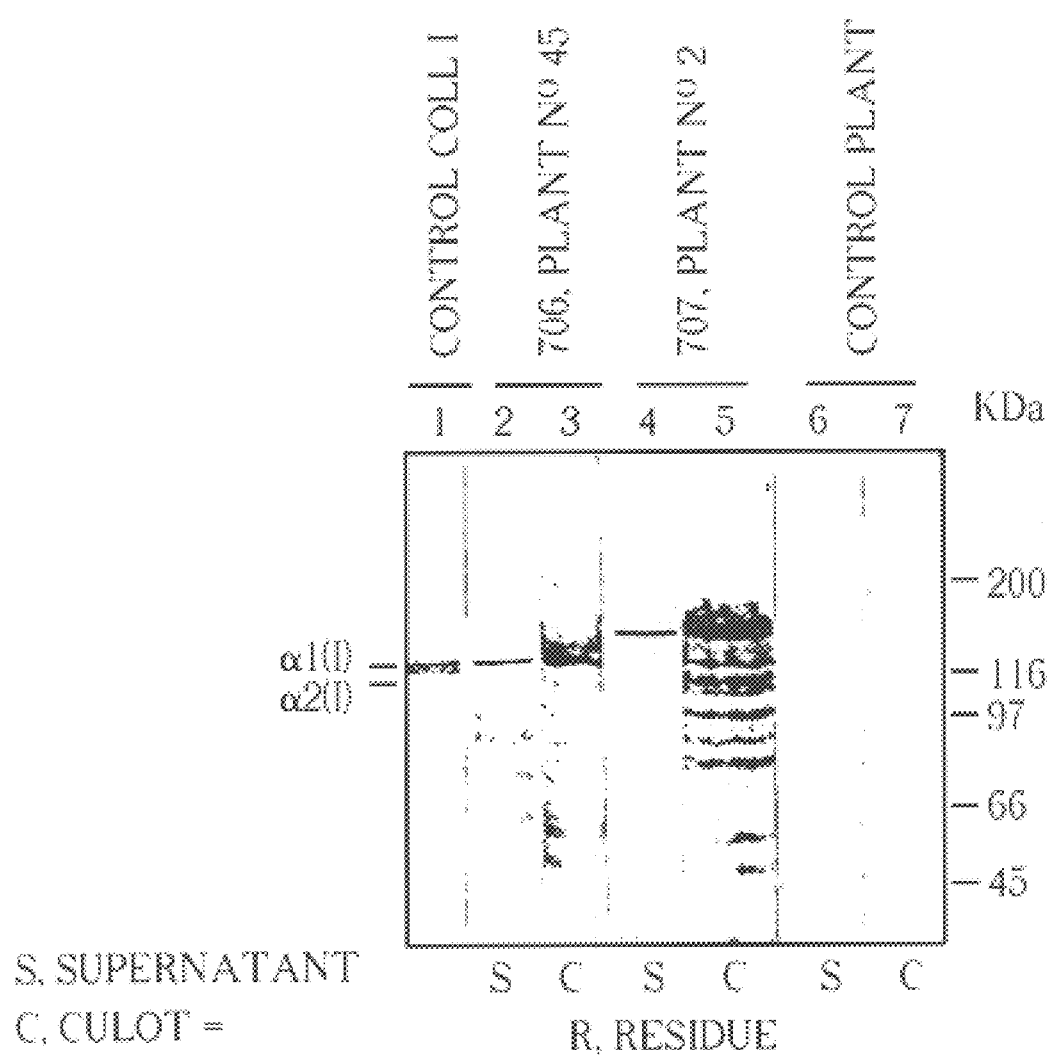

```
MFSFVDLRLLLLLAATALLTHGQEEGQVEGQDEDIPPITCVQNGLRYHDR    50
DVWKPEPCRICVCDNGKVLCDDVICDETKNCPGAEVPEGECCPVCPDGSE   100
SPTDQETTGVEGPKGDTGPRGPRGPAGPPGRDGIPGQPGLPGPPGPPGPP   150
GPPGLGGKLAPQLSYGYDEKSTGGISVPGMGPSGPRGLPGPPGAPGPQG    200
FQGPPGEPGEPGASGPMGPRGPPGPPGKNGDDGEAGKPGRPGERGPPGPQ   250
GARGLPGTAGLPGMKGHRGFSGLDGAKGDAGPAGPKGEPGSPGENGAPGQ   300
MGPRGLPGERGRPGAPGPAGARGNDGATGAAGPPGPTGPAGPPGFPGAVG   350
AKGEAGPQGPRGSEGPQGVRGEPGPPGPAGAAGPAGNPGADGQPGAKGAN   400
GAPGIAGAPGFPGARGPSGPQGPGGPPGPKGNSGEPGAPGSKGDTGAKGE   450
PGPVGVQGPPGPAGEEGKRGARGEPGPTGLPGPPGERGGPGSRGFPGADG   500
VAGPKGPAGERGSPGPAGPKGSPGEAGRPGEAGLPGAKGLTGSPGSPGPD   550
GKTGPPGPAGQDGRPGPPGPPGARGQAGVMGFPGPKGAAGEPGKAGERGV   600
PGPPGAVGPAGKDGEAGAQGPPGPAGPAGERGEQGPAGSPGFQGLPGPAG   650
PPGEAGKPGEQGVPGDLGAPGPSGARGERGFPGERGVQGPPGPAGPRGAN   700
GAPGNDGAKGDAGAPGAPGSQGAPGLQGMPGERGAAGLPGPKGDRGDAGP   750
KGADGSPGKDGVRGLTGPIGPPGPAGAPGDKGESGPSGPAGPTGARGAPG   800
DRGEPGPPGPAGFAGPPGADGQPGAKGEPGDAGAKGDAGPPGPAGPAGPP   850
GPIGNVGAPGAKGARGSAGPPGATGFPGAAGRVGPPGPSGNAGPPGPPGP   900
AGKEGGKGPRGETGPAGRPGEVGPPGPPGPAGEKGSPGADGPAGAPGTPG   950
PQGIAGQRGVVGLPGQRGERGFPGLPGPSGEPGKQGPSGASGERGPPGPM  1000
GPPGLAGPPGESGREGAPGAEGSPGRDGSPGAKGDRGETGPAGPPGAPGA  1050
PGAPGPVGPAGKSGDRGETGPAGPAGPVGPAGARGPAGPQGPRGDKGETG  1100
EQGDRGIKGHRGFSGLQGPPGPPGSPGEQGPSGASGPAGPRGPPGSAGAP  1150
GKDGLNGLPGPIGPPGPRGRTGDAGPVGPPGPPGPPGPPSAGFDFSF    1200
LPQPPQEKAHDGGRYYRADDANVVRDRDLEVDTTLKSLSQQIENIRSPEG  1250
SRKNPARTCRDLKMCHSDWKSGEYWIDPNQGCNLDAIKVFCNMETGETCV  1300
YPTQPSVAQKNWYISKNPKDKRHVWFGESMTDGFQFEYGGQGSDPADVAI  1350
QLTFLRLMSTEASQNITYHCKNSVAYMDQQTGNLKKALLLKGSNEIEIRA  1400
EGNSRFTYSVTVDGCTSHTGAWGKTVIEYKTTKTSRLPIIDVAPLDVGAP  1450
DQEFGFDVGPVCFL                                     1464
```

UNDERLINE: PEPTIDE SIGNAL OF THE PROα1 (I) CHAIN
BOLD: SUBSTITUTION OF AMINO ACIDS 158 AND 159, NF BY KL
OUTLINE: CUTTING SITES OF AMINO- AND CARBOXY-PROTEINASE

FIG. 7B1

Nucleic sequence

```
                                              AAGCTTAGAC
ATGTTCAGCTTTGTGGACCTCCGGCTCCTGCTCCTCTTAGCGGCCACCGC  50
CCTCCTGACGCACGGCCAAGAGGAAGGCCAAGTCGAGGGCCAAGACGAAG 100
ACATCCCACCAATCACCTGCGTACAGAACGGCCTCAGGTACCATGACCGA 150
GACGTGTGGAAACCCGAGCCCTGCCGGATCTGCGTCTGCGACAACGGCAA 200
GGTGTTGTGCGATGACGTGATCTGTGACGAGACCAAGAACTGCCCCGGCG 250
CCGAAGTCCCCGAGGGCGAGTGCTGTCCGTCTGCCCCGACGGCTCAGAG 300
TCACCCACCGACCAAGAAACCACCGGCGTCGAGGGACCCAAGGGAGACAC 350
TGGCCCCCGAGGCCCAAGGGGACCCGCAGGCCCCCCTGGCCGAGATGGCA 400
TCCCTGGACAGCCTGGACTTCCCGGACCCCCGGACCCCCGGACCTCCC 450
GGACCCCCTGGCCTCGGAGGAAAGCTAGCTCCCCAGCTGTCTTATGGCTA 500
TGATGAGAAATCAACCGGAGGAATTTCGTGCCTGGCCCCATGGGTCCCT 550
CTGGTCCTCGTGGTCTCCCTGGCCCCCTGGTGCACCTGGTCCCCAAGGC 600
TTCCAAGGTCCCCCTGGTGAGCCTGGCGAGCCTGGAGCTTCAGGTCCCAT 650
GGGTCCCCGAGGTCCCCCAGGTCCCCCTGGAAAGAATGGAGATGATGGGG 700
AAGCTGGAAAACCTGGTCGTCCTGGTGAGCGTGGGCCTCCTGGGCCTCAG 750
GGTGCTCGAGGATTGCCCGGAACAGCTGGCCTCCCTGGAATGAAGGGACA 800
CAGAGGTTTCAGTGGTTTGGATGGTGCCAAGGGAGATGCTGGTCCTGCTG 850
GTCCTAAGGGTGAGCCTGGCAGCCCTGGTGAAAATGGAGCTCCTGGTCAG 900
ATGGGCCCCCGTGGCCTGCCTGGTGAGAGAGGTCGCCCTGGAGCCCCTGG 950
CCCTGCTGGTGCTCGTGGAAATGATGGTGCTACTGGTGCTGCCGGGCCCC 1000
CTGGTCCCACCGGCCCCGCTGGTCCTCCTGGCTTCCCTGGTGCTGTTGGT 1050
GCTAAGGGTGAAGCTGGTCCCCAAGGGCCCCGAGGCTCTGAAGGTCCCCA 1100
GGGTGTGCGTGGTGAGCCTGGTCCCCCTGGCCCTGCTGGTGCTGCTGGCC 1150
CTGCTGGAAACCCTGGTGCTGATGGACAGCCTGGTGCTAAAGGTGCCAAT 1200
GGTGCTCCTGGTATTGCTGGTGCTCCTGGCTTCCCTGGTGCCCGAGGCCC 1250
CTCTGGACCCCAGGGCCCCGGCGGCCCTCCTGGTCCCAAGGGTAACAGCG 1300
GTGAACCTGGTGCTCCTGGCAGCAAAGGAGACACTGGTGCTAAGGGAGAG 1350
CCTGGCCCTGTTGGTGTTCAAGGACCCCCTGGCCCTGCTGGAGAGGAAGG 1400
```

FIG. 7B2

Nucleic sequence

```
AAAGCGAGGAGCTCGAGGTGAACCCGGACCCACTGGCCTGCCCGGACCCC      1450
CTGGCGAGCGTGGTGGACCTGGTAGCCGTGGTTTCCCTGGCGCAGATGGT      1500
GTTGCTGGTCCCAAGGGTCCCGCTGGTGAACGTGGTTCTCCTGGCCCCGC      1550
TGCCCCAAAGGATCTCCTGGTGAAGCTGGTCGTCCCGGTGAAGCTGGTC      1600
TGCCTGGTGCCAAGGGTCTGACTGGAAGCCCTGGCAGCCCTGGTCCTGAT      1650
GGCAAAACTGGCCCCCCTGGTCCCGCCGGTCAAGATGGTCGCCCCGGACC      1700
CCCAGGCCGACCTGGTGCCCGTGGTCAGGCTGGTGTGATGGGATTCCCTG      1750
GACCTAAAGGTGCTGCTGGAGAGCCCGGCAAGGCTGGAGAGCGAGGTGTT      1800
CCCGGACCCCTGGCGCTGTCGGTCCTGCTGGCAAAGATGGAGAGGCTGG      1850
AGCTCAGGGACCCCTGGCCCTGCTGGTCCCGCTGGCGAGAGAGGTGAAC      1900
AAGGCCCTGCTGGCTCCCCGGATTCCAGGGTCTCCCTGGTCCTGCTGGT      1950
CCTCCAGGTGAAGCAGGCAAACCTGGTGAACAGGGTGTTCCTGGAGACCT      2000
TGGCGCCCCTGGCCCCTCTGGAGCAAGAGGCGAGAGAGGTTTCCCTGGCG      2050
AGCGTGGTGTGCAAGGTCCCCCTGGTCCTGCTGGACCCCGAGGGGCCAAC      2100
GGTGCTCCCGGCAACGATGGTGCTAAGGGTGATGCTGGTGCCCCTGGAGC      2150
TCCCGGTAGCCAGGGCGCCCCTGGCCTTCAGGGAATGCCTGGTAACGTG      2200
GTGCAGCTGGTCTTCCAGGGCCTAAGGGTGACAGAGGTGATGCTGGTCCC      2250
AAAGGTGCTGATGGCTCTCCTGGCAAAGATGGCGTCCGTGGTCTGACCGG      2300
CCCCATTGGTCCTCCTGGCCCTGCTGGTGCCCCTGGTGACAAGGGTGAAA      2350
GTGGTCCCAGCGGCCCTGCTGGTCCCACTGGAGCTCGTGGTGCCCCCGGA      2400
GACCGTGGTGAGCCTGGTCCCCCGGCCCTGCTGGCTTTGCTGGCCCCCC      2450
TGGTGCTGACGGCCAACCTGGTGCTAAAGGCGAACCTGGTGATGCTGGTG      2500
CCAAGGCGATGCTGGTCCCCCTGGGCCTGCCGGACCCGCTGGACCCCCT      2550
GGCCCCATTGGTAATGTTGGTGCTCCTGGAGCCAAAGGTGCTCGCGGCAG      2600
CGCTGGTCCCCCTGGTGCTACTGGTTTCCCTGGTGCTGCTGGCCGAGTCG      2650
GTCCTCCTGGCCCCTCTGGAAATGCTGGACCCCTGGCCCTCCTGGTCCT      2700
GCTGGCAAAGAAGGCGGCAAAGGTCCCCGTGGTGAGACTGGCCCTGCTGG      2750
ACGTCCTGGTGAAGTTGGTCCCCCTGGTCCCCCTGGCCCTGCTGGCGAGA      2800
AGGATCCCCTGGTGCTGATGGTCCTGCTGGTGCTCCTGGTACTCCCGGG      2850
CCTCAAGGTATTGCTGGACAGCGTGGTGTGGTCGGCCTGCCTGGTCAGAG      2900
AGGAGAGAGAGGCTTCCCTGGTCTTCCTGGCCCCTCTGGTGAACCTGGCA      2950
AACAAGGTCCCTCTGGAGCAAGTGGTGAACGTGGTCCCCCGGTCCCATG      3000
GGCCCCCTGGATTGGCTGGACCCCTGGTGAATCTGGACGTGAGGGGGC      3050
TCCTGGTGCCGAAGGTTCCCCTGGACGAGACGGTTCTCCTGGCGCCAAGG      3100
GTGACCGTGGTGAGACCGGCCCCGCTGGACCCCCTGGTGCTCCTGGTGCT      3150
CCTGGTGCCCCTGGCCCCGTTGGCCCTGCTGGCAAGAGTGGTGATCGTGG      3200
```

FIG. 7B3

Nucleic sequence

```
TGAGACTGGTCCTGCTGGTCCCGCCGGTCCCGTCGGCCCCGCTGGCGCCC    3250
GTGGCCCCGCCGGACCCCAAGGCCCCCGTGGTGACAAGGGTGAGACAGGC    3300
GAACAGGGCGACAGAGGCATAAAGGGTCACCGTGGCTTCTCTGGCCTCCA    3350
GGGTCCCCCTGGCCCTCCTGGCTCTCCTGGTAACAAGGTCCCTCTGGAG    3400
CCTCTGGTCCTGCTGGTCCCCGAGGTCCCCCTGGCTCTGCTGGTGCTCCT    3450
GGCAAAGATGGACTCAACGGTCTCCCTGGCCCCATTGGGCCCCTGGTCC    3500
TCGCGGTCGCACTGGTGATGCTGGTCCTGTTGGTCCCCCGGCCCTCCTG    3550
GACCTCCTGGTCCCCCTGGTCCTCCCAGCGCTGGTTTCGACTTCAGCTTC    3600
CTGCCCCAGCCACCTCAAGAGAAGGCTCACGATGGTGGCCGCTACTACCG    3650
GGCTGATGATGCCAATGTGGTTCGTGACCGTGACCTCGAGGTGGACACCA    3700
CCCTCAAGAGCCTGAGCCAGCAGATCGAGAACATCCGGAGCCCAGAGGGA    3750
AGCCGCAAGAACCCCGCCCGCACCTGCCGTGACCTCAAGATGTGCCACTC    3800
TGACTGGAAGAGTGGAGAGTACTGGATTGACCCCAACCAAGGCTGCAACC    3850
TGGATGCCATCAAAGTCTTCTGCAACATGGAGACTGGTGAGACCTGCGTG    3900
TACCCCACTCAGCCCAGTGTGGCCCAGAAGAACTGGTACATCAGCAAGAA    3950
CCCCAAGGACAAGAGGCATGTCTGGTTCGGCGAGAGCATGACCGATGGAT    4000
TCCAGTTCGAGTATGGCGGCCAGGGCTCCGACCCTGCCGATGTGGCCATC    4050
CAGCTGACCTTCCTGCGCCTGATGTCCACCGAGGCCTCCCAGAACATCAC    4100
CTACCACTGCAAGAACAGCGTGGCCTACATGGACCAGCAGACTGGCAACC    4150
TCAAGAAGGCCCTGCTCCTCAAGGGCTCCAACGAGATCGAGATCCGCGCC    4200
GAGGGCAACAGCCGCTTCACCTACAGCGTCACTGTCGATGGCTGCACGAG    4250
TCACACCGGAGCCTGGGGCAAGACAGTGATTGAATACAAAACCACCAAGA    4300
CCTCCCGCCTGCCCATCATCGATGTGGCCCCCTTGGACGTTGGTGCCCCA    4350
GACCAGGAATTCGGCTTCGACGTTGGCCCTGTCTGCTTCCTGTAA        4395
GCTT
```

UNDERLINE: HindIII, AAGCTT CLONING SITES, AT 5' AND 3' OF THE SEQUENCE
BOLD: PEPTIDE SIGNAL OF THE PROα1 (I) CHAIN, TAA STOP CODON,
    SUBSTITUTED NUCLEOTIDES, 474, 475 AND 477 (CTT BY GCA)
OUTLINE: CHIEF RESTRICTION SITES

RECOMBINANT COLLAGEN AND DERIVED PROTEINS PRODUCED BY PLANTS, METHODS FOR OBTAINING THEM AND USES

This application is a 371 of PCT/FR97/02331, filed Dec. 17, 1977, and claims priority to French application 96/16224, Dec. 17, 1996.

The present invention relates to the production by plants of recombinant collagens, in particular Type 1 homocatenary collagen [αI (I)$_3$] and other polypeptide derivatives, and their uses.

Patent WO 9603051 is known to the prior art which concerns the production of collagen in the milk of transgenic animals.

Collagen is an extracellular fibrous animal protein, widely found in animal tissues (recently detected in some mushrooms also). Some organs contain high quantities thereof: skin (at the dermis), tendons, bones. It is in fact a polymer whose remarkable properties are due both to the triple coil characteristics of some domains of its molecule and to the regularity of its supramolecular assemblies. It is involved in the organisation of the extracellular matrix grouping together twenty or so different molecules, called "types" that are identified by Roman figures (currently from I to XIX). The characteristic triple coil domain is formed by the coiling of three peptides, or α chains, arranged in a left wound coil and derived from a single conformation, the α coil of collagen. This specific conformation results from the repetition of a triplet of amino acids, Gly-X-Y in which X is frequently represented by proline and Y by hydroxyproline. These amino acids give stability to this type of coil. In a collagen molecule, the three α chains (identified by an index in Arabic figures) arranged in a right wound supercoil may be identical (α1 (or alpha1)), of two types (α1 and α2) or all different (α1, α2, α3). Collagen molecules therefore comprise helical domains (or collagen domains) and non-helical domains. They associate to form homo or heterotype polymers. Thus the collagen fibrils which form the essential part of the dermis are mostly made up of type I collagen [α1 (I)$_2$ α2 (I)] associated with collagens of type III [α1 (III)$_3$], of type V [α1 (V)$_2$ α2 (V)] and covered by collagens of type XII (α1 (XII)$_3$) and/or XIV [α1 (XIV)$_3$]. Variants may exist: for example a homocatenary collagen of type 1 [α1 (I)$_3$] is found in embryo tissues. During the biosynthesis of collagen some prolyl and lysil residues are hydroxylated, an addition of galactose possibly supplemented with a glucose may be made on some hydroxyl residues and conventional N and O glycosylations may occur on the non-helical domains. The recognition of the three chains forming a molecule and the start of their assembly are under the control of the C-terminal end (C-propeptide). Type I collagen undergoes enzymatic cutting of its non-helical ends subsequent to the previously cleaved peptide signal, the N and C-terminal propeptides are excised during maturation of the collagen leaving short, non-helical terminal extensions (telopeptides). It is these cleaved molecules which group together in arranged polymers (collagen fibrils) and which during the course of time undergo cross-linking via the hydroxylysyl residues of a molecule and the telopeptides of an adjacent molecule. The mechanical and biological properties of collagen have long been put to use; when cross-linked in irreversible manner (tanning process) it gives leather; when denatured by heating it gives rise to gelatin and glues. But it was only in the last decade that collagen truly provided biomaterials for pharmaceutical use (haemostatic compresses, sponges, dressings in particular healing dressings), medical use (prostheses such as cardiac valves, tendons and ligaments, skin substitutes, filling agents), odontological use (gum implants) and cosmetic use (additive, microcontainer for perfumed substances).

Later improved knowledge of this protein and of purification methods have led to the preparation of bovine and human placenta collagens in pre-defined form: gel, sponge, powder, suture and microsphere for example. Engineering of the extracellular matrices is also applied to the production of organoids containing transfected cells for gene therapy applications for example. The collagen mainly used is type I (generally associated with type III) for reasons of abundant availability and low purification costs, and the main sources have been bovine (skins unfit for tanning) ovine (hide and intestine) and human (placenta). This last source was exclusively reserved for pharmaceutical or medical applications.

Although the very useful mechanical and biological properties of collagen are clearly recognised, the use of this protein is questioned owing to the possible risks of contamination by non-conventional infectious agents. While the risks raised by bacterial or viral contamination can be fully controlled, this is not the case for those associated with agents of prion type. These infectious agents which appear to have a protein nature take part in the development of degenerative animal encephalopathy (sheep trembling disease, bovine spongiform encephalopathy) and human encephalopathy (Creutzfeld-Jacob disease, Gerstmann-Straussler syndrome, kuru). The long time of onset for their possible expression means that formal controls are difficult to conduct. These risks have already virtually frozen all marketing of human collagen, and the regulations laid down for the animal collagens concerned complicate purification processes and increase their cost.

Faced with these difficulties and radical deterioration in the image of mammalian collagen, one solution is the production of recombinant collagen which could be easily purified in a system that is not likely to give rise to pathogenic risks for man and whose industrial cost is not prohibitive. The inventors have therefore discovered and developed a production of collagen in plant species. For example we have been able to produce a human collagen of type I. Its molecule comprises a long, unbroken triple coil and is sparingly immunogenic after purification. The inventors have for example caused expression of the α1 (I) chain in order to obtain α1 (I)$_3$ homocatenary molecules similar to those which exist in some tissues, especially embryo tissues.

Animal cells are, in theory, more adapted to the expression of mammalian genes. Their use however raises problems of protein maturation. The enzymatic equipment which carries out post-translational maturation differs from one tissue, organ or species to another. For example, it has been reported that post-translational maturation of a plasma protein may differ according to whether it is obtained from human blood or produced by a recombinant cell such as Chinese hamster ovary cells or in the milk of a transgenic animal. Moreover, the low levels of expression obtained with mammalian cells involve large volumes of in vitro cultures at high cost. With the production of recombinant proteins in the milk of transgenic animals (mice, ewes and cows) it is possible to reduce production costs and to overcome problems of expression level. However problems remain in respect of ethics and viral and subviral contamination (prions).

For these reasons, the transgenesis of mammalian genes in a plant cell could offer a pathway for the production in great quantities of new recombinant proteins at reduced production cost and with no risk of viral or subviral contamination. In 1983, several laboratories discovered that it is possible to transfer a heterologous gene into the genome of a plant cell, and to regenerate transgenic plants from these genetically modified cells. All the plants cells then have the genetically modified character transmitted to their descent by sexual fertilisation.

Through this work several teams have focused their attention on the production of recombinant mammalian proteins in plant cells or in transgenic plants (Barta et al., 1986; Marx et al., 1982). One of the first truly significant results in this area was the production of antibodies in transgenic tobacco plants. To express a heterologous protein in the grain, where plants stock proteins, Vandekerckhove's team fused the sequence coding for leu-enkephaline to the gene coding for the 2S albumin of *Arabidopsis thaliana*. With this construct, transgenic Arabidopsis plants were produced which express leu-enkephaline specifically in the grains at expression levels in the region of 0.1% of total proteins. In 1990, the human albumin serum gene was transferred to tobacco and potato cells. Irrespective of the origin of the peptide signals (human or plant), levels of human albumin serum in the region of 0.02% of total proteins were obtained in particular in potato plant leaves. Other recombinant mammalian proteins have also been produced in plants: the surface antigen of hepatitis B, interferons, an anti-*Streptococcus mutans* mouse antibody, a caries agent, fragments of anti-cancer cell scFV antibodies, an anti-herpes antibody, cholera toxin and the human epidermal growth factor (E.G.F.). All this research has led to showing that the production of recombinant mammalian proteins in plant cells is possible, and that the mechanisms of protein synthesis from DNA sequences are similar in animal cells and plant cells. Numerous differences exist nonetheless between plant and animal cells, in particular in respect of the maturation of polymannosodic glycanns into complex glycanns, or at the cleavage sites of the peptide signals which means that it is not possible to guarantee that active or sufficiently active mammalian proteins can be obtained through plant cell transformation.

The inventors have discovered that the use of plant cells, transformed by an appropriate recombinant nucleotide sequence, can lead to obtaining collagen, in particular recombinant type I homotrimeric collagen $[\alpha 1 \, (I)]_3$.

Another purpose of the invention is to provide the tools to implement such process, in particular new recombinant nucleotide sequences, cells of genetically transformed plants, plants or parts of plants (in particular leaves, stalks, fruits, seeds or grains, roots) that are genetically transformed, and fragments of these genetically transformed plants or parts of plants.

A further purpose of the invention is to provide new collagens produced by plants, in particular type I homotrimeric collagen $[\alpha 1 \, (I)]_3$.

A further purpose of the invention is to provide new protein compositions able to be used for the implementation or supply of pharmaceutical, medical, odontological, cosmetic, biochemical or industrial compositions.

DETAILED DESCRIPTION OF THE INVENTION

The invention concerns:
the use of a recombinant nucleotide sequence containing firstly a cDNA coding for one or more chains of mammalian collagen, in particular the one whose cDNA is that of the $\alpha 1$ collagen chain, or the derived proteins (by derived protein is meant any protein having at least 70% homology to the reference protein, in particular at least 80%, for example between 85 and 100% homology), and secondly the elements enabling a plant cell to produce the chain or chains of collagen or the derived proteins encoded by said cDNA, in particular a promoter and a transcription terminator recognised by the transcriptional machinery of the plant cells, for the transformation of plant cells with a view to obtaining from these cells or plants obtained from the latter, the chain or chains of collagen or the derived proteins, possibly in triple coil form, a recombinant nucleotide sequence characterised in that it contains firstly the sequence coding for one or more chains of mammalian collagen, in particular that of the $\alpha 1$ collagen chain, or the derived proteins, and secondly the elements enabling a plant cell to produce the chain or chains of collagen or the derived proteins encoded by said sequence, possibly in triple coil form, in particular a promoter and a transcription terminator recognised by the transcriptional machinery of the plant cells, a vector, in particular a plasmid, containing a nucleotide sequence of the invention inserted at a site that is non-essential for its replication, a host cell, in particular any bacterium such as *Agrobacterium tumefaciens*, transformed by a vector of the invention, a method of obtaining one or more collagen chains or derived polypeptides, optionally in triple coil form, characterised in that it entails:
  the transformation of plant cells, in particular using a host cell of the invention, itself transformed by a vector of the invention, such as to incorporate into the genome of these cells a recombinant sequence of the invention,
  optionally obtaining transformied plants from the above-mentioned transformed cells,
  collecting the recombinant chain or chains of collagen or derived polypeptides produced in said above-mentioned transformed plant cells, in particular by extraction, optionally followed by purification, a plant, plant extract or plant part, in particular genetically transformed leaves and/or fruits and/or seeds and/or plant cells, characterised in that it contains one (or more) recombinant nucleotide sequencers) of the invention incorporated into their genome in stable manner, these plants being chosen in particular from colza, tobacco, maize, pea, tomato, carrot, wheat, barley, potato, soybean, sunflower, lettuce, rice, alfalfa and beetroot.

one or more collagen chains or derived proteins characterised in that it is obtained in accordance with the method of the invention, a collagen (in particular a collagen of type 1, II, III, IV or V) or a derived protein, characterised in that it is obtained in accordance with the method of the invention, a product, in particular gelatin, characterised in that it is obtained from the collagen chains, collagen or their derived proteins of the invention, a plant, plant extract or plant part, in particular genetically transformed leaves and/or fruits and/or seeds and/or plant cells, characterised in that they contain collagen chains, collagen or the derived proteins according to the invention, these plants being chosen in particular from colza, tobacco, maize, pea, tomato, carrot, wheat, barley, potato, soybean, sunflower, lettuce, rice, alfalfa and beetroot.

the use of plants, plant extracts or plant parts of the invention, and/or proteins (collagen chains, collagen or derived proteins) of the invention to obtain pharmaceutical, medical, odontological, cosmetic or biotechnological compositions, a Biomaterial and a pharmaceutical, medical, odontological, cosmetic or biotechnological composition, characterised in that it comprises plants, plant extracts, plant parts or collagen chains, collagen or the derived protein of the invention, One pharmaceutical composition of the invention particularly comprises any composition of the invention forming (or entering into the production of) a composition enabling the prevention or treatment of any pathology connected with collagen malfunctioning, or a compress for wound healing, a haemostat dressing, bedsore dressing, haemostat powder; or a dressing for burns.

One medical composition of the invention comprises in particular any composition of the invention forming (or entering into the production of) a corneal coating device, a coagulant film for organ resection (liver in particular), a filling material for the prevention of adhesions and fistulae, a composition for the fabrication of vascular and cardiac prostheses(valves), a guide-duct for nerve regeneration, bone and intra-body filling material, a container-releaser of active substances (hormones, growth factors, antibiotics, anticancer drugs, anti-inflammatories for example), a compression device (for example to reduce urinary incontinence), a skin substitute, surgical suture thread, an injectable material for cosmetic surgery (filling of skin depressions or face remodelling for example).

One odontological composition of the invention comprises in particular any composition of the invention forming (or entering into the production of) a gum dressing or a filling material.

One cosmetic composition of the invention comprises in particular any composition of the invention forming (or entering into the produciton of) a preparation additive (creams, ointments, make-up, liniments).

One medical composition of the invention comprises in particular any composition of the invention forming (or entering into the production of) a system for: covering cell culture dishes and bottles.

The invention also relates to a product, in particular gelatin, characterised in that it is obtained from collagen chains, collagen or their derived proteins according to the invention.

Gelatin is normally prepared from collagen by heating animal tissues (in particular skin and bones) in water and then drying (Parkany M, 1984). This preparation destroys the secondary structure of collagen and therefore leads to major changes in the product's solubility and mechanical properties. Gelatin is the major constituent of glue. In cold water, it swells and is insoluble. In warm water it dissolves to give a very viscous solution which gels after cooling when the gelatin content is more than 1%. To prepare surgical prostheses, solutions containing 10 to 35% gelatin are used.

Gelatin's property of being soluble in warm water makes it useful for numerous food and industrial applications. It is often prepared in powder from or in thin sheets. Depending upon the desired mechanical properties, glycerol, sorbitol or cross-linking agents may for example be added during the preparation of gelatin slabs.

Gelatin is also used in the bio-medical sphere, for sponges for example.

Advantageously, the recombinant nucleotide sequences of the invention contain one (or more) sequence(s) coding for a peptide responsible for addressing recombinant polypeptides to a determined compartment of the plant cell, in particular into the endoplasmic reticulum or the vacuoles, or even outside the cell in the pectocellulose wall, or in the extracellular space also called the apoplasm.

Among the transcription terminators able to be used for the transformation of plant cells under the present invention, mention may be made of the polyA 35S terminator of the Cauliflower Mosaic Virus (CaMV), or the polyA Nos terminator which corresponds to the 3' region non-coding for the nopaline synthase gene of the Ti plasmid of *Agrobacterium tumefaciens*, nopaline strain.

In this respect, the object of the invention is any recombinant nucleotide sequence such as described above containing, upstream from said cDNA or its derived sequence, the polyA 35S terminator of CaMV or the polyA NOS terminator of *Agrobacterium tumefaciens*.

Among the transcription promoters able to be used for the transformation of plant cells under the present invention, the following may be cited:

the 35S (P35S) promoter, or advantageously the double constitutive 35S promoter (Pd35S) of CaMV, these promoters allowing expression of the recombinant polypeptides of the invention in the entire plant obtained from cells transformed according to the invention, and are described in the article by Kay et al., 1987, the PCRU promoter of the radish cruciferin gene allowing the expression of the recombinant polypeptides of the invention solely in the seeds (or grains) of the plant obtained from the cells transformed according to the invention, and described in the article by Depigny-This et al., 1992?

the PGEA1 and PGEA6 promoters corresponding to the 5' region non-coding or the genes of the reserve protein of grains, GEA1 and GEA6 respectively, of *Arabidopsis thaliana* (Gaubier et al., 1993) and allowing specific expression in the rains, the PSP super-promoter chimeric promoter (Ni M. et al., 1995), formed by the fusion of triple repetition of a transcriptional activator element of the promoter for the octopine synthase gene of *Agrobacterium tumefaciens*, of a transcriptional activator element of the promoter for the mannopine synthase gene, and of the mannopine synthase promoter of *Agrobacterium tumefaciens*, the actin promoter of rice followed by the actin intron of rice (APR-AIR) contained in the pActI-F4 plasmid described by McElroy et al. (1991), the HMGW (High Molecular Weight Glutenine) promoter of barley (Anderson O. D. et al., 1989), the promoter of the $\gamma$zein gene of maize (P$\gamma$zein) contained in the p$\gamma$63 plasmid described by Reina et al., (1990), and allowing expression in maize seed albumen.

In this respect, the object of the invention is any recombinant nucleotide sequence such as described above, containing upstream from said cDNA or its derived sequence the double 35S constitutive promoter (Pd35S) of CaMV, or the PCRU promoter of the radish cruciferin gene, or the PGEA1 or pGEA6 promoters of *Arabidopsis thaliana*, or the PSP super-promoter of *Agrobacterium tumefaciens*, or the APR-AIR promoter of rice, the HMGW promoter of barley or the pyzein promoter of maize.

The sequences coding for an addressing peptide used for the present invention may be of plant, human or animal origin.

Among the sequences coding for an addressing peptide of plant origin, the following may be cited:

the nucleotide sequence of 69 nucleotides (given in the following examples) coding for the prepeptide (peptide signal) of 23 amino acids of sporamine A in sweet potato, this peptide signal allowing entry of the recombinant polypeptides of the invention into the secretion system of the plant cells transformed according to the invention (namely, chiefly in the endoplasmic reticulum).

the nucleotide sequence of 42 nucleotides (given in the following examples) coding for the vacuole addressing N-terminal propeptide of 14 amino acids of sweet potato sporamine A, allowing the accumulation of the recombinant polypeptides of the invention in the vacuoles of the plant cells transformed according to the invention, the nucleotide sequence of 111 nucleotides (given in the following examples) coding for the prepropeptide of 37 amino acids of sporamine A made up of, from the N-terminal part towards the C-terminal part, the 23 amino acids of the above-mentioned peptide signal, followed by the 14 amino acids of the above-mentioned propeptide, this prepropeptide permitting entry of the recombinant polypeptides of the invention into the secretion system and their accumulation in the vacuoles of the plant cells transformed according to the invention, the three above-mentioned sequences being described in the articles by Murakami et al., 1986 and Matsuoka et al., 1991, the carboxyterminal propeptide of barley lectin described in particular in the articles by Schroeder et al., 1993 and Bednarek et al., 1991, and the PRS (Pathogenesis Related Protein, Cornelissen et al. 1986) permitting secretion.

Mention may also be made, among the sequences coding for an addressing peptide, of that coding for the KDEL (SEQ. ID. NO.: 1), SEKDEL (SEQ. ID. NO.: 2), and HDEL (SEQ. ID. NO.: 3) peptides and allowing addressing in the endoplasmic reticulum.

A further object of the invention is any recombinant nucleotide sequence such as described above, containing a sequence coding for all or part of a vacuole-addressing peptide, in particular that of sporamine A in sweet potato, this sequence coding for a vacuole-addressing peptide being situated, in said recombinant nucleotide sequence, between the sequence coding for a peptide signal and that coding for said cDNA or its derived sequence, such that the first N-terminal amino acid of the vacuole-addressing peptide is bound to the last C-terminal amino acid of the peptide signal, and that the last C-terminal amino acid of said addressing peptide is bound to the first N-terminal amino acid of the polypeptide encoded by said cDNA or its derived sequence, in the protein encoded by said recombinant nucleotide sequence.

Yet a further object of the invention is any recombinant nucleotide sequence such as described above, containing a sequence coding for all or part of a vacuole-addressing peptide, in particular that of barley lectin, this sequence coding for a vacuole-addressing peptide being situated, in said recombinant nucleotide sequence, downstream from the sequence coding for said cDNA or its derived sequence, such that the first N-terminal amino acid of the vacuole-addressing peptide is bound to the last C-terminal amino acid of the polypeptide encoded by said cDNA or its derived sequence, in the protein encoded by said recombinant nucleotide sequence.

DETAILED DESCRIPTION OF THE FIGURES

FIG. 1:

Immunotransfer showing an example of positive results derived from the screening of plants transformed by constructs pBIOC706 (denoted 706, plant no. 45, lanes 2,3) and pBIOC707 (denoted 707, plant no. 2, lanes 4,5). These results are to be compared with those obtained with the non-transformed control plants (lanes 6, 7). Lane 1 shows the electrophoretic migration of the control collagen I: the band corresponding to $\alpha 2$ (I) migrates at the 116 KDa band of standard molecular weights, the $\alpha 1$ (I) band migrates slightly overhead. Lanes 2, 4, 6 correspond to the extraction supernatants in an acid medium, lanes 3, 5 and 7 correspond to the residues. Construct pBIOC706 generates a major band recognised by the anti-collagen I antibody, migrating exactly at the level of the control $\alpha 1$ (I) band (lane 1): construct pBIOC707 generates a major band migrating at 140 KDa. It appears however that acid medium extraction is incomplete since the same bands are found in the corresponding extraction residues (lane 3 for pBIOC706, lane 5 for pBIOC707). The lanes corresponding to the control plant (lanes 6 and 7) are negative.

FIG. 2:

Immunotransfer showing some examples of positive plants transformed by constructs pBIOC706 (plant no. 40: lanes 2, 3 and no. 45: lanes 4, 5) and pBIOC707 (plant no. 1: lanes 6, 7; plant no. 2: lanes 8,9; plant no. 14: lanes 10, 11) extracted in a neutral medium. Lane 1 shows the electrophoretic migration of the control collagen I: the band corresponding to $\alpha 2$ (I) migrates at the 116 KDa band of standard molecular weights, band $\alpha 1$ (I) migrates slightly above. Lanes 2, 4, 6 8 and 10 correspond to the extraction supernatants in a neutral medium, lanes 3, 5, 7, 9 and 11 correspond to the residues. Plants 40 and 45 (construct pBIOC706) generate two major bands recognised by the anti-collagen I antibody, migrating respectively at the $\alpha 1$ (I) control band (lane 1) and at 140 KDa. Plants 1, 2 and 14 (construct pBIOC707) generate 2 major bands migrating respectively at 140 KDa and 160 KDa. Extraction in a neutral medium appears to be complete since no band is found in the corresponding extraction residues (lanes 3 and 5 for pBIOC706, lanes 7, 9 and 11 for pBIOC707). The lanes corresponding to the control plant (not shown) are negative. All the positive plants display the same electrophoretic tracing.

FIGS. 3A–3C

Immunotransfer showing changes in the electrophoretic tracings of positive plants transformed by constructs pBIOC707 (panel A and B) and pBIOC706 (panel C) in the presence (+) or absence (−) of a reducing agent (DTT). Lanes 1 and 8 show the electrophoretic tracing of the collagen I control. Panel A: plant no. 2 extracted in an acid medium. The single band after reduction (lane 2) observed after extraction in an acid medium shows slightly faster migration in the absence of a reducing agent (lane 3). This result suggests that the band observed corresponds to the $\alpha 1$ (I) chain comprising the N-propeptide (presence of intrachain disulfide bonds. Panel B: plant no. 2 (lanes 4 and 5) and plant no. 1 (lanes 6 and 7) extracted in a neutral medium. In the absence of a reducing agent (lanes 5 and 7) the upper band, migrating at 160 KDa in the presence of a reducing agent (lanes 4 and 6) is found at the $\gamma$ bands (3 associated $\alpha$ chains). The band migrating at 140 KDa in the presence of a reducing agent, migrates slightly faster in the absence of a reducer as seen in panel A. Panel C: plant no. 40 (lanes 9 and 10) and plant no. 45 (lanes 11 and 12) extracted in a neutral medium. Here again, only the migration of the upper band undergoes change in the absence of a reducing agent and is found as a major band, as seen for panel B, at the level of bands γ. These results indicate that the upper band for each of the constructs pBIOC706 and pBIOC707 comprises the C-propeptide. Therefore, the interchain disulfide bonds made between the C-propeptides of the native molecule were able to be made in the plant. Bonding of the C-propeptides is known to allow correct arrangement of the 3 chains and thereby initiate the formation of the triple coil. The lower bands (140 KDa for construct pBIOC707 and 120 KDa for construct pBIOC706) would therefore appear to result from the cleavage of the C-propeptide domain of the recombinant α1 (I) chain. This cleavage is an important stage in the maturation of native collagen since it is necessary for polymerisation into collagen fibre.

Figure 4:
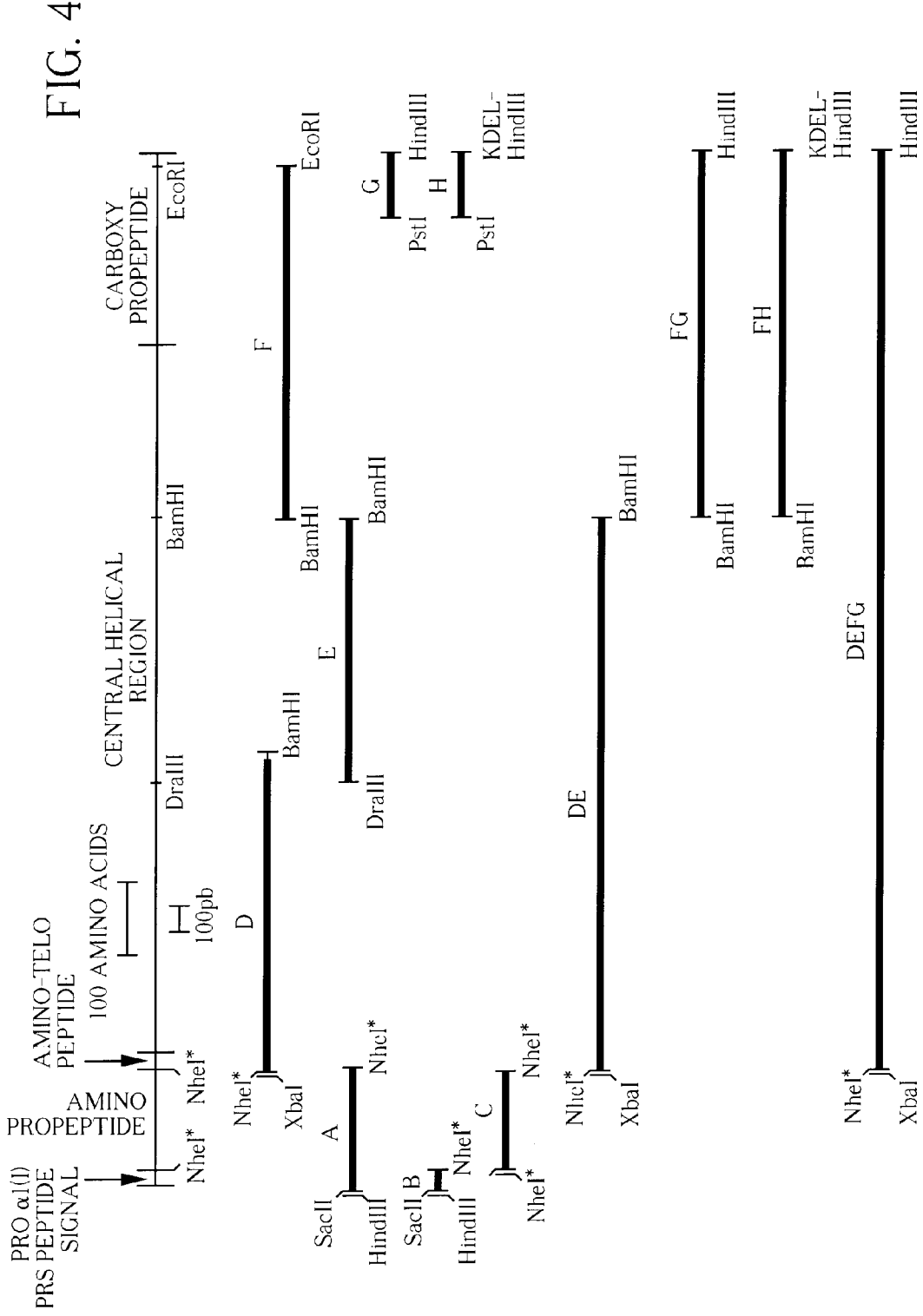
Figure 5:
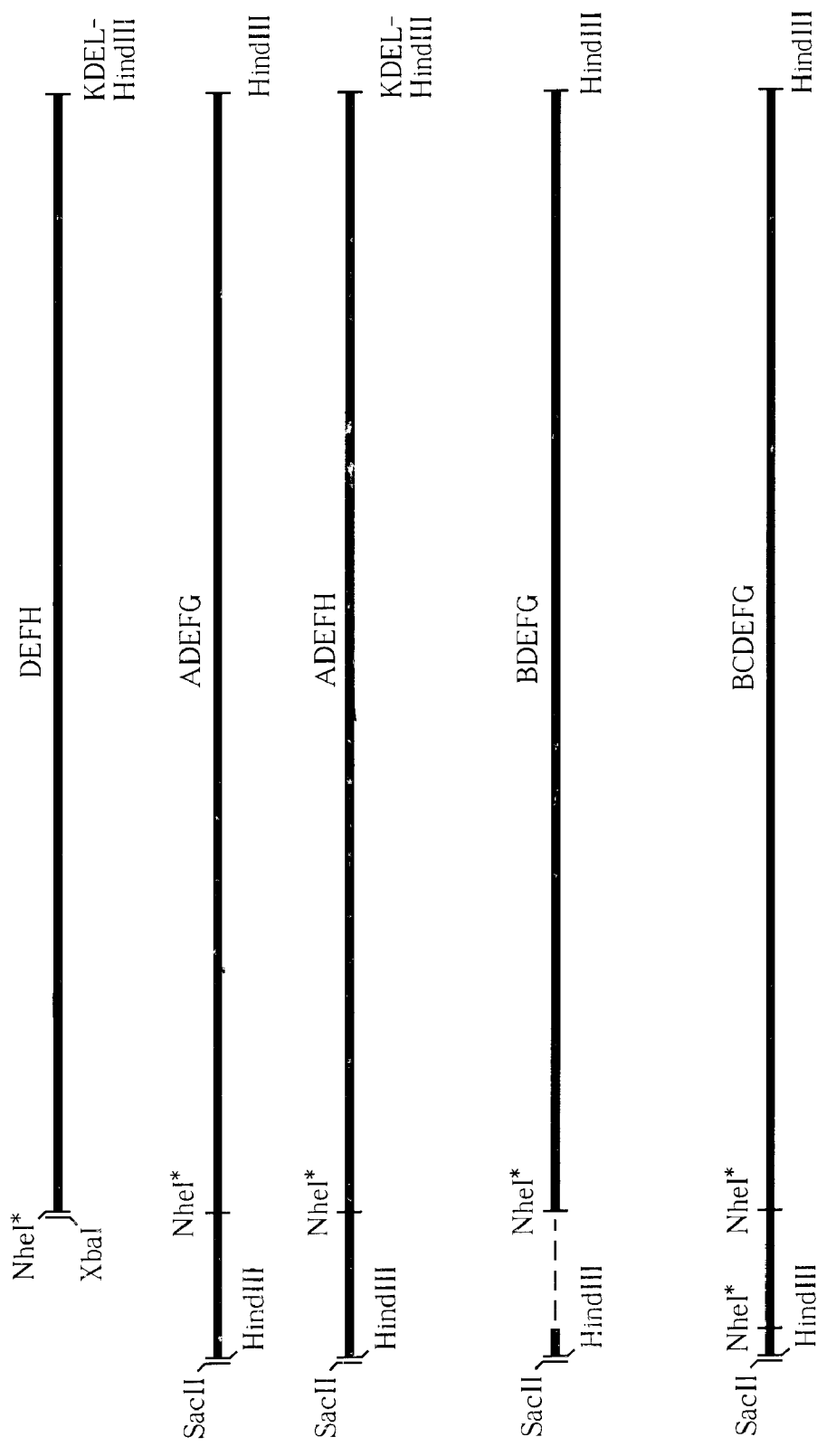

FIGS. 4 and 5: show the fragments used by the pBIOC21-collagen constructs.

Figure 6A:
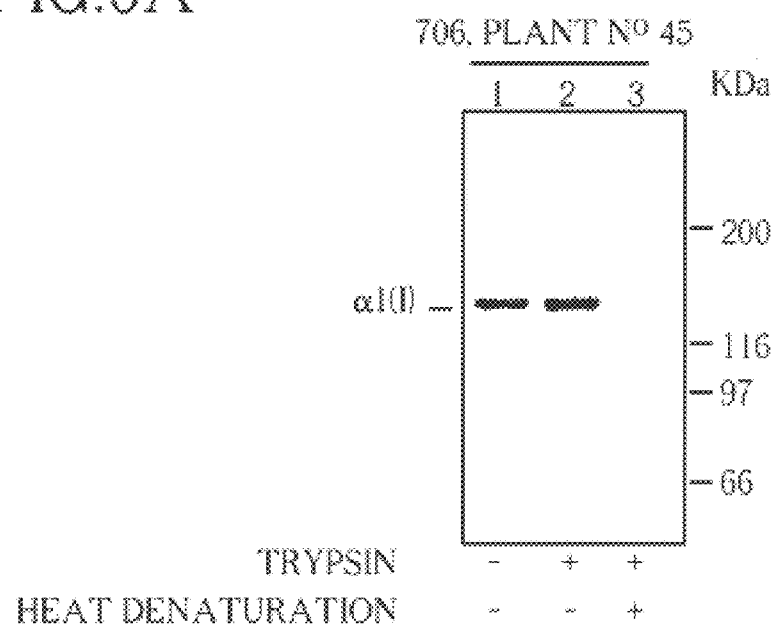
Figure 6B:
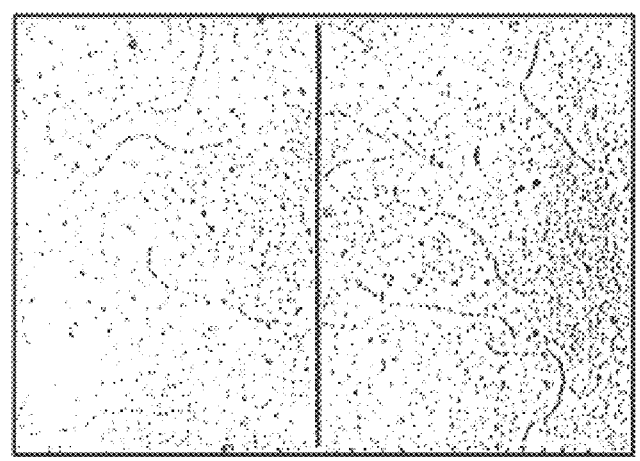

FIGS. 6A and 6B

Part A: Trypsin digestion of collagen extracted from plants transformed with construct pBIOC76(plant 45) analysed by electrophoresis on 6% acrylamide gel. Lane 1: non-digested collagen. Lane 2: collagen digested by trypsin at 25° C., the band corresponding to collagen is still present denoting the triple coil structure of the extracted collagen. Lane 3: collagen denatured by heat (50° C., 20 minutes) then digested by trypsin, the band corresponding to the collagen disappears denoting the efficiency of trypsin when collagen is denatured.

Part B: Micrograph of a replica obtained after shade rotation of the collagen purified from plant 45. The collagen molecules are seen in rod form 280 to 300 nm long and 1.4 nm in diameter, characteristic of the triple coil folding of the entire central domain of collagen I. Magnification: ×75 000.

FIGS. 7A, 7B1, 7B2, and 7B3: ADEFG construct, complete proα1 (I): protein (SEQ. ID. NO.: 21) and nucleic (SEQ. ID. NO.: 22) sequence.

PREPARATION I: Cloning of cDNA Coding for the Entire Human Proα1 (I) Chain

1/ Preparation of a MG-63 cDNA Bank

The MG-63 cells (No. ATCC-CRL 1427) are derived from a human osteosarcoma. Approximately 28 million MG-63 cells cultivated in DMEM medium (Dulbecco's modified Eagle medium, Sigma™) are detached from the culture dishes by treatment with 0.25% trypsin, 0.05% EDTA (Ethylenediaminetetra-acetic acid). The cells are centrifuged at 1000 g for 10 min at 4° C., and the cell residue is treated with the RNA-Plus™ kit (BIOPROBE™ Systems) to purify total RNA. This manipulation was conducted following the instructions given by BIOPROBE™. A quantity of 950 μg total RNA was purified in this way.

The poly(A)+ RNAs were separated by chromatography on an oligo-dT cellulose column (Boehringer Mannheim) following the technique described by Aviv et al., (1972). A 0.1 N soda suspension containing 0.2 g oligo dT cellulose was deposited in a column. The column was washed with 3 ml sterile milli-Q water, then with 15 ml of 1×carrier buffer (20 mM Tris-Cl, pH 7.6; 0.5 M NaCl; 1 mM EDTA, pH8; 0.1% sodium lauryl sarcosinate). The effluent of the column equilibrated in this manner then has a pH of less than 8.

To a solution of total RNA (950 μg) incubated 5 min at 65° C. is added one volume of 2×carrier buffer (40 mM Tris-Cl, pH 7.6; 1 M NaCl; 2 mM EDTA, pH 8; 0.2% sodium lauryl sarcosinate). This mixture is cooled to room temperature before being deposited in the oligo dT cellulose column. The eluate is collected, incubated 5 min at 65° C., cooled to room temperature and passed again through the oligo-dT cellulose column. The column is then washed with 10 ml of 1×carrier buffer (20 mM Tris-Cl, pH 7.6; 0.5 M NaCl; 1 mM EDTA, pH 8; 0.1% sodium lauryl sarcosinate), which enables RNA poly(A)− elution, the RNA poly(A)+ remaining fixed to the dT cellulose matrix at their poly-adenylated 3' end. To the oligo dT-RNA poly(A)+ column are then added 2 ml of detachment buffer (10 mM Tris-Cl, pH 7.6; 1 mM EDTA, pH 8; 0.05% lauryl sulfate), and the eluate of RNA poly(A)+ is adjusted to 0.3 M in sodium acetate, pH 5.2 To this solution are added 2.2 volumes of 100% ethanol, and the RNA poly(A)+ are precipitated for 24 hours at −20° C.

After precipitation, the solution is centrifuged at 12000 g for 30 min at 4° C. The residue of RNA poly(A)+ is washed with 10 ml 70% ethanol, lyophilised and collected with 50 μl sterile milli-Q water. The concentration of this poly(A)+ RNA fraction is 1.2 mg/ml.

To form the cDNA bank, we used kits marketed by Amersham. These kits were:

cDNA synthesis system plus, RPN 1256
cDNA rapid adaptator ligation module, RPN 1712
cDNA rapid cloning module, RPN 1716
lambda-DNA in vitro packaging module, RPN 1717

Each stage was conducted following the manufacturer's protocol.

The RNA poly(A)+ solution was incubated 5 min at 65° C., then cooled in ice to remove the secondary structures present in some RNAs. This solution is divided into two fractions, and after pairing either by dT primer (12–18 mer) or random primers (hexanucleotides) with the RNA poly (A)+, synthesis of the first DNA strand (complementary to the RNA matrix) is conducted by reverse transcriptase. Ribonuclease H and DNA polymerase I of Escherichia coli are added to the RNA/DNA hybrid mixture. Ribonuclease H allows random cutting of the RNA strand in a RNA/DNA complex. DNA polymerase adds nucleotides to the free —OH 3' ends created by ribonuclease H through its 5'-3' polymerase activity. The 5'-3' exonuclease activity of DNA polymerase I allows removal of the ribonucleotide at 5' and to continue the synthesis of the second cDNA strand. After inactivating the enzymes by treatment at 70° C. for 10 min, the addition of T4 DNA polymerase yields blunt-ended double strand DNAs through its 3'-5' exonuclease activity. EcoRI adaptators are then ligated to the blunt ends of the cDNAs (complementary DNA). The free adaptators are removed on a column supplied by Amersham TM, and the EcoRI-adapted cDNAs are ligated in the EcoRI site of the MOSElox lambda vector. After ligation, in vitro encapsidation is conducted, which is the last stage before obtaining the cDNA bank. Approximately 800000 independent cDNA clones are obtained in this manner.

2/ Cloning of cDNA Coding for the Human Prowl (I) Chain.

a/ Preparation of ER1647 Bacteria Able to be Phage Infected.

This bacterial strain is recD−, mrc A-(Amersham™). These bacteria are held in 1.5% L-broth/agar dishes (L-broth: per liter, 10 g tryptone, 5 g yeast extracts, 10 g NaCl) supplemented with tetracycline (50 μg/ml). One ER1647 colony is seeded in 10 ml of L-broth/tetracycline (50 jig/ml), and the culture is made under stirring at 37° C. for 8 hours. The ER1647 culture is then centrifuged at 4° C. for 10 min at 3000 g, and the bacterial residue is re-suspended in 2 ml of cold 10 mM MgSO4.

b/ Preparation of Niro-cellulose Replicas:

For screening, 4 dishes (12×12 cm) 1.5% L-broth/agar of 25000 independent cDNA clones are made. For this purpose, 25000 phages from the cDNA bank are added to 250 µl of E1647 bacteria treated with 10 mM MgSO4. They are incubated at 37° C. for 15 min, the time needed for efficient infection of the bacteria. After adding 7 ml of 0.7% L-broth/agarose medium (Sigma™) maintained in liquid state at 45° C., the set-up is deposited on culture dishes (12×12 cm).

These dishes are incubated at 37° C. for 7–8 hours, the time needed for the onset of lysis plaques. They can then be used for the transfer of DNA from the lysis plaques onto nitro-cellulose replicas. The nitro-cellulose used is Hybond-C by Amersham™. For each dish, two replicas are made by simple lysis plaque/nitrocellulose replica contact. The contact time is 2 min for the first replica, and 4 min for the second. The DNA of phages present on the replicas is denatured for 4 min in a solution of 0.5 M soda, 1.5 M NaCl. The soda is then neutralised by two successive baths of 3 min in a solution of 1.5 M NaCl, 0.5 M Tris-Cl pH 7. The nitro-cellulose replicas are rinsed in a SSC 2×solution (0.3 M NaCl, 30 mM trisodic nitrate), dried on Whatman 3MM paper, and the denatured phage DNA is fixed on the nitro-celllulose replicas by incubation for 2 hours at 80° C.

c/ Preparation of Specific Probes of Human Type I Collagen

Two synthetic oligonucleotides are used to obtain probes specific to the proα1 (I) chain.

Oligonucleotide BIOC5, 5'-CTCGGGTTTCCACACGT-3' (SEQ. ID. NO.: 4), complementary sequence to nucleotides 152 to 178 specific to the proα1 (I) chain.

Oligonucleotide BIOC7, 5'-GCAAGACAG-TGATTGAA-3' (SEQ. ID. NO.: 5), sequence 4268 to 4274 specific to the chain proα1 (I).

These oligonucleotides are labelled with 32P, using gamma P32ATP at 3000 Ci/mmol (Amersham™) and T4 polynucleotide Kinase (Promega).

Labelling conditions, 50 ng BIOC5 or BIOC7 10.0 µl
H20 milli-Q 4.5 µl
gamma32PATP, 50 µCl 5.0 µl
T4 Polynucleotide kinase
(10 u/µl; Promega™) 0.5 µl This mixture is incubated for 30 min at 37° C. The reaction is halted by adding 1 ml 0.5 M EDTA, pH 8.

d/ Hybridisation of Nitro-cellulose Replicas

The nitro-cellulose replicas are deposited in 50 ml of a prehybridisation solution, and incubated at 50° C. for 15 min.

Prehybridisation solution:
6×SSC (0.3 M NaCl, 90 mM trisodic citrate)
  0.1% lauryl sulfate
  0.05% sodium pyrophosphate
  0.02% polyvinypyrolidone
  0.02% bovine serum albumin
  0.02% Ficoll 400
  Salmon sperm denatured DNA
    at 100 µg/ml (Boehringer Mannheim).

Both probes BIOC5 and BIOC7 are then added and hybridisation is conducted for 2 hours at 45° C. After hybridisation, the nitro-cellulose replicas undergo three successive baths of 15 min in order to remove aspecific hybridisations.

First bath: 6×SSC (0.9 M NaCl, 90 mM trisodic citrate), 0.05% sodium pyrophosphate, 15 min at room temperature.

Second bath: 3×SSC (0.45 M NaCl, 45 mM trisodic citrate), 0.05% sodium pyrophosphate, 15 min at room temperature.

Third bath: 6×SSC (0.9 M NaCl, 90 mM trisodic citrate), 0.05% sodium pyrophosphate, 15 min at 45° C.

The filters are then deposited on a plastic sheet, wrapped in a transparent plastic film and exposed to autoradiography at −80° C. for 24 hours in the presence of a film.

This operation enabled us to obtain several duplicate positive clones. Each positive lysis plaque in the two replicas is collected using a Pasteur pipette and deposited in 1 ml of SM buffer (100 mM NaCl, 8 mM MgSO4, 50 mM Tris-Cl pH 7.5, 0.01% gelatin).

With a second screening it was possible to purify the different positive clones, the conditions of hybridisation and washing of the nitro-cellulose replicas being the same as for the first screening. The clones purified during this second screening are collected and deposited in 500 µl of SM.

e/ Automatic sub-cloning of cDNA clones into plasmids using the cre-lox system.

The bacteriophage lambda vector MOSElox comprises an internal plasmid flanked at its two ends by the lox sites of 34 bp, derived from the P1 bacteriophage. Therefore, plasmid sub-clones may be obtained by infecting a bacterial strain expressing P1 cre recombinase which recognises the lox sequences surrounding the plasmid internal to the MOSElox lambda bacteriophage and which will enable excision of the plasmid by specific recombination at the lox sequences.

In our case, we used the bacterial strain BM25.8 which is lysogenic to P1 and lambda-imm434kan, both these plasmids being maintained by adding kanamycine (50 µg/ml) and chloramphenicol (50 µg/ml) to the growth medium of strain BMB25.8.

In practice, 10 ml of L-broth supplemented with kanamycine and chloramphenicol (50 µg/ml) are seeded with BM25.8 bacteria and incubated at 37° C. under shaking. When the DO600 of this culture is 0.9, incubation is halted and the bacteria can be stored for 3 days at 4° C.

An aliquot of the phage suspension of positive cDNA clones (10 µl) is placed in contact with 200 µl of BM25.8 bacteria, and the mixture incubated at 37° C. for 15 min in order to obtain efficient infection. The mixture is then deposited in a 1.5% L-broth/agar dish supplemented with ampicillin (50 µg/ml), and the dishes are incubated at 37° C. for 12 hours. The presence of ampicillin allows selection of those bacteria which have incorporated a bacteriophage, and more especially those in which a specific cre-lox recombination has occurred, the resulting plasmid having an ampicillin-resistant gene, and the cDNA insert at the EcoRI cloning site.

f/ Characterization of alpha22 and 1alpha3 cDNA Clones

Two of the positive complementary DNA clones were given subsequent use. These are the alpha22 and 1alpha3 cDNA clones.

To sequence these clones, 3 ml of L-broth supplemented with ampicillin (50 µg/ml) are seeded either with alpha22 or with 1alpha3. These mixtures are incubated overnight under shaking at 37° C.

To purify the plasmid DNA, the culture is first centrifuged at 1500 g for 10 min at 4° C., and the bacterial residue is treated with the Wizard kit (Promega™) which permits purification of the supercoiled plasmid DNA. This manipulation is conducted in accordance with the manufacturer's instructions. Approximately 10 µg of plasmid DNA is purified with this kit if the plasmid used is the MOSElox plasmid.

The last stage is to sequence the two ends of the alpha22 and 1alpha33 cDNA clones, in order to determine the information they hold.

To conduct 2 sequencing reactions, 40 µl DNA, namely 7–8 µg, purified with the Wizard system are denatured by adding 10 μl 2N NaOH and incubated 10 min at room temperature. After neutralisation through the addition of 12 μl 3 M sodium acetate pH 5.2, the monocatenary DNA is precipitated through the addition of 2.5 volumes ethanol 100 and incubation at −20° C. for 30 min. After precipitation, the DNA is centrifuged at 4° C. for 10 min at 12000 g, washed with 1 ml ethanol 70, freeze dried and collected in 20 μl milli-Q water.

The sequencing reactions were conducted with the "T7 sequencing" kit (Pharmnacia) which uses the chain termination technique and T7 DNA polymerase. The radio-element is [α-35S]-DATP (Amersham™) at 1350 Ci/mmol. The sequencing reactions were conducted following the recommendations made by the manufacturer.

Principle. After pairing a primer on a monocatenary DNA matrix, an elongation reaction is conducted with T7 DNA polymerase in the presence of dGTP, dTTP, dCTP and 35-SdATP. With the addition of an excess of the 4 cold dNTPs, and of ddATP (dideoxyadenosine triphosphate) or of ddGTP or ddCTP or ddTTP, it is possible to conduct 4 termination reactions separately. When a ddNTP is incorporated, the absence of the hydroxyl group blocks the elongation reaction.

In our case, the primers used are the oligonucleotides T7 gene 10 and T7 terminator (Amersham™) which are localised either side of the alpha22 and 1alpha33 cDNA clones.

T7 gene primer, 5'-TGAGGTTGTAGAAGTTCCG-3' (SEQ. ID. NO.: 6)

T7 terminator primer, 5'-GCTAGTTATTGCTCAGCGG-3' (SEQ. ID. NO.: 7)

Analysis of the sequences is conducted on polyacrylamide-urea gel (6%-7M). Sequencing gel.

The initial solution is: 39.6 g urea, 8.25 ml 10×TBE (0.9 M Tris borate, 20 mM EDTA, pH 8), 12.32 ml 40% acrylamide (38 g acrylamide, 2 g bis-acrylamide, to final volume 82.5 ml milli-Q water).

After dissolution of the urea, 400 μl of 10% ammonium persulfate and 66 μl TEMED (N, N, N', N'-tetramethyl-ethylene diamine) are added and the gel is poured. After polymerisation, the gel is preheated for 30 min at 60 kW. The samples are then deposited and subjected to separation under a power of 60 kW. After electrophoresis, the gel is transferred onto Whatman 3 MM paper, vacuum dried for 30 min at 80° C., and subjected to direct autoradiography at ambient temperature. On reading the sequences it was confirmed that the alpha22 and 1alpha3 cDNA clones code for the human proα1 (I) chain.

More precisely, the 1alpha3 cDNA clone comprises 83 bp of the untranslated 5' part and the first 1920 bases coding for the human proα1 (I) chain. The alpha22 cDNA clone comprises the sequence coding for amino acids 171 to 1454 of the human proα1 (I) chain and approximately 500 bp of the untranslated 3' region.

The conformity of the gene obtained was verified in relation to described sequences (LI S-W, 1994).

PREPARATION II

Cloning DNA Fragments Required for Producing the Constructs of the Invention

1/ Fragment A

Fragment A has 4 nucleotides (−4 to −1) upstream from the initiator codon of ATG translation, the entire sequence coding for the peptide signal (nucleotides 1 to 66) and for the amino-propeptide domain (nucleotides 67 to 479) of the human proα1 (I) chain. Nucleotides 474, 475 and 477, CTT, are substituted by the GCA bases which allows creation of a NheI restriction site (GCTAGC) from position 474 to 479. This creation of the NheI site leads to substitution of the Asn and Phe amino acids by a lysine and a leucine at position 158 and 159 of the human proα1 (I) chain.

Amplification of Fragment A

Two synthetic oligonucleotides were used.

Sense oligonucleotide BIOC85, 5'<u>TATCCGCG-GAAGCTTAGAC</u>ATGTTCAGCTTTGTGGACCTC-CGGCTCCTGC-3' (SEQ. ID. NO.: 8)

This oligonucleotide comprises at 5' (underlined nucleotides) the sequences permitting the creation of two restriction sites, SacII (CCGCGG) and HindIII (AAGCTT) which will be used as cloning sites. Following these two sites are included nucleotides −4 to −1 and 1 to 31 specific to the sequence encoding the human proc (I) chain.

Antisense oligonucleotide, BIOC83, 5'<u>TATTCTAGA-GCTAGC</u>TTTCCTCCGAGGCCAGGGGGTCCGG-GAGGT-3' (SEQ. ID. NO.: 9)

At 5' this oligonucleotide has the sequences (underlined nucleotides) permitting the creation of restriction sites XbaI (TCTAGA) and NheI (GCTAGC). The XbaI site will be used to clone fragment A, whereas the NheI site, described in the informative section, is used to delimit the sequence coding for the amino-propeptide domain. Following these two sites is the complementary sequence to nucleotides 445 to 474 of the sequence encoding the human proα1 (I) chain.

The DNA matrix used is the 1alpha3 cDNA clone which comprises 83 bp of the untranslated 5' part and the first 1920 bases coding for the human proα1 (I) chain.

To obtain fragment A, the amplification conditions by PCR (Polymerase Chain Reaction) were:

25 cycles: Denaturation 30 s at 94° C.
Pairing 30 s at 55° C.
Elongation 30 s at 72° C.

On completion of the 25 cycles, an additional extension of 5 min at 72° C. is conducted.

Initial solution:
75 mM Tris-Cl pH 9.0 (at 25° C.)
20 mM (NH4) 2S2O4
0.01% (Weight :volume) Tween 20
1.5 mM MgCl2
BIOC85, 0.5 mM
BIOC83, 0.5 mM
each dNTP, 0.2 mM
matrix, 1 ng 1alpha3 cDNA clone
0.25 unit DNA polymerase)

Cloning Fragment A

After amplification, the solution is extracted with one volume phenol/chloroform/isoamyl alcohol (ratio 50/48/2). After two minutes' centrifugation at 10000 g, the aqueous phase is collected and extracted with one volume chloroform/isoamyl alcohol (ratio 24/1). After centrifuging for a few seconds at 10000 g, the aqueous phase is collected, adjusted to a NaCl concentration of 0.2 M and two volumes alcohol 100 are added. The DNA is precipitated for 2 hours at −20° C., then centrifuged at 4° C. for 10 min at 12000 g. The DNA residue is washed in 1 ml ethanol 70, freeze dried, and resuspended in 34 μl sterile milli-Q water.

To this DNA solution are added 4 μl C digestion buffer (Promega™), 1 μl SacII restriction endo-nuclease (10 u/μl; Promega™) and 1 μl XbaI enzyme (12 μ/u)l; Promega). Digestion is carried out for 2 hours at 37° C.

Following enzymatic digestion, 8 μl stop buffer (30% sucrose, 0.25% bromophenol blue) are added to the DNA solution which is analysed by electrophoresis on 2% Nu-Sieve GTG agarose gel having a low melting point (FMC) at a constant voltage of 60 volts. The electrophoresis buffer is 0.5×TBE (45 mM Tris borate, 1 mM EDTA (ethylenediaminetetra-acetic acid) pH 8). After migration, the gel is stained for 15 min in a solution of 0.5×TBE containing 40 ng/ml ethidium bromide.

The band corresponding to fragment A is cut under UV, deposited in 350 µl of a solution of 20 mM Tris pH 8, 1 mM EDTA pH 8, and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2 M and precipitated 16 hours at −20° C. after addition of two volumes ethanol 100.

After centrifuging at 4° C. for 10 min at 12000 g, the DNA residue is washed with 1 ml ethanol 70, lyophilised and collected in 20 µl sterile milli-Q water. An aliquot of 2 µl, together with 500 ng of HindIII-EcoRI fragments of lambda phage (Promega™) are analysed on 2% type II agarose gel (Sigma™), which enabled us to estimate the concentration of the purified solution of fragment A SacII/XbaI at 30 ng/µl.

The plasmid used to clone fragment A is the pBluescript II SK(+) vector available from Stratagene™. This plasmid comprises an ampicillin-resistant gene.

A quantity of 200 ng of the pBluescript II SK(+) plasmid is subjected to digestion by the SacII and XbaI restriction endonucleases. This digestion is conducted in a volume of 20 µl in the presence of 2 µl C buffer (Promega™), 1 µl SacII enzyme (10 u/µl; Promega™) and 1 µl XbaI enzyme (12 u/µl; Promega™) for 2 hours at 37° C. After digestion, 2 µl carrier buffer (30% sucrose, 0.25% bromophenol blue) are added to the mixture and analysed on 0.8% Sea-plaque GTG agarose gel (FMC, Rockland) at a constant voltage of 60 volts, the electrophoresis buffer being 0.5×TBE. After electrophoresis, the gel is stained for 15 min in a 40 ng/ml solution of ethidium bromide. The DNA band corresponding to pBluescript II SK(+) linearized by SacII and XbaI is collected and deposited in 350 µl of a solution of 20 mM Tris pH 8, 1 mM EDTA pH 8. This sample is incubated for 5 min at 65° C., extracted with one volume of phenol and centrifuged for 5 min at 10000 g. The aqueous phase is collected, extracted with one volume phenol/chloroform/isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2 M and precipitated 16 hours at −20° C. after addition of two volumes ethanol 100.

After centrifuging at 4° C. for 10 min at 12000 g, the DNA residue is washed in 1 ml ethanol 70, lyophilised and collected in 20 µl sterile milli-Q water in order to obtain a 10 ng/ml solution of the plasmid pBluescript II SK(+) SacII/XbaI.

Ligation of fragment A (SacII/XbaI) to the plasmid pBluescript II SK(+) (SacII/XbaI) is conducted for 4 hours at room temperature.

For transformation, the competent bacteria used are DH5-Alpha (Gibco BRL, Paris). The genotype of this strain is: supE 44 Δ-lacU 169(Ø80 lacZΔM15) hsdR 17 recA endA 1 gyrA 96 thi-1 relA 1. To obtain competent bacteria, 5 ml of exponential phase culture (DO600 of 0.7) are centrifuged at 1500 g for 15 min at 4° C. The bacterial residue is then resuspended in 500 µl cold 100 mM CaCl2. For transformation, 10 µl of the ligation mixture is mixed with 200 µl competent DH5-Alpha bacteria, and the sample is placed at 4° C. for 30 min. After heat shock at 42° C. for 40 s, 500 µl L-broth (10 g tryptone, 5 g yeast extract, 10 g NaCl, per liter of medium) are added, and the mixture is incubated for 30 min at 37° C.

This mixture, together with 20 µl IPTG (Isopropylthyo-beta-D-galactoside; 200 mM) and 20 µl X-Gal (4 chloro-3 indolyl-beta-D galactoside; 20 mg/ml) are then deposited on a L-Broth-agar dish (L-broth plus 1.5% agar) supplemented with ampicillin (50 µg/ml), and the dish is incubated for 15 hours at 37° C. With the addition of IPTG and X-Gal it is possible to use the stain test to determine which plasmids have incorporated an insert.

The DH5-Alpha bacterial strain is Lac-, and produces a non-functional form of beta-galactosidase. The Bluescript II SK(+) vector has a DNA segment of the lactose operon of *Escherichia coli* which codes for the amino-terminal part of this enzyme. Synthesis induction by IPTG permits alpha complementation which restores the activity of this galactosidase. In the presence of a galactose analogue, X-Gal, the bacteria produce blue pigments which lead to the formation of a stained bacterial colony. The pBluescript II SK(+) vector has a multiple cloning region (comprising sites SacII/XbaI) situated in the LacZ gene. Insertion of fragment A into this cloning region deletes the alpha complementation, which leads to the formation of white bacterial colonies.

Several white colonies are tested. For testing, they deposited individually in 3 ml L-broth supplemented with ampicillin (50 µg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega) which permits purification of the supercoiled plasmid DNA. This manipulation is conducted according to the manufacturer's instructions. Approximately 10 µg plasmid DNA is purified with this kit, if the plasmid used is pBluescript II SK(+).

An aliquot (2 µl out of the 60 obtained) is subjected to enzymatic digestion by the restriction endonucleases SacI and XbaI, in order to verify cloning of fragment A. After electrophoresis, the gel is stained for 15 min in a 40 ng/ml ethidium bromide solution and the presence of fragment A is verified under UV illumination.

The last stage is to verify the integrity of the sequence of fragment A, since the PCR amplification technique (Polymerase Chain Reaction) can cause mutations.

The sequencing reactions conduced with the "T7 sequencing kit" (Pharmacia tM) which uses the chain termination technique and T7 DNA polymerase (cf PREPARATION 1) permits validation of the integrity of the sequence of fragment A.

2/ Fragment B

Fragment B has 3 bases (TAA) upstream from the sequence coding for the PRS peptide signal (PATHOGENESIS-RELATED PROTEIN S) (nucleotides 1 to 75) and bases 67 to 77 of the sequence coding for the amino-terminal part of the amino-propeptide domain of the human proα1 (I) chain. Nucleotides 73, 74 and 77, GAG, are substituted by bases CTC, which enables creation of a NheI restriction site (GCTAGC) at position 72 to 77. This creation of the NheI site leads to substitution of the Glu and Gly amino acids by a leucine and an alanine at positions 25 and 26 of the human proα1 (I) chain.

Amplification of Fragment B

Three synthetic nucleotides (BIOC95 and BIOC93 and 045) were used.

Matrix oligonucleotide, 045, 5'-TAAATGAACTT-CCTCAAAAGTTTCCCCTTTTATGCCTTCCTTTG-

TTTTGGCCAATACTTTGTAGCTGTTACTCATGC-
TGCC-3' (SEQ. ID. NO.: 10)

This oligonucleotide comprises in bold print the sequence corresponding to that of the peptide signal of PRS (PATHOGENESIS-RELATED PROTEIN S). It will serve as DNA matrix during PCR amplification (Polymerase Chain Reaction) of fragment B.

Sense oligonucleotide, BIO95, 5'-TATCCGCGG-AAGCTTTAAATGAACTTCCTCAAAAGTTTCCC-C-3' (SEQ. ID. NO.: 11)

At 5' this oligonucleotide has the sequences (underlined nucleotides) permitting creation of two restriction sites, SacII (CCGCGG) and HindIII (AAGCTT) which will be used as cloning sites. Following these two sites are included nucleotides −3 to −1 and 1 to 24 specific to the sequence coding for the peptide signal of PRS(PATHOGENIC-RELATED PROTEIN S).

Antisense oligonucleotide, BIOC93, 5'-ATGC-TAGCTCTTGAGCATGAGTAACAGCTACAAAG-TA-3' (SEQ. ID. NO.: 12)

At 5' this oligonucleotide has the sequence (underlined nucleotides) permitting creation of the restriction site NheI (GCTAGC). The NheI site described in the information section serves to delimit the sequence coding for the amino-propeptide domain. After the NheI site comes the sequence complementary to nucleotides 67 to 71 of the sequence encoding the human proα1 (I) chain and 52 to 75 of the sequence coding for the PRS (PATHOGENESIS-RELATED PROTEIN S) peptide signal.

Cloning of Fragment B

After PCR amplification, the solution is extracted with one volume phenol/chloroform/isoamyl alcohol (ratio 50/48/2), as described in preparation II1. The DNA residue is washed with 1 ml ethanol 70, freeze-dried and resuspended in 40 µl sterile milli-Q water.

An aliquot of 4 µl, together with 500 ng of HindIII-EcoRI fragments of lambda phage (Promega™) are analysed on 2% type II agarose gel (Sigma ™), which enabled us to estimate the concentration of the purified solution of fragment B at 20 ng/µl.

The plasmid used to clone fragment B is the pBluescript SK(+) vector available from Stratagene. This plasmid comprises an ampicillin-resistant gene.

A quantity of 200 ng of the plasmid pBluescript II SK(+) is subjected to digestion by the restriction endonuclease EcoRV (GATATC), to obtain a linearized vector with blunt ends. After digestion, 80 µl of TE (10 mM Tris, 1 mM EDTA, pH 8) are added and the solution is extracted with one volume phenol/chloroform/isoamyl alcohol (ratio 50/48/2) as described in preparation II1.

After centrifuging at 4° C. for 10 min at 12000 g, the DNA residue is washed in 1 ml ethanol 70, freeze-dried and collected in 20 µl sterile milli-Q water in order to obtain a 10 ng/ml solution of the plasmid pBluescript II SK(+) EcoRV.

Ligation of fragment B to the plasmid pBluescript II SK(+) (EcoRV) is conducted for 4 hours at ambient temperature.

For transformation, the competent bacteria used are DH5-Alpha (Gibco BRL, Paris) cf. above.

Several white colonies are tested. For this testing they are deposited individually in 3 ml L-Broth supplemented with ampicillin (50 µg/ml), and these cultures are incubated under shaking overnight at 37° C.

To purify the plasmid DNA, the culture is first centrifuged at 1500 g for 10 min at 4° C., and the bacterial residue is treated with the Wizard kit (Promega™) following the manufacturer's instructions.

An aliquot (2 µl out of the 60 obtained) is subjected to enzymatic digestion by the restriction endonucleases BamHI and HindIII in order to verify cloning of fragment B. The restriction sites BamHI and HindIII are localised either side of the EcoRV cloning site. After electrophoresis, the gel is stained for 15 min in a 40 ng/ml solution of ethidium bromide, and the presence of fragment B is verified under UV illumination.

The sequencing reactions conducted with the "T7 sequencing" kit (Pharmacia™) which uses the chain termination technique and T7 DNA polymerase (cf PREPARATION I) permit validation of the integrity of the sequence of fragment B.

3/ Fragment C

Fragment C has virtually all the sequence coding for the amino-propeptide domain (nucleotides 72 to 479) of the human proα1(I) chain. Nucleotides 73, 74 and 77, GAG, are substituted by the bases CTC, which permits creation of a NheI restriction site (GCTAGC) at position 72 to 77. This creation of the NheI site leads to substitution of the Glu and Gly amino acids by a leucine and an alanine at position 25 and 26 of the human proα1 (I) chain. Nucleotides 474, 475 and 477, CTT, are substituted by bases GCA, which permits creation of a NheI restriction site (GCTAGC) at position 474 to 479. This creation of the NheI site leads to substitution of amino acids Asn and Phe by a lysine and a leucine at position 158 and 159 of the human proα1(I) chain.

Amplification of Fragment C

Two synthetic oligonucleotides were used.

Sense oligonucleotide, BIOC855, 5'-ATGCT-AGCCCAAGTCGAGGGCCAAGACGAAG-3' (SEQ. ID. NO.: 13)

At 5' this oligonucleotide comprises the sequence (underlined nucleotides) permitting creation of a NheI restriction site (GCTAGC) which will be used as a cloning site. The NheI site, described in the information section, serves to delimit the sequence coding for the amino-propeptide domain (amino-terminal end). Following this site nucleotides 78 to 100 are included, specific to the sequence encoding the 25 human proα1(I) chain.

Antisense oligonucleotide, BIOC83, 5'-TATTCTA-GAGCTAGCTTTCCTCCGAGGCCAGGGGG-TCCGGGAGGT-3' (SEQ. ID. NO.: 9)

At 5' this oligonucleotide comprises the sequences (underlined nucleotides) permitting creation of the XbaI (TCTAGA) and NheI (GCTAGC) restriction sites. The XbaI site used during cloning of fragment A will not be used for fragment C. Site NheI, described in the information section, serves to delimit the sequence coding for the amino-propeptide domain (carboxy-terminal end). Following after these two sites is the sequence complementary to nucleotides 445 to 474 of the sequence encoding the human proα1 (I) chain.

The DNA matrix used is the 1alpha3 cDNA clone which comprises 83 bp of the untranslated 5' part and the first 1920 bases coding for the human proα1(I) chain.

Cloning of Fragment C

After amplification, the solution is extracted with one volume phenol/chloroform/isoamyl alcohol (ratio 50/48/2) as described in preparation II1. The DNA residue is washed in 1 ml ethanol 70, freeze-dried and resuspended in 40 ml sterile milli-Q water.

An aliquot of 4 µl, together with 500 ng of the HindIII-EcoRI fragments of lambda phage (Promega™) are analysed on 2% type II agarose gel (Sigma™), which enabled us to estimate the concentration of the purified solution of fragment C at 20 ng/µl.

The plasmid used to clone fragment C is the pBluescript II SK(+) vector available from Stratagene™ (La jolla). This plasmid comprises an ampicillin-resistant gene.

A quantity of 200 ng of the pBluescript II SK(+) plasmid is subjected to digestion by the restriction endonuclease EcoRV (GATATC), which leads to obtaining a linearized vector with blunt ends. After digestion, 80 μl of TE (10 mM Tris, 1 mM EDTA, pH 8) are added and the solution is extracted with one volume phenol/chloroform.isoamyl alcohol (ratio 50/48/2) as described in PREPARATION II1.

After centrifuging at 4° C. for 10 min at 12000 g, the DNA residue is washed in 1 ml 70 ethanol, freeze dried and collected in 20 μl sterile milli-Q water in order to obtain a 10 ng/ml solution of the plasmid pBluescript II SK(+) EcoRV. Ligation of fragment C to the plasmid pBluescript II SK(+) (EcoRV) is conducted for 4 hours at ambient temperature.

For transformation, the competent bacteria used are DH5-Alpha (Gibco BRL, Paris).

Several white colonies are tested. For this testing, they are deposited individually in 3 ml L-Broth supplemented with ampicillin (50 μg/ml), and these cultures are incubated overnight under shaking at 37° C.

To purify the plasmid DNA, the culture is first centrifuged at 15000 g for 10 min at 4° C., and the bacterial residue is treated with the Wizard kit (Promega™) following the manufacturer's instructions.

An aliquot (2 μl out of the 60 obtained) is subjected to enzymatic digestion by the restriction endonucleases BamHI and HindIII, in order to verify cloning of fragment C. The restriction sites BamHI and HindIII are localized either side of the EcoRV cloning site. After electrophoresis; the gel is stained for 15 min in a 40 ng/ml solution of ethidium bromide, and the presence of fragment C is verified under UV illumination.

The sequencing reactions conducted with the "T7 sequencing" kit (Pharmacia™) which uses the chain termination technique and T7 DNA polymerase (cf. PREPARATION I) permits validation of the integrity of the sequence of fragment C.

4/ Fragment D

Fragment D comprises the entire sequence coding for the amino-telopeptide domain (nucleotides 474 to 534) and the sequence coding for the amino-terminal part of the helical region (nucleotides 535 to 1920) of the human proα1(I) chain. Nucleotides 474, 475 and 477, CTT, are substituted by bases GCA, which permits creation of a NheI restriction site (GCTAGC) at position 474 to 479. This creation of the NheI site leads to substitution of amino acids Asn and Phe by a lysine and a leucine at position 158 and 159 of the human proα1(I) chain. A DraIII restriction site is localized at position 1709 to 171 (CACCTGGTG), whereas a BamHI site due to the lambda plasmid MoSElox (Amersham™) is situated at the 3' end.

Amplification of Fragment D

Two synthetic oligonucleotides were used.

Sense oligonucleotide, BIOC65, 5'-<u>TATTCTAGAG-CTAGC</u>TCCCCAGCTGTCTTATGGCTATGATGAG -3' (SEQ. ID. NO.: 14)

At 5' this oligonucleotide comprises the sequence (underlined nucleotides) permitting creation of the XbaI (TCTAGA) and NheI (GCTAGC) restriction sites. The XbaI site will be used for cloning fragment D, whereas the NheI site, described in the information section, serves to delimit the sequence coding for the amino-propeptide domain. Following after these two sites is the sequence (nucleotides 480 to 507) coding for the start of the amino-telopeptide domain of the human proα1 (I) chain.

Antisense oligonucleotide, T7 gene 10 primer, 5'-CTGAGGTTGTAGAAGTTCCG-3' (SEQ. ID. NO.: 15)

This oligonucleotide is localized just downstream from the 3' end of the 1alpha3 cDNA clone, and from a BamHI restriction site (GGATTC) which will be used for cloning fragment D.

The DNA matrix used is the 1alpha3 cDNA clone which comprises 83 bp of the untranslated 5' part and the first 1920 bases coding for the human proα1 (I) chain.

Cloning Fragment D

After amplification, the solution is extracted with one volume phenol/chloroform/isoamyl alcohol (ratio 50/48/2) as in PREPARATION II1. The DNA residue is washed in 1 ml ethanol 70, freeze dried and resuspended in 34 ml sterile milli-Q water.

Digestion with Bam HI XbaI is conducted for 2 hours at 37° C. in a final volume of 40 μl.

Subsequent to enzymatic digestion, 8 μl stop buffer (30% sucrose, 0.25% bromophenol blue) are added to the DNA solution which is analyzed by electrophoresis on 0.8% SeaPlaque-GTG agarose gel with a low melting point (FMC, Rockland) at a constant voltage of 60 volts. The electrophoresis buffer is 0.5×TBE (45 mM Tris borate, 1 mM EDTA (ethylenediaminetetra-acetic acid), pH8). After migration, the gel is stained for 15 min in a 0.5×TBE solution containing 40 ng/ml ethidium bromide.

The band corresponding to fragment D is cut under UV illumination, deposited in 350 μl of a solution of 20 mM Tris pH 8, 1 mM EDTA pH 8, and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2), as described for preparation II1.

After centrifuging at 4° C. for 10 min at 12000 g, the DNA residue is washed in 1 ml ethanol 70, freeze dried and collected in 20 μl sterile milli-Q water. An aliquot of 2 μl, together with 500 ng of the HindIII-EcoRI fragments of lambda phase (Promega ™) are analyzed on 0.8% type II agarose gel (Sigma™) which enabled us to estimate the concentration of the purified solution of fragment D BamHI/XbaI at 50 ng/μl.

The plasmid used to clone fragment D is the PUC 18 vector marketed by Promega(™). This plasmid comprises an ampicillin-resistant gene.

A quantity of 200 ng of pUC18 plasmid is subjected to digestion by the restriction endonucleases BamHI and XbaI for 2 hours at 37° C. After digestion, 2 μl carrier buffer (30% sucrose, 0.25% bromophenol blue) are added to the mixture and analyzed on 0.8% Seaplaque-GTG agarose gel (FMC, Rockland). The DNA band corresponding to pUC18 linearized by BamHI and XbaI is collected and deposited in 350 μl of a solution of 20 mM Tris pH 8, 1 mM EDTA pH 8. This sample is incubated for 5 min at 65° C., extracted with one volume of phenol and centrifuged for 5 min at 10000 g. The aqueous phase is collected, extracted with one volume phenol/chloroform/isoamyl alcohol (ratio 50/48/2) as described in PREPARATION After centrifuging at 4° C. for 10 min at 12000 g, the DNA residue is washed in 1 ml ethanol 70, freeze dried and collected in 20 μl sterile milli-Q water in order to obtain a 10 ng/ml solution of the plasmid pUC18 BamHI/XbaI.

Ligation of fragment D (BamHI/XbaI) to plasmid pUC18 (BamHI/XbaI) is conducted for 4 hours at ambient temperature.

For transformation, the competent bacteria used are DH5-alpha (Gibco BRL, Paris).

Several white colonies are tested. For this testing, they are deposited individually in 3 ml L-Broth supplement with ampicillin (50 µg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) to purify the supercoiled plasmid DNA. This manipulation is conducted following the manufacturer's instructions. Approximately 10 µg plasmid DNA is purified with this kit if the plasmid used is pUC18.

An aliquot (2 µl out of the 60 obtained) is subjected to enzymatic digestion with the BamHI and XbaI restriction endonucleases in order to verify the cloning of fragment D. After electrophoresis, the gel is stained for 15 min in a 40 ng/ml solution of ethidium bromide, and the presence of fragment D is verified under UV illumination.

The sequencing reactions made with the "T7 sequencing" kit (Pharmacia™) which uses the chain termination technique and T7 DNA polymerase (cf. PREPARATION I) permits validation of the integrity of the sequence of fragment D.

5/ Fragment E

Frgament E lies between sites DraIII (CACCTGGTG, nucleotides 1709 to 1717) and BamHI (GGATCC, nucleotides 2803 to 2808) present in the alpha22 cDNA clone. This fragment codes for amino acids 567 to 936 lying in the central helical domain of the human proα1 (I) chain.

6/ Fragment F

Fragment F lies between sites BamHI (GGATCC, nucleotides 2803 to 2808) and EcoRI (GAATTC, nucleotides 4357 to 4362) present in the alpha22 cDNA clone. This fragment codes for amino acids 936 to 1192 lying in the central helical domain and 1193 to 1454 in the carboxy-propeptide domain of the human proα1 (I) chain.

7/ Fragment G

Fragment G comprises the sequence (nucleotides 4040 to 4392) coding for the carboxy-terminal part of the carboxy-propeptide domain (amino acids 1346 to 1464) of the human proα1 (I) chain. This fragment also comprises the TAA nucleotides (stop codon, bases 4393 to 4395) coupled to a HinIII (AAGCTT) restriction site.

Amplification of fragment G

Two synthetic oligonucleotides were used.

Sense oligonucleotide, BIOC25, 5'-<u>TATCTGCA-GAT</u>GTGGCCATCCAGCTGACCT-3'-3' (SEQ. ID. NO.: 16)

At 5' this oligonucleotide comprises the sequence (underligned nucleotides permitting creation of the PstI (CTGCAG) restriction site which will be used as a cloning site. Following after this site, are nucleotides 4040 to 4060 specific to the sequence encoding the human proα1 (I) chain.

Antisense oligonucleotide, BIOC23, 5'-TAT<u>AAGCTT</u>A-CAGGAAGCAGACAGGGCCAA -3' (SEQ. ID. NO.: 17)

At 5' this oligonucleotide comprises the sequence (underlined nucleotides) permitting creation of the HindIII (AAGCTT) restriction site. The bold print denotes the sequence complementary to the TAA stop codon, followed by the complementary strand of nucleotides 4373 to 4392 of the sequence coding for the human proα1 (I) chain.

The DNA matrix used is the alpha22 cDNA clone which comprises the sequence coding for amino acids 171 to 1454 of the human proα1 (I) chain and approximately 500 bp of the untranslated 3' region.

Cloning of Fragment G

After amplification, the solution is extracted with one volume phenol/chloroform/isoamyl alcohol (ratio 50/48/2).

The DNA residue is washed in 1 ml ethanol 70, freeze dried and resuspended in 35 µl sterile milli-Q water.

Digestion by Pst1 is conducted for 2 hours at 37° C. in the final volume of 40 µl.

Subsequent to enzymatic digestion, 60 µl TE buffer (10 mM Tris, 1 mM EDTA, pH 8) are added to the DNA solution, which is extracted with one volume phenol/chloroform/isoamyl alcohol (ratio 50/48/2) as described for PREPARATION II1.

After centrifuging at 4° C. for 10 min at 12000 g, the DNA residue is washed in 1 ml 70 ethanol, freeze dried and collected in 35 ml sterile milli-Q water. Digestion by HindIII is conducted for 2 hours at 37° C. in a final volume of 20 µl.

Subsequent to enzymatic digestion, 8 µl stop buffer (30% sucrose, 0.25% bromophenol blue) are added to the DNA solution which is analyzed by electrophoresis on 2% Nu Sieve-GTG agarose gel with a low melting point (FMC, Rockland) cf. PREPARATION II2.

The band corresponding to fragment G is cut under UV illumination, deposited in 350 µl of a solution of 20 mM Tris pH 8, 1 mM EDTA pH8, and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2) as described for PREPARATION II1.

After centrifuging at 4° C. for 10 min at 12000 g, the DNA residue is washed in 1 ml ethanol 70, freeze dried and collected in 20 µl sterile milli-Q water. An aliquot of 2 µl, together with 500 ng of the HindIII-EcoRI fragments of lambda phage (Promega ™) are analyzed on 2% type II agarose gel (Sigma™) which enabled us to estimate the concentration of the purified solution of fragment G HindIII/PstI at 30 ng/µl.

The plasmid used to clone fragment G is the pBluescript II SK(+) vector available from Stratagene. This plasmid comprises an ampicillin-resistant gene.

200 ng of the pBluescript II SK(+) plasmid is subjected to digestion by the PstI restriction endonuclease in a final volume of 20 µl for 2 hours at 37° C. After digestion, 80 µl TE buffer (10 mM Tris, 1 mM EDTA, pH 8) are added to DNA solution which is extracted with one volume phenol/chloroform/isoamyl alcohol (ratio 50/48/2) as described for PREPARATION II1.

After centrifuging at 4° C. for 10 min at 12000 g, the DNA residue is washed in 1 ml ethanol 70, freeze dried and collected in 17 µl sterile milli-Q water. Digestion by HindIII is conducted for 2 hours at 37° C. in a final volume of 20 µl.

After digestion, 4 µl carrier buffer (30% sucrose, 0.25% bromophenol blue) are added to the mixture and analyzed on 0.8% Seaplaque GTG agarose gel (FMC, Rockland), cf. PREPARATION II4. The DNA band corresponding to the pBluescript SK(+) plasmid linearized by HindIII and PstI is collected and deposited in 350 µl of a solution of 20 mM Tris pH 8, 1 mM EDTA pH 8. This sample is incubated for 5 min at 65° C., extracted with one volume of phenol and centrifuged for 5 min at 10000 g. The aqueous phase is collected, extracted with one volume phenol/chloroform/isoamyl alcohol (ratio 50/48/2) as described for PREPARATION II1.

After centrifuging at 4° C. for 10 min at 12000 g the DNA residue is washed in 1 ml ethanol 70, freeze dried and collected in 20 µl sterile milli-Q water in order to obtain a 10 ng/µl solution of the plasmid pBluescript II SK(+) HindIII/PstI.

Ligation of fragment G (HindIII/PstI) to the plasmid pBluescript II SK(+) (HindIII/PstI) is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with ampicillin (50 µg/ml), and these cultures are incubated overnight under shaking at 37° C.

To purify the plasmid DNA, the culture is first centrifuged at 1500 g for 10 min at 4° C., and the bacterial residue is treated with the Wizard kit (PROMEGA™) following the manufacturer's instructions.

An aliquot (2 µl out of the 60 obtained) is subjected to enzymatic digestion by the HindIII and BamHI restriction endonucleases in order to verify cloning of fragment G.

After electrophoresis, the gel is stained for 15 min in a 40 ng/ml solution of ethidium bromide, and the presence of fragment G is verified under UV illumination.

The sequencing reactions made with the "T7 sequencing" kit (Pharmacia™) which uses the chain termination technique and T7 DNA polymerase (cf. PREPARATION 1) permit validation of the integrity of the sequence of fragment G.

8/ Fragment H

Fragment H comprises the sequence (nucleotides 4031 to 4383) coding for the carboxy-terminal part of the carboxy-propeptide domain (amino acids 1343 to 1461) of the human proα1 (I) chain. This fragment also comprises the TAA nucleotides (stop codon, bases 4384 to 4386) coupled to a HindIII (AAGCTT) restriction site. Upstream from the stop codon lie the codons Lys, Asp, Glu, Leu, site of retention in the endoplasmic reticulum.

b/ Amplification of Fragment H

Two synthetic oligonucleotides were used.

Sense oligonucleotide, BIOC25, 5'-TAT<u>CTGCAG</u>AT-GTGGCCATCCAGCTGACCT-3'-3' (SEQ. ID. NO.: 16)

At 5' this oligonucleotide comprises the sequence (underlined nucleotides) permitting creation of the PstI (CTGCAG) restriction site which will be used as a cloning site. Following after this site lie nucleotides 4031 to 4051 specific to the sequence coding for the human proα1 (1) chain.

Antisense oligonucleotide, BIOCKDEL, 5'TAT<u>AAGCTT</u>-ATAGCTCATCTTTCAGGAAGCAGACAGGGCC-AACGTCGAAGC-3' (SEQ. ID. NO.: 18)

At 5' this oligonucleotide comprises the sequence (underligned nucleotides) permitting creation of the HindIII (AAGCTT) restriction site. The bold print indicates the sequence complementary to the TAA stop codon and to the KDEL (SEQ. ID. NO.: 1) amino acids, followed by the complementary strand of nucleotides 4353 to 4383 of the sequence coding for the human proα1 (I) chain.

The DNA matrix used is the alpha22 cDNA clone which comprises 110 bp of the untranslated 5' part and the first 1911 bases coding for the human proα1 (I) chain.

Cloning of Fragment H

After amplification, the solution is extracted with one volume phenol/chloroform/isoamyl alcohol (ratio 50/48/2) as described for PREPARATION II1. The DNA residue is washed in 1 ml ethanol 70, freeze dried and resuspended in 36 µl sterile milli-Q water.

Digestion by PstI is conducted for 2 hours at 37° C. in a final volume of 40 µl.

Subsequent to enzymatic digestion, 60 µl of TE buffer (10 mM Tris, 1 mM EDTA, pH 8) are added to the DNA solution which is extracted with one volume phenol/chloroform/isoamyl alcohol (ratio 50/48/2) as described for PREPARATION II1.

After centrifuging at 4° C. for 10 min at 12000 g the DNA residue is washed in 1 ml ethanol 70, freeze dried and collected in 35 µl sterile milli-Q. Digestion by HIND III is conducted for 2 hours at 37° C. in a final volume of 40 µl.

Subsequent to enzymatic digestion, 8 µl stop buffer (30% sucrose, 0.25% bromophenol blue) are added to the DNA solution which is analyzed by electrophoresis on 2% Nu sieve-GTG agarose gel with low melting point (FMC, Rockland) as described for PREPARATION II1.

The band corresponding to fragment H is cut under TV illumination, deposited in 350 µl of a solution of 20 mM Tris pH 8, 1 mM EDTA pH 8, and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2) as described for

PREPARATION II1.

After centrifuging at 4° C. for 10 min at 12000 g the DNA residue is washed in 1 ml ethanol 70, freeze dried and collected in 20 µl sterile milli-Q water. An aliquot of 2 µl, together with 500 ng of the HindIII-EcoRI fragments of lambda phage (Promega ™) are analyzed on 2% type agarose gel (Sigma™) which enabled us to estimate the concentration of the purified solution of fragment H HindIII/PstI at 20 ng/µl.

The plasmid used to clone fragment H is the pBluescript II SK(+) plasmid available from Stratagene™. This plasmid comprises an ampicillin-resistant gene.

200 ng of the pBluescript II SK(+) plasmid is subjected to digestion by the PstI restriction endonuclease, in a volume of 20 f for 2 hours at 37° C. After digestion, 80 µl of TE buffer (10 mM Tris, 1 mM EDTA, pH 8) are added to the DNA solution which is extracted with one volume phenol/chloroform/isoamyl alcohol (ratio 50/48/2) as described for PREPARATION II 1.

After centrifuging at 4° C. for 10 min at 12000 g the DNA residue is washed in 1 ml ethanol 70, freeze dried and collected in 17 µl sterile milli-Q water. Digestion by HIN-DIII is conducted for 2 hours at 37° C. in a final volume of 20 µl.

After digestion, 4 µl carrier buffer (30% sucrose, 0.25% bromophenol blue) are added to the mixture and analyzed on 0.8% Seaplaque GTG agarose gel (FMC, Rockland), cf. PREPARATION 114. The DNA band corresponding to pBluescript II SK(+) linearized by HindIII and PstI is collected and deposited in 350 µl of a solution of 20 mM Tris pH 8, 1 mM EDTA pH 8. This sample is incubated for 5 min at 65° C., extracted with one volume of phenol and centrifuged for 5 min at 10000 g. The aqueous phase is collected, extracted with one volume phenol/chloroform/isoamyl alcohol (ratio 50/48/2) as described for PREPARATION II1.

After centrifuging at 4° C. for 10 min at 12000 g, the DNA residue is washed in 1 ml ethanol 70, freeze dried and collected in 20 µl sterile milli-Q water in order to obtain a 10 ng/ml solution of the plasmid pBluescript II SK(+) HindIII/PstI.

Ligation of fragment H (HindIII/PstI) to the plasmid pBluescript II SK(+) (HindIII/PstI) is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with ampicillin (50 μg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) following the manufacturer's instructions.

An aliquot (2 mμl out of the 60 obtained) is subjected to enzymatic digestion by the HindIII and BamHI restriction endonucleases in order to verify cloning of fragment H. After electrophoresis, the gel is stained for 15 min in a 40 ng/ml solution of ethidium bromide, and the presence of fragment H is verified under UV illumination.

The last stage is to verify the integrity of the sequence of fragment H, since the PCR (polymerase chain reaction) technique for amplification may give rise to mutations. The sequencing reactions made with the "T7 sequencing" kit (Pharmacia™) which uses the chain termination technique and T7 DNA polymerase (cf. PREPARATION 1) permit validation of the integrity of sequence of fragment G.

EXAMPLE 1

Construction of Chimeric Genes Coding for the Recombinant Protein of Human Collagen and Allowing Expression in Tobacco Leaves and the Grains of Tobacco or Colza.

1/ Obtaining Fragments FG and FH

This stage consists of cloning fragment BamHI/EcoRI of 1554 bp (nucleotides 2803 to 4357) of the alpha22 clone between sites BAMHI (of the pBluescript II SK(+) vector) and EcoRI (fragment G or H) of the clone pBluescript II SK(+)-fragment G or H. This leads to obtaining clones pBluescript II SK(+)-FG and pBluescript II SK(+)-FH which comprise, between sites BamHI and HindIII, the sequence coding for amino acids 936 to 1192 of the central helical domain, the entire carboxy-propeptide domain (amino acids 1193 to 1464) of the human proα1 (I) chain and the TAA stop codon coupled to the HindIII restriction site. In respect of clone pBluescript II SK(+)-fragment FH, 4 codons specific to the KDEL (SEQ. ID. NO.: 1) sequence (Lys, Asp, Glu, Leu) are inserted between the sequence coding for the carboxy-propeptide domain and the TAA stop codon.

Cloning Fragment F (BamHI/EcoEI) With the EcoRI/HindIII Part of Fragment G or H.

Approximately 1 μg of the alpha22 cDNA clone are digested by the restriction endonuclease BamHI for 90 min at 37° C. The conditions used are: 1 μg alpha22, 2 μl E digestion buffer (Promega™), 1 μl BamHI restriction endonuclease (12 u/μl; Promega™) to a final volume of 20 μl milli-Q H20. Digestion is conducted for 2 hours at 37° C.

Subsequent to enzymatic digestion, 80 μl TE buffer (10 mM Tris, 1 mM EDTA, PH 8) are added to the DNA solution which is extracted with one volume phenol/chloroform/isoamyl alcohol (ratio 50/48/2) as described in PREPARATION II1.

After centrifuging at 4° C. for 10 min at 12000 g, the DNA residue is washed in 1 ml ethanol 70, freeze dried and collected in 35 μl sterile milli-Q water. Digestion by PstI is conducted for 2 hours at 37° C. in a final volume of 40 μl.

Subsequent to enzymatic digestion, 8 μl stop buffer (30% sucrose, 0.25% bromophenol blue) are added to the DNA solution which is analyzed by electrophoresis on 1% Seaplaque-GTG agarose gel with low melting point (FMC, Rockland) at a constant voltage of 60 volts. The electrophoresis buffer is 0.5×TBE (45 mM Tris borate, 1 mM EDTA (ethylenediaminetetra-acetic acid) pH 8). After migration, the gel is stained for 15 min in a 0.5×TBE solution containing 40 ng/ml ethidium bromide.

The band corresponding to the BamHI/EcoRI fragment of 1554 bp is cut under UV illumination, deposited in 350 μl of a solution of 20 mM Tris pH 8, 1 mM EDTA pH 8, and incubated for 5 min at 65° C. After dissolution of the agarose, the sample is extracted with one volume phenol and centrifuged for 5 min at 10000 g. The aqueous phase is collected, extracted with one volume phenol/chloroform/isoamyl alcohol (ratio 50/48/2) as described in PREPARATION II1.

After centrifuging at 4° C. for 10 min at 12000 g, the DNA residue is washed in 1 ml ethanol 70, freeze dried and collected in 20 μl sterile milli-Q water. An aliquot of 2 μl, together with 500 ng of the HindIII-EcoRI fragments of lambda phage (Promega™) are analyzed on 1% type II agarose gel (Sigma™), which enabled us to estimate the concentration of the purified solution of the BamHI/EcoRI fragment of clone alpha22 cDNA at 12 ng/μl.

The plasmid used to clone the BamHI/EcoRI fragment of the alpha 22 cDNA clone is the clone pBluescript II SK(+)-fragment G or H digested by the BamHI and EcoRI enzymes. This clone comprises an ampicillin-resistant gene.

500 ng of the plasmid pBluescript II SK(+)-fragment G or H is subjected to digestion by the BamHI restriction endonuclease, in a volume of 20 μl for 2 hours at 37° C. After digestion, 80 μl of TE buffer (10 mM Tris, 1 mM EDTA, pH 8) are added to the DNA solution which is extracted with one volume phenol/chloroform/isoamyl alcohol (ratio 50/48/2) as described in PREPARATION II1.

After centrifuging at 4° C. for 10 min at 12000 g, the DNA residue is washed in 1 ml ethanol 70, freeze dried and collected in 17 μl sterile milli-Q water. Digestion by EGRI is conducted for 2 hours at 37° C. in a final volume of 20 μl.

After digestion, 4 μl of carrier buffer (30% sucrose, 0.25% bromophenol blue) are added to the mixture and analyzed on 0.8% Seaplaque GTG agarose gel (FMC, Rockland), cf. PREPARATION II4. The DNA band corresponding to pBluescript II SK(+)-fragment G or H digested by BamHI and EcoRI is collected and deposited in 350 μl of a solution of 20 mM Tris, 1 mM EDTA pH 8. This sample is incubated for 5 min at 65° C., extracted with one volume of phenol and centrifuged for 5 min at 10000 g. The aqueous phase is collected, extracted with one volume phenol/chloroform/isoamyl alcohol (ratio 50/48/2) as described in PREPARATION II1.

After centrifuging at 4° C. for 10 min at 12000 g the DNA residue is washed in 1 ml ethanol 70, freeze dried and collected in 20 μl sterile milli-Q water in order to obtain a 20 ng/ml solution of the plasmid pBluescript II SK(+)-fragment G or H (BamHI/EcoRI).

Ligation of the BamHI/EcoRI fragment of the alpha22 cDNA clone to the clone pBluescript II SK(+)-fragment G or H (BamHI/EcoRI) is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with ampicillin (50 μg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) following the manufacturer's instructions.

An aliquot (2 μl out of the 60 obtained) is subjected to enzymatic digestion by the HindIII and BamHI restriction endonucleases, in order to verify cloning of the BamHI/EcoRI fragment of the alpha22 cDNa clone to clone pBluescript II SK(+)-fragment G or H (BamHI/EcoRI). The HindIII restriction site is coupled to the TAA stop codon at 3' of the EcoRI site.

After electrophoresis, the gel is stained for 15 min in a 40 ng/ml solution of ethidium bromide, and the presence of the BamHI/HindIII fragment of 1596 bp for the FG fragment and of 1608 bp for the FH fragment is verified under UV illumination.

The sequencing reactions made with the "T7 sequencing" kit (Pharmacia™) which uses the chain termination technique and T7 DNA polymerase permit validation of the integrity of the clones pBluescript II SK(+)fragment FG and pBluescript II SK(+)-fragment FH.

2/ Obtaining Fragment DE

This stage consists of cloning fragment DraIII/BamHI (nucleotides 1714 to 2803) of 1809 bp of the alpha22 clone between sites DraIII (of fragment D) and BamHI (of plasmid pUC18) of clone pUC18-fragment D. This leads to obtaining clone pIC18-DE which comprises between sites XbaI and BamHI the sequence coding for amino acids 160 to 179 of the amino-telopeptide domain, amino acids 180 to 936 of the central helical region of the human proα1 (I) chain.

Cloning fragment E (DraIII/BamHI) With the DraII/BamHI Part of Fragment D.

Approximately 1 µg of the alpha22 cDNA clone are digested by the restriction endonuclease BamHI for 90 min at 37° C.

Subsequent to enzymatic digestion, 80 µl TE buffer (10 mM Tris, 1 mM EDTA, pH 8) are added to the DNA solution which is extracted with one volume phenol/chloroform/isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2 M, and precipitated for 16 hours at −20° C. after addition of two volumes ethanol 100.

After centrifuging at 4° C. for 10 min at 12000 g, the DNA residue is washed in 1 ml ethanol 70, freeze dried and collected in 35 µl sterile milli-Q water. Digestion by DraIII is conducted for 2 hours at 37° C. in a final volume of 40 µl.

Subsequent to enzymatic digestion, 8 µl stop buffer (30% sucrose, 0.25% bromophenol blue) are added to the DNA solution which is analyzed by electrophoresis on 1% Seaplaque-GTG agarose gel with low melting point (FMC, Rockland), cf. EXAMPLE I1.

The band corresponding to fragment DraIII/BamHI of 1089 bp of the alpha22 cDNA clone is cut under UV, deposited in 350 µl of a solution of 20 mM Tris pH 8,1 mM EDTA pH 8, and incubated for 5 min at 65° C. After dissolution of the agarose, the sample is extracted with one volume phenol and centrifuged for 5 min at 10000 g. The aqueous phase is collected, extracted with one volume phenol/chloroform/isoamyl alcohol (ratio 50/48/2) cf. PREPARATION II1.

After centrifuging at 4° C. for 10 min at 12000 g, the DNA residue is washed in 1 ml ethanol 70, freeze dried and collected in 20 µl sterile milli-Q water. An aliquot (2 µl), together with 500 ng of the HindIII-EcoRI fragments of lambda phage (Promega™) are analyzed on 2% type II agarose gel (Sigma™), which enabled us to estimate the concentration of the purified solution of fragment DRaIII/BamnHI of the alpha22 cDNA clone at 20 ng/µl.

The plasmid used to clone the DraIII/BamHI fragment of the alpha22 cDNA clone is the clone pUC18-fragment D clone digested by the DraIII and BamHI enzymes. This clone comprises an ampicillin-resistant gene.

500 ng of the plasmid pUC18-fragment D is subjected to digestion by the BamHI restriction endonuclease in a volume of 20 µl for 2 hours at 37° C. After digestion, 80 µl of TE buffer (10 mM Tris, 1 mM EDTA, pH 8) are added to the DNA solution which is extracted with one volume phenol/chloroform/isoamyl alcohol (ratio 50/48/2) cf. PREPARATION II1.

After centrifuging at 4° C. for 10 min at 12000 g, the DNA residue is washed in 1 ml ethanol 70, freeze dried and collected in 17 µl sterile milli-Q water. Digestion by DraIII is conducted for 2 hours at 37° C. in a final volume of 20 µl.

After digestion, 4 µl carrier buffer (30% sucrose, 0.25% bromophenol blue) are added to the mixture and analyzed on 0.8% Seaplaque GTG agarose gel (FMC, Rockland). The DNA band corresponding to pUC18-fragment D digested by DraIII and BamHI is collected and deposited in 350 µl of a solution of 20 mM Tris pH 8 and 1 mM EDTA pH 8. This sample is incubated for 5 min at 65° C., extracted with one volume of phenol ad centrifuged for 5 min at 10000 g. The aqueous phase is collected, extracted with one volume phenol/chloroform/isoamyl alcohol (ratio 50/48/2), cf. REPARATION II1.

After centrifuging at 4° C. for 10 min at 12000 g, the DNA residue is washed in 1 ml ethanol 70, freeze dried and collected in 20 µl sterile milli-Q water in order to obtain a 20 ng/ml solution of the plasmid pUC18-fragment D (DraIII/BamJI).

Ligation of fragment DraIII/BamHI of the alpha22 cDNA clone to the clone pUC18-fragment D (DraIII/BamHI) is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with ampicillin (50 µg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) following the manufacturer's instructions.

An aliquot (2 µl out of the 60 obtained) is subjected to enzymatic digestion by the XbaI and BamHI restriction endonucleases in order to verify cloning of fragment DraIII/BamHI of the alpha cDNA clone to the clone pUC18-fragment D (DraIII/BamHI). The XbaI restriction site is situated at 5' of the clone pUC18-fragment D. After electrophoresis, the gel is stained for 15 min in a 40 ng/ml solution of ethidium bromide, and the presence of the BamHI/XbaI fragment of 2336 bp is verified under UV illumination.

The sequencing reactions were made with the "T7 sequencing" kit (Pharmacia™) which uses the chain termination technique and T7 DNA polymerase which permitted validation of the integrity of the clone pUC18-fragment DE.

3/ Obtaining Fragments DEFG and DEFH

This stage consists of cloning the XbaI/BamHI fragment (nucleotides 474 to 2803) of 2329 bp of the clone pUC18-fragment DE between sites XbaI (of the pBluescript II SK(+) plasmid) and BamHI (of the FG or FH fragment) of the clone pBluescript II SK(+)-fragment FG or FH. This leads to obtaining clones pBluescript II SK(+)-fragment DEFG and pBluescript II SK(+)-fragment DEFH which comprise, between sites XbaI and HindIII, the sequence coding for amino acids 160 to 179 of the amino-telopeptide domain, the entire central helical region (amino acids 180 to 1192), the entire carboxy-propeptide domain (amino acids 1193 to 1464) of the human proα1 (I) chain, and the TAA stop codon coupled to the HindIII restriction site. In respect of the clone pBluescript II SK(+)-fragment DEFH, 4 specific codons of the KDEL sequence (Lys, Asp, Glu, Leu) are inserted between the sequence coding for the carboxy-propeptide domain and the TAA stop codon.

Cloning Fragment DE (XbaI/BamHI) With the BamHI/HindIII Part of Fragment FG or FH.

Approximately 1 g of the clone pUC18-fragment DE are digested by the BamHI restriction endonuclease for 90 min at 37° C.

Subsequent to enzymatic digestion, 80 μl of TE buffer (10 mM Tris, 1 mM EDTA, pH 8) are added to the DNA solution which is extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze dried and collected in 35 μl sterile milli-Q water. Digestion by XbaI is conducted for 2 hours at 37° C. in a final volume of 20 μl.

Subsequent to enzymatic digestion, 8 μl stop buffer (30% sucrose, 0.25% bromophenol blue) are added to the DNA solution which is analyzed by electrophoresis on 1% Seaplaque-GTG agarose gel (FMC, Rockland) with low melting point, cf. EXAMPLE I1.

The band corresponding to the XbaI/BamHI fragment of 2329 bp is cut under UV, deposited in 350 μl of a solution of 20 mM Tris pH 8 and 1 mM EDTA pH 8, and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2), cf PREPARATION II1.

After centrifuging at 4° C. for 10 min at 12000 g, the DNA residue is washed in 1 ml ethanol 70, freeze dried and collected in 20 μl sterile milli-Q water. An aliquot of 2 μl, together with 500 ng of the HindIII-EcoRI fragments of lambda phage (Promega™) are analyzed on 1% type II agarose gel (Sigma™), which enabled us to estimate the concentration of purified solution of the XbaI/BamHI fragment of clone pUC18-fragment DE at 20 ng/μl.

The plasmid used to clone the XbaI/BamHI fragment of the clone puC18-fragment DE is the clone pBluescript II SK(+)-fragment FG or FH digested by the enzymes XbaI and BamHI. This clone comprises an ampicillin-resistant gene.

500 ng of the plasmid pBluescript II SK(+)-fragment FG or FH are submitted to digestion by the BamHI restriction endonuclease for 2 hours at 37° C. After digestion, 80 μl TE buffer (10 mM Tris, 1 mM EDTA, pH 8) are added to the DNA solution which is extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze dried and collected in 17 μl sterile milli-Q water. Digestion by baI is conducted for 2 hours at 37° C.

After digestion, 4 μl carrier buffer (30% sucrose, 0.25% bromophenol blue) are added to the mixture and analyzed on 0.8% Seaplaque GTG agarose gel (FMC, Rockland). The DNA band corresponding to pBluescript II SK(+)-fragment FG or FH digested by XbaI and BamHI is collected and deposited in 350 μl of a solution of 20 mM Tris pH 8 and 1 mm EDTA pH 8. This sample is incubated for 5 min at 65° C., extracted with one volume of phenol and centrifuged for 5 min at 10000 g. The aqueous phase is collected, extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze-dried and collected in 20 μl sterile milli-Q water in order to obtain a 20 ng/ml solution of plasmid pBluescript II SK(+)-fragment FG or FH (XbaI/BamHI).

Ligation of the XbaI/BamHI fragment of the clone pUC18-fragment DE to the clone pBluescript II SK(+)-fragment FG or FH (XbaI/BamHI) is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with ampicillin (50 μg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) following the manufacturer's instructions.

An aliquot (2 μl out of the 60 obtained) is subjected to enzymatic digestion by the XbaI and HindIII restriction endonucleases in order to verify cloning of the XbaI/BamHI fragment of the clone pUC18-fragment DE to the clone pBluescipt II SK(+)-fragment FG or FH (BamHI/HindIII). After electrophoresis, the gel is stained for 15 min in a 40 ng/ml solution of ethidium bromide, and the presence of the XbaI/HindIII fragment of approximately 3900 bp is verified under UV illumination.

The sequencing reactions were conducted with the "T7 sequencing" kit (Pharmacia™) which uses the chain termination technique and T7 DNA polymerase and permitted validation of the integrity of the clones pBluescript II SK(+)-fragment DEFG and pBluescript II SK(+)-fragment DEFH.

4/ Obtaining Fragments ADEFG and ADEFH, Complete cDNA Clones Specific to the Human proα1 (I) Chain.

This stage consists of cloning the SacII/NehI fragment (nucleotides −4 to 479) of 495 bp of the clone pBluescript II SK(+)-fragment A between sites SacII (of plasmid pBluescript II SK(+)) and NheI (of fragment DEFG or DEFH) of the clone pBluescript II SK(+)-fragment DEFG or DEFH. This leads to obtaining clones pBluescript II SK(+)-fragment ADEFG and pBluescript II SK(+)-fragment ADEFH which comprise, between sites SacII and HindIII, the sequence coding for the entire human proα1 (I) chain, and the TAA stop codon coupled to the HindIII restriction site. Another HindIII site is localized just after the SacII site which will allow removal of fragments ADEFG and ADEFH by simple digestion with the HindIII restriction endonuclease. In respect of clone pBluescript II SK(+)-fragment ADEFH, 4 codons specific to the KDEL sequence (Lys, Asp, Glu, Leu) are inserted between the sequence coding for the carboxy-propeptide domain and the TAA stop codon. The NheI site leads to substitution of amino acids Asn and Phe by a lysine and a leucine at position 158 and 159 of the human proα1 (I) chain.

Cloning Fragment A (SacII/NehI) With the NheI/HindIII Part of Fragment DEFG or DEFH.

Approximately 1 μl of the clone pBluescript II SK(+)-fragment A are digested by the SacII restriction endonuclease for 90 min at 37° C.

Subsequent to enzymatic digestion, 80 μl of TE buffer (1I nM Tris, 1 mM EDTA, pH 8) are added to the DNA solution which is extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze dried and collected in 35 μl sterile milli-Q water. To this DNA solution are added 4 μl digestion B buffer (Promega™), 1 μl of the NheI restriction endonuclease (12 u/μl); Promega™). Digestion is conducted for 2 hours at 37° C.

Subsequent to enzymatic digestion, 8 μl stop buffer (30% sucrose, 0.25% bromophenol blue) are added to the DNA solution which is analyzed by electrophoresis on 2% NueSieve-GTG agarose gel with low melting point (FMC, Rockland) at a constant voltage of 60 volts. The electrophoresis buffer is 0.5×TBE (45 mM Tris borate, 1 mM EDTA (ethylenediaminetetra-acetic acid, pH 8). After migration the gel is stained for 15 min in a 0.5×TBE solution containing 40 ng/ml ethidium bromide.

The band corresponding to fragment SacII/NheI of 495 bp is cut under UV, deposited in 350 μl of a solution of 20 MM Tris pH 8, 1 mM EDTA pH 8, and incubated for 5 min at 65° C. After dissolution of the agarose, the sample is extracted with one volume phenol and centrifuged for 5 min at 10000 g. The aqueous phase is collected, extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze dried and collected in 20 μl sterile milli-Q water. An aliquot of 2 μl, together with 500 ng of the HindIII-EcoRI fragments of lambda phage (Promega™) are analyzed on 2% type II agarose gel (Sigma™), which enabled us to estimate the concentration of the purified solution of the SacII/NheI fragment of the clone pBluescript II SK(+)-fragment A at 5 ng/μl.

The plasmid used to clone the SacII/NheI fragment of the clone pBluescript II SK(+)-fragment A is the clone pBluescript II SK(+)-fragment DEFG or DEFH digested by the enzymes SacII and NheI. This clone comprises an ampicillin-resistant gene.

500 ng of the plasmid pBluescript II SK(+)-fragment DEFG or DEFH are submitted to digestion by the SacII restriction endonuclease in a volume of 20 μl for 2 hours at 37° C. After digestion, 80 μl TE buffer (10 mM Tris, 1 mM EDTA, pH 8) are added to the DNA solution which is extracted with one volume phenol/chloroform/isoamyl alcohol (ratio 50/48/2), cf PREPARATION II1.

After centrifuging at 4° C. for 10 min at 12000 g, the DNA residue is washed in 1 ml ethanol 70, freeze dried and collected in 17 μl sterile milli-Q water. Digestion with NhcI is conducted for 2 hours at 37° C.

After digestion, 4 μl carrier buffer (30% sucrose, 0.25% bromophenol blue) are added to the mixture and analyzed on 0.8% Seaplaque GTG agarose gel (FMC, Rockland), cf. PREPARATION II4. The DNA band corresponding to pBluescript II SK(+)-fragment DEFG or DEFH digested by SacII and NheI is collected and deposited in 350 μl of a solution of 20 mM Tris pH 8, 1 mM EDTA pH 8. This sample is incubated for 5 min at 65° C., extracted with one volume of phenol and centrifuged for 5 min at 10000 g. The aqueous phase is collected and extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze dried and collected in 20 μl sterile milli-Q water in order to obtain a 20 ng/ml solution of the plasmid pBluescript II SK(+)-fragment DEFG or DEFH (SacII/NehI).

Ligation of the SacII/NehI fragment of clone pBluescript II SK(+)-fragment A to the clone pBluescript II SK(+)-fragment DEFG or DEFH (SacII/NheI) is conducted for 4 hours at ambient temperature.

For transformation, the competent bacteria used are DH5-Alpha (Gibco BRL, Paris).

Several white colonies are tested. For testing, they are deposited individually in 3 ml L-Broth supplemented with ampicillin (50 μg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) following the manufacturer's instructions.

An aliquot (2 μl out of the 60 obtained) is subjected to enzymatic digestion by the HindIII restriction endonuclease in order to verify cloning of the SacII/HneI fragment of the clone pBluescript II SK(+)-fragment A to the clone pBluescript II SK(+)-fragment DEFG or DEFH (NheI/HindIII). Visualisation of a HindIII fragment of 4400 bp validates these clonings. After electrophoresis, the gel is stained for 15 min in a 40 ng/ml solution of ethidium bromide and the presence of the HindIII/HindIII fragment of 4400 bp is verified under UV.

The sequencing reactions were conducted with the "T7 sequencing kit" (Pharmacia™) which uses the chain termination technique and T7 DNA polymerase, and permitted validation of the integrity of clone pBluescript II SK(+)-fragment ADEFG and clone pBluescript II SK(+)-fragment ADEFH.

It is recalled that the clone pBluescript II SK(+)-fragment ADEFG comprises, between these two HindIII sites, the entirety of the sequence coding for the human proα1 (I) chain.

The clone pBluescript II SK(+)-fragment ADEFH comprises, between these two HindIII sites, the entirety of the sequence encoding the human proα1 (I) chain. Also, at the carboxy-terminal part of this chain it generates the retention sequence in the endoplasmic reticulum Lys-Asp-Glu-Leu.

5/ Obtaining Fragment BDEFG, cDNA Clone Coding for the PRS Plant Peptide Signal and the Entirety of the Human Proα1 (I) Chain With the Exception of the Amino-propeptide Domain.

This stage consists of cloning the SacII/NheI fragment (nucleotides −3 to 75) of 90 p of the clone pBluescript II SK(+)-fragment B between sites SacII (of the plasmid pBluescript II SK(+)) and NheI (of fragment DEFG) of the clone pBluescript II SK(+)-fragment DEFG. This leads to obtaining clone pBluescript II SK(+)-fragment BDEFG which comprises between sites SacII and HindIII the sequence coding for the plant PRS peptide signal, the entirety of the human proα1 (I) chain with the exception of the amino-propeptide domain, and the TAA stop codon coupled to the HindIII restriction site. Another HindIII site is localized just after the SacII site, which will enable removal of the BDEFG fragment by simple digestion with the HindIII restriction endonuclease. The NheI site leads to substitution of amino acids Glu and Gly by a leucine and an alanine at position 25 and 26 of the human proα1 (I) chain.

The plant PRS (Pathogenesis-Related Protein S) peptide signal replaces the peptide signal particular to the human proα1 (I) chain.

Cloning Fragment B (SacII/NheI) With the NheI/HindIII Part of Fragment DEFG

Approximately 2 μg of the clone pBluescript II SK(+)-fragment B are digested by the SacII restriction endonuclease for 90 min at 37° C.

Subsequent to enzymatic digestion, 80 μl of TE buffer (10 m M Tris, 1 mM EDTA, pH8) are added to the DNA solution which is extracted with one volume phenol/chloroform/ isoamyl alcohol (ratio 50/48/2), cf. PREPARATION II1.

After centrifuging at 4° C. for 10 min at 12000 g, the DNA residue is washed in 1 ml ethanol 70, freeze dried and collected in 34 µl sterile milli-Q water. Digestion by NhcI is conducted for 2 hours at 37° C.

Subsequent to enzymatic digestion, 8 µl stop buffer (30% sucrose, 0.25% bromophenol blue) are added to the DNA solution which is analyzed by electrophoresis on 2% NueSieve-GTG agarose gel (FMC, Rockland) with low melting point, cf PREPARATION II1.

The band corresponding to fragment SacII/NheI of 90 bp is cut under UV, deposited in 350 µl of a solution of 20 mM Tris pH8, 1 mM EDTA pH 8, and incubated for 5 min at 65° C. After dissolution of the agarose the sample is extracted with one volume of phenol and centrifuged for 5 min at 10000 g. The aqueous phase is collected, extracted with one volume phenol/chloroform/isoamyl alcohol (ratio 50/48/2), cf PREPARATION II1.

After centrifuging at 4° C. for 10 min at 12000 g, the DNA residue is washed in 1 ml ethanol 70, freeze dried and collected in 20 µl sterile milli-Q water. An aliquot of 2 µl, together with 500 ng of the HindIII-EcoRI fragments of lambda phage (Promega™) are analyzed on 2% type II agarose gel (Sigma™) which enabled us to estimate the concentration of the purified solution of the SacII/NheI fragment of the clone pBluescript II SK(+)-fragment B at 1 ng/µl.

The plasmid used to clone the SacI/HneI fragment of the clone pBluescript II SK(+)-fragment B is the clone pBluescript II SK(+)-fragment DEFG digested by the enzymes SacII and NheI. This clone comprises an ampicillin-resistant.

500 ng of the plasmid pBluescript II SK(+)-fragment DEFG is subjected to digestion by the SacII restriction endonuclease in a volume of 20 µl for 2 hours at 37° C. After digestion, 80 µl TE buffer (10 mM Tris, 1 mM EDTA, pH 8) are added to the DNA solution which is extracted with one volume phenol/chloroform/isoamyl alcohol (ratio 50/48/2), cf PREPARATION II1.

After centrifuging at 4° C. for 10 min at 12000 g, the DNA residue is washed in 1 ml ethanol 70, freeze dried and collected in 17 µl sterile milli-Q water. Digestion with NhcI is conducted for 2 hours at 37° C.

After digestion, 4 µl carrier buffer (30% sucrose, 0.25% bromophenol blue) are added to the mixture and analyzed on 0.8% Seaplaque GTG agarose gel (FMC, Rockland), cf. PREPARATION II4. The DNA band corresponding to pBluescript II SK(+)-fragment DEFG digested by SacII and NheI is collected and deposited in 350 µl of a solution of 20 mM Tris pH 8, 1 mM EDTA pH 8. This sample is incubated for 5 min at 65° C., extracted with one volume of phenol and centrifuged for 5 min at 10000 g. The aqueous phase is collected, extracted with one volume phenol/chloroform/ isoamyl alcohol (ratio 50/48/2), cf. PREPARATION II1.

After centrifuging at 4° C. for 10 min at 12000 g, the DNA residue is washed in 1 ml ethanol 70, freeze dried and collected in 20 µl sterile milli-Q water in order to obtain a 20 ng/ml solution of the plasmid pBluescript II SK(+)-fragment DEFG (SacII/NheI).

Ligation of the SacII/NheI fragment of clone pBluescript II SK(+)-fragment B to the clone pBluescript II SK(+)-fragment DEFG (SacII/NheI) is conducted for 4 hours at ambient temperature.

For transformation, the competent bacteria used are DH5-Alpha (Gibco BRL, Paris). Several white colonies are tested. For testing, they are deposited individually in 3 ml L-Broth supplemented with ampicillin (50 µg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) following the manufacturer's instructions.

An aliquot (2 µl out of the 60 obtained) is subjected to enzymatic digestion by the HindIII restriction endonuclease in order to verify cloning of fragment SacII/NehI of the clone pBluescript SK(+)-fragment B to the clone pBluescript II SK(+)-fragment DEFG (NheI/HindIII). Visualisation of a HindIII fragment of 4000 bp validates these clonings. After electrophoresis, the gel is stained for 15 min in a 40 ng/ml solution of ethidium bromide, and the presence of the HindIII/HindIII fragment of 4000 bp is verified under UV illumination.

The sequencing reactions were conducted with the "T7 sequencing" kit (Pharmacia™) which uses the chain termination technique and T7 DNA polymerase, and permitted validation of the integrity of the clone pBluescript II SK(+)-fragment BDEFG.

It is recalled that the clone pBluescript II SK(+)-fragment BDEFG comprises between these two HindIII sites the sequence coding for the plant PRS peptide signal and the entirety of the human proα1 (I) chain with the exception of the amino-propeptide domain.

Creation of the NheI site leads to substitution of amino acids Glu and Gly by a leucine and an alanine at position 25 and 26 of the human proα1 (I) chain.

6/ Obtaining Fragment BCDEFG, cDNA Clone Coding for the Plant PRS Peptide Signal and the Entirety of the Human proα1 (I) Chain This stage consists of cloning fragment NheI/NheI (nucleotides 72 to 479) of 402 bp of the clone pBluescript SK II(+)-fragment C into the NheI site (of fragment BDEGH) of the clone pBluescript II SK(+)-fragment BDEFG. This leads to obtaining the clone pBluescript II SK(+)-fragment BCDEFG which comprises between sites SacII and HindIII the sequence coding for the plant PRS peptide signal, the entirety of the human proα1 (I) chain and the TAA stop codon coupled to the HindIII restriction site.

Another HindIII site is localised just after the SacII site which will enable removal of fragment BCDEFG by simple digestion with the HindIII restriction endonuclease. The NnheI sites lead to substitution of amino acids Glu and Gly by a leucine and an alanine at position 25 and 26 of the human proα1 (I) chain, and substitution of amino acids Asn and Phe by a lysine and a leucine at position 158 and 159 of the human proα1 (I) chain.

The plant PRS peptide signal replaces the peptide signal particular to the human proα1 (I) chain.

Cloning Fragment C (NheI/NehI) Into the NehI Site of Fragment BDEFG

Approximately 1 µg of the clone pBluescript II SK(+)-fragment C are digested by the NheI restriction endonuclease for 90 min at 37° C.

Subsequent to enzymatic digestion, 4 µl stop buffer (30% sucrose, 0.25% bromophenol blue) are added to the DNA solution which is analysed by electrophoresis on 2% NueSieve-GTG agarose gel with low melting point (FMC, Rockland), cf. PREPARATION II1.

The band corresponding to fragment NheI/NheI of 402 bp is cut under UV, deposited in 350 µl of a solution of 20 mM Tris pH 8, 1 mM EDTA pH 8, and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2), cf. PREPARATION II1.

After centrifuging at 4° C. for 10 min at 12000 g the DNA residue is washed in 1 ml ethanol 70, freeze dried and collected in 20 μl sterile milli-Q water. An aliquot of 2 μl, together with 500 ng of the HindIII-EcoRI fragments of lambda phage (Promega™) are analysed on 2% type II agarose gel (Sigma™) which enabled us to estimate the concentration of the purified solution of the NheI/NheI fragment of the clone pBluescript II SK(+)-fragment C at 5 ng/μl.

The plasmid used to clone fragment NheI/NheI of the clone pBluescript II SK(+)-fragment C is the clone pBluescript II SK(+)-fragment BDEFG linearized by the enzyme NheI. This clone comprises an ampicillin-resistant gene.

250 ng of the plasmid pBluescript II SK(+)-fragment BDEFG is subjected to digestion by the NheI restriction endonuclease, in a volume of 20 μl for 2 hours at 37° C. After digestion, 80 μl TE buffer (10 mM Tris, 1 mM EDTA pH 8) are added to the DNA solution which is extracted with one volume phenol/chloroform/isoamyl alcohol (ratio 50/48/21), cf. PREPARATION II1.

After centrifuging at 4° C. for 10 min at 12000 g the DNA residue is washed in 1 ml ethanol 70, freeze dried and collected in 17 μl sterile milli-Q water. To this DNA solution are added 2 μl 10×buffer of calf intestine alkaline phosphatase (CIP, Promega™), 1 μl CIP (1 u/μl; Promega™). Dephosphorylation is conducted for 1 hour at 37° C. This stage will prevent self-ligation of this clone during the ligation stage.

After digestion, 80 μl TE buffer (10 mM Tris, 1 mM EDTA, pH 8) are added to the DNA solution which is extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze-dried and collected in 20 μl sterile milli-Q water in order to obtain a 10 ng/ml solution of the plasmid pBluescript SK II(+)-fragment BDEFG (HneI, dephosphorylated).

Ligation of fragment NheI/NheI of the clone pBluescript SK II(+)-fragment C to the clone pBluescript II SK(+)-fragment BDEFG (NheI, dephosphorylated) is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with ampicillin (50 μg/ml), and these cultures are incubated overnight under shaking at 37° C.

To purify the plasmid DNA, the culture is first centrifuged at 1500 g for 10 min at 4° C. and the bacterial residue is treated with the Wizard kit (Promega™) following the manufacturer's instructions.

An aliquot (2 μl out of the 60 obtained) is subjected to enzymatic digestion by the NheI restriction endonuclease in order to verify cloning of fragment NheI/NheI of the clone pBluescript II SK(+)-fragment C to the clone pBluescript II SK(+)-fragment BDEFG (NheI). Visualisation of a NheI fragment of 402 bp validates cloning. After electrophoresis, the gel is stained for 15 min in a 40 ng/ml solution of ethidium bromide and the presence of the NehI fragment of 402 bp is verified under UV illumination.

The sequencing reactions were conducted with the "T7 sequencing" kit (Pharmacia™) which uses the chain termination technique and T7 DNA polymerase, and permitted validation of the integrity of the clone pBluescript II SK(+)-fragment BCDEFG.

It is recalled that the clone pBluescript II SK(+)-fragment BCDEFG comprises between these two HindIII sites the sequence coding for the plant PRS peptide signal and the entirety of the human proα1 (I) chain.

Creation of the Nhe sites leads to substitution of amino acids Glu and Gly by a leucine and an alanine at position 25 and 26 of the human proα1 (1) chain, and substitution of amino acids Asn and Phe by a lysine and leucine at position 158 and 159 of the human proα1 (I) chain.

7/ Obtaining the 4 Constructs pBIOC21-recombinant Human Collagen.

Construction of the different plasmids via the use of recombinant DNA techniques is derived from pBIOC4. The binary plasmid is derived from pGA442 (An, 1986). The plasmid derived from pBIOC4 and containing the "PD35S-T35S" expression cassette is the plasmid pBIOC21.

The various elements permitting reproduction of these constructs are for example given in the description in patent application WO9633277 which is incorporated by reference.

Obtaining the four constructs pBIOC21-recombinant human collagen consisted of passing the 4 constructs of the plasmid pBluescript II SK(+) to the plasmid pBIOC21.

Plasmid pBIOC21 is used to allow expression of the recombinant collagen in the leaves and grains of tobacco or colza. It provides the following regulatory sequences:

a) the double constitutive promoter 35S (PD35S) of the Cauliflower Mosaic Virus (CaMV). It corresponds to duplication of the sequence activating transcription situated upstream from the TATA element of the natural 35S promoter.

b) the transcription terminator sequence, terminator polyA 35S, which corresponds to the 3' sequence non-coding for the sequence of the CaMV circular bicatenary DNA virus producing transcript 35S.

Cloning Fragments (HindIII/HindIII) of the pBluescript Constructs Into the HindIII Cloning Site of Vector pBIOC21.

Approximately 1 μg of the clone pBluescript II SK(+)-fragment ADEFG or ADEFH or BDEFG or BCDEFG are digested by the HindIII restriction endonuclease for 90 min at 37° C.

Subsequent to enzymatic digestion, 4 μl stop buffer (30% sucrose, 0.25% bromophenol blue) are added to the DNA solution which is analysed by electrophoresis on 0.8% Seaplaque-GTG agarose gel (FMC, Rockland) having a low melting point, cf. PREPARATION II4.

The band corresponding to fragment HindIII/HindIII of 4400 bp is cut under UV, deposited in 350 μl of a solution of 20 mM Tris pH 8, 1 mM EDTA pH 8, and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze dried and collected in 20 μl sterile milli-Q water. An aliquot of 2 μl, together with 500 ng of the HindIII-EcoRI fragments of lambda phage (Promega ™) are analysed on 0.8% type II agarose gel (Sigma™), which enabled us to estimate the concentration of the purified solution of fragment HindIII/HindIII of the clone pBluescript II SK(+)-fragment ADEFG or ADEFH or BDEFG or BCDEFG at 25 ng/μl.

The plasmid used to clone fragment HindIII/HindIII of the clone pBluescript II SK(+)-fragment ADEFG or ADEFH or BDEFG or BCDEFG is the clone pBIOC21 linearized by the HindIII enzyme. This clone comprises a tetracycline-resistant gene.

1 μg of the pBIOC21 plasmid is subjected to digestion by the HindIII restriction endonuclease, in a volume of 20 μl for 2 hours at 37° C. After digestion, 80 μl TE buffer (10 mM Tris, 1 mM EDTA, pH 8) are added to the DNA solution which is extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze dried and collected in 17 µl sterile milli-Q water. To this DNA solution is added 2 µl of 10×buffer of calf intestine alkaline phosphatase (CIP, Promega™), 1 µl CIP (1 u/µl; Promega™). Dephosphorylation is conducted for 1 hour at 37° C. This stage prevents self-ligation of this clone during the ligation stage.

After digestion, 80 µl TE buffer (10 mM Tris, 1 mM EDTA, pH 8) are added to the DNA solution which is extracted with one volume phenol/chloroform/isoamyl alcohol (ratio 50/48/2), cf. PREPARATION II1.

After centrifuging at 4° C. for 10 min at 12000 g, the DNA residue is washed in 1 ml ethanol 70, freeze dried and collected in 20 µl sterile milli-Q water in order to obtain a 40 ng/ml solution of the plasmid pBIOC21 (HindIII, dephosphorylated).

Ligation of fragment HindIII/HindIII of the clone pBluescript II SK(+)-fragment ADEFG or ADEFH or BDEFG or BCDEFG to the clone pBIOC21 (HindIII, dephosphorylated) is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with tetracycline (40 µg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) following the manufacturer's instructions. Approximately 1–2 µg of plasmid DNA is purified with this kit if the plasmid used is pBIOC21.

An aliquot (5 µl out of the 60 obtained) is subjected to enzymatic digestion by the KpnI restriction endonuclease in order to verify orientation of the cloning of fragment HindIII of the clone pBluescript II SK(+)-fragment ADEFG or ADEFH or BCDEFG to the clone pBIOC21 (HindIII). Visualisation of a KpnI fragment of 950 bp is specific to correct orientation. This KpnI fragment of 950 bp results from a KpnI restriction site at position 2.8 kb of vector pBIOC21 and from a KpnI site at position 137 of the sequence coding for the human pro[α1 (I) chain. After electrophoresis, the gel is stained for 15 min in a 40 ng/ml solution of ethidium bromide, and the presence of the KpnI fragment of 950 bp is verified under UV.

For construct pBIOC21-fragment BDEFG, we used the NheI enzyme and compared its digestion mode with vector pBIOC21-fragment BCDEFG digested by NheI. The only difference is the presence of a supernumerary NheI/NheI fragment for vector pBIOC21-fragment BCDEFG.

The sequencing reactions were conducted with the "T7 sequencing" kit (Pharmacia ™) which uses the chain termination technique and T7 DNA polymerase, and permitted validation of the integrity of the 4 pBIOC221 constructs made.

The sequences of the 4 constructs will now be given. In each case, the peptide signal of plant PRS or the human proα1 (I) chain are underlined, the substitutions of amino acids due to the creation of one or two NheI restriction sites are given in bold print as is the retention sequence in the endoplasmic reticulum KDEL. The amino- and carboxy-proteinase recognition sites are outlined.

The pBIOC21-collagen constructs obtained in this way (FIGS. 5 and 6) will be denoted hereafter:
pBIOC704 for the construct containing fragment ADEFG
pBIOC705 for the construct containing fragment ADEFH
pBIOC706 for the construct containing fragment BDEFG
pBIOC707 for the construct containing fragment BCDEFG The plasmid DNA of the binary plasmids pBIOC704, pBIOC705, pBIOC706 and pBIOC797 was inserted by direct transformation into strain LBA4404 of *Agrobacterium Tumerfaciens* using Holsters' method (1978). The validity of the clones selected is verified by enzymatic digestion of the inserted plasmid DNA.

Restoring Amino Acids Asn and Phe at Position 158 and 159 of the Human proα1 (I) Chain in Clones ADEFG, ADEFH and BCDEFG.

All these clones are included in the pBluescript II SK(+) vector (Stratagene™). The operation consists of exchanging the sequence lying between sites KpnI (bases 137 to 142) and DraIII (bases 1709 to 1720) of these constructs by the KpnI-DraIII sequence of the 1alpha3 cDNA clone. This operation leads to restoring amino acids 158 and 159 of the proα1 (I) chain (Asn and Phe). This operation was conducted since Morikawa (1980) showed that residue 159 (Phe) localised three amino acids upstream from the Pro-Gln cleavage site seemed to play an important role in the aminoproteinase cutting of the proα1 (I) chain.

1/ Elimination of the KpnI Restriction Site From the pUC18 Vector.

Vector pUC18 was used since it does not have an internal DraIII restriction site, unlike the pBluescript II SK(+) vector. Elimination of the KpnI restriction site will permit use of enzymes DraIII and KpnI with a view to exchanging the recombinant KpnI-DraIII fragments of clones ADEFG or ADEFH or BCDEFG for the wildtype fragment KpnI-DraIII of clone 1alpha3 cDNA.

For this purpose, 100 ng of pUC18 vector are digested by the KpnI restriction endonuclease (Promega™) following the manufacturer's instructions. The vector linearized into KpnI was then treated with the Mung Bean nuclease (Promega™) following the manufacturer's instructions in order to obtain a vector pUC18 KpnI with blunt ends. The ligation, transformation and sequencing stages of the clones obtained are conducted as described in the part concerning PREPARATION II.

2/ Transfer of Fragments ADEFG, ADEFH and BCDEFG Into the Vector pUC18 Minus KpnI.

For this purpose 200 g of the constructs pBluescript II SK(+)-ADEFG or ADEFH or BCDEFG are digested by the HindIII restriction endonuclease (Promega™) following the manufacturer's instructions.

Subsequent to enzymatic digestion, 4 µl stop buffer (30% sucrose, 0.25% bromophenol blue) are added to the DNA solution which is analysed by electrophoresis on 0.8% Seaplaque-GTG agarose gel (FMC,™) having a low melting point at a constant voltage of 60 volts. The electrophoresis buffer is 0.5×TBE (45 mM Tris borate, 1 mM EDTA (ethylenediaminetetra-acetic acid), pH 8). After migration the gel is stained for 15 min in a solution of 0.5×TBE containing 40 ng/ml ethidium bromide.

The band corresponding to fragment ADEFG or ADEFH or BCDEFG is cut under UV, deposited in 350 µl of a solution of 20 mM Tris pH 8, 1 mM EDTA pH 8, and incubated for 5 min at 65° C. After dissolution of the agarose, the sample is extracted with one volume of phenol and centrifuged for 5 min at 10000 g. The aqueous phase is collected, extracted with one volume phenol/chloroform/ isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2 M, and precipitated for 16 hours at −20° C. after addition of two volumes ethanol 100.

After centrifuging at 4° C. for 10 min at 12000 g, the DNA residue is washed in 1 ml ethanol 70, freeze dried and collected in 20 $\mu$l sterile milli-Q water. An aliquot of 2 $\mu$l, together with 500 ng of the HindIII-EcoRI fragments of lambda phage (Promega,™) are analysed on 0.8% type II agarose gel (Sigma™) which enabled us to estimate the concentration of the purified solution of fragment D BamHI/XbaI at 5 ng/$\mu$l.

The plasmid used to clone fragment HindIII of the clone pBluescript II SK(+)-fragment ADEFG or ADEFH or BCDEFG is the clone pUC18 minus KpnI linearized by the HindIII enzyme. This clone comprises an ampicillin-resistant gene.

250 ng of the plasmid pUC18minusKpnI are subjected to digestion by the HindIII restriction endonuclease following the manufacturer's instructions. Subsequent to this digestion the DNA is treated with calf intestine alkaline phosphatase (CIP, Promega™) following the manufacturer's instructions. This stage will prevent self ligation of this clone during the ligation stage.

After digestion, 80 $\mu$l of TE buffer (10 mM Tris, 1 mM EDTA, pH 8) are added to the DNA solution which is extracted with one volume phenol/chloroform/isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2 M and precipitated 16 hours at −20° C. after addition of two volumes ethanol 100.

After centrifuging at 4° C. for 10 min at 12000 g, the DNA residue is washed in 1 ml ethanol 70, freeze dried and collected in 20 $\mu$l sterile milli-Q water in order to obtain a 10 ng/ml solution of the plasmid pUC18minusKpnI (HindIII, dephosphorylated).

Ligation of fragment HindIII of the clone pBluescript II SK(+)-fragment ADEFG or ADEFH or BCDEFG to the vector pUC18 minusKpnI (HindIII, dephosphorylated) is conducted for 4 hours at ambient temperature.

For transformation, the competent bacteria used are DH5-Alpha (Gibco BRL, ™).

Several white colonies are tested. For testing, they are deposited individually in 3 ml L-Broth supplemented with ampicillin (50 $\mu$g/ml) and these cultures are incubated overnight under shaking at 37° C.

To purify the plasmid DNA, the culture is first centrifuged at 1500 g for 10 min at 4° C. and the bacterial residue is treated with the Wizard kit (Promega™) which permits purification of the supercoiled plasmid DNA. This manipulation is conducted following the manufacturer's instructions. Approximately 10 mg of plasmid DNA is purified with this kit if the plasmid used is pUC18.

An aliquot (2 $\mu$l out of the 60 obtained) is subjected to enzymatic digestion by the HindIII restriction endonuclease in order to verify cloning of the HindIII fragment of clone pBluescript II SK(+)-fragment ADEFG or ADEFH or BCDEFG to the clone pUC18minusKpnI(HindIII). After electrophoresis the gel is stained for 15 min in a 40 ng/ml solution of ethidium bromide, and the presence of the HindIII fragment of 4400 bp is verified under UV.

The sequencing reactions conducted with the "T7 sequencing" kit (Pharmacia™) which uses the chain termination technique and T7 DNA polymerase (cf. PREPARATION 1) permits validation of the integrity of cloning.

3/ Exchange of recombinant fragments KpnI-DraIII of clones ADEFG, ADEFH and BCDEFG by the wildtype fragment KpnI-DraIII of clone 1alpha3 cDNA.

For this purpose 500 ng of the clone 1alpha3 cDNA are digested by the restriction endonucleases KpnI(Promega™) and DraIII (Boehringer Mannheim) following the manufacturer's instructions.

Subsequent to enzymatic digestion 4 $\mu$l stop buffer (30% sucrose, 0.25% bromophenol blue) are added to the DNA solution which is analysed by electrophoresis on 0.8% Seaplaque-GTG agarose gel (FMC, Rockland™) having a low melting point at constant voltage of 60 volts. The electrophoresis buffer is 0.5×TBE (45 mM Tris borate, 1 mM EDTA (ethylenediaminetetra-acetic acid), pH 8). After migration the gel is stained for 15 min in a solution of 0.5×TBE containing 40 ng/ml of ethidium bromide.

The band corresponding to fragment KpnI-DraIII is cut under UV, deposited in 350 $\mu$l of a solution of 20 mM Tris pH 8, 1 mM EDTA pH 8 and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2 M and precipitated for 16 hours at −20° C. after addition of two volumes ethanol 100.

After centrifuging at 4° C. for 10 min at 12000 g, the DNA residue is washed in 1 ml ethanol 70, freeze dried and collected in 20 $\mu$l sterile milli-Q water. An aliquot of 2 $\mu$l and 500 ng of the HindIII-EcoRI fragments of lambda phage (Promega™) are analysed on 0.8% type II agarose gel (Sigma) which enabled us to estimate the concentration of the purified solution of fragment KpnI-DraIII of the 1alpha3 cDNA clone at 5 mg/$\mu$l.

The plasmid used to clone fragment KpnI-DraIII of clone 1alpha3 cDNA is the clone pUC18minusKpnI-fragment ADEFG or ADEFH or BCDEFG digested by enzymes KpnI-DraIII. This clone comprises an ampicillin-resistant gene.

250 ng of the plasmid pUC18 minusKpnI-fragment ADEFG or ADEFH or BCDEFG is subjected to digestion by restriction endonucleases KnpI and DraIII following the manufacturer's instructions.

Subsequent to enzymatic digestion, 4 III stop buffer (30% sucrose, 0.25% bromophenol blue) are added to the DNA solution which is analysed by electrophoresis of 0.8% SeaPlaque-GTG agarose gel (FMC,™) having a low melting point at a constant voltage of 60 volts. The electrophoresis buffer is 0.5×TBE (45 mM Tris borate, 1 mM EDTA (ethylenediaminetetra-acetic acid), pH8).

After migration, the gel is stained for 15 min in a solution of 0.5×TBE containing 40 ng/ml ethidium bromide.

The band corresponding to the vector pUC18 minusKpnI-fragment ADEFG or ADEFH or BCDEFG KpnI-DraIII is cut under WV, deposited in 350 $\mu$l of a solution of 20 mM Tris pH 8, 1 mM EDTA pH 8 and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2M and precipitated for 16 hours at −20° C. after addition of two volumes ethanol 100.

After centrifuging at 4° C. for 10 min at 12000 g the DNA residue is washed in 1 ml ethanol 70, freeze dried and collected in 20 µl sterile milli-Q water. An aliquot of 2 µl, and 500 ng of the HindIII-EcoRI fragments of lambda phage (Promega™) are analysed on 0.8% type II agarose gel (Sigma) which enabled us to estimate the concentration of the purified solution of the vector pUC18 minusKpnI-fragment ADEFG or ADEFH or BCDEFG KpnI-DraIII at 8 ng/µl.

Ligation of fragment KpnI-DraIII of the 1alpha3 cDNA clone to the vector pUC18 minusKpnI-fragment ADEFG or ADEFH or BCDEFG KpnI-DraIII is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with ampicillin (50 µg/ml) and these cultures are incubated overnight under shaking at 37° C.

To purify the plasmid DNA, the culture is first centrifuged at 1500 g for 10 min at 4° C. and the bacterial residue is treated with the Wizard kit (Promega, ™) which permits purification of the supercoiled plasmid DNA. This manipulation is conducted following the manufacturer's instructions. Approximately 10 µg plasmid DNA is purified with this kit if the plasmid used is pUC18.

An aliquot (2 µl out of the 60 obtained) is subjected to enzymatic digestion by the NehI restriction endonuclease in order to verify cloning of fragment KpnI-DraII of clone 1alpha33 cDNA to the clone pUC18 minusKpnI-fragment ADEFG or ADEFH or BCDEFG KpnI-DraIII. Exchange of recombinant fragment KpnI-DraIII by the wildtype fragment leads to elimination of a NheI restriction site. After electrophoresis, the gel is stained for 15 min in a 40 ng/ml solution of ethidium bromide, and elimination of the NheI restriction site is verified under UV illumination.

The sequencing reactions conducted with the "T7 sequencing" kit (Pharmacia™) which uses the chain termination technique and T7 DNA polymerase (cf. REPARATION 1) permits validation of cloning integrity.

The fragments obtained are ADEFGphe159, ADEFHphe159 and BCDEFGphe159.

4/ Obtaining Constructs pBIOC21-Recombinant Human Collagen phe159.

This stage consists of passing the 3 constructs of plasmid pUC18 minusKpnI to plasmid pBIOC21.

Plasmid pBIOC21 is used to enable expression of recombinant collagen in the leaves of tobacco or colza. It provides the following regulatory sequences:
 a) the double-35S constitutive promoter (PD35S) of CaMV. This corresponds to duplication of the sequence activating transcription upstream from the TAT element of the natural 35S promoter.
 b) the transcription terminator sequence, terminator polyA 35S, which corresponds to the 3' sequence non-coding for the sequence of the circular bicatenary DNA cauliflower mosaic virus producing transcript 35S.

Construction of the different plasmids via the use of recombinant DNA techniques is derived from pBIOC4. The binary plasmid derives from pGA442 (AN, 1986). The plasmid derived from pBIOC4 and containing the "PD35S-TS5S" expression cassette is plasmid pBIOC21.

The various elements permitting reproduction of these constructs are for example contained in the description in patent application WO9633277 which is incorporated by reference.

Cloning of Fragments (HindIII/HindIII) of Bonstructs pUC18 Minus KpnI Into the HindIII Cloning Site of the pBIOC21 Vector.

Approximately 1 µg of the clone pUC18 minusKpnI-fragment ADEFGphe159, ADEFHphe159 or BCDEFG-phe159 are digested by the HindIII restriction endonuclease following the manufacturer's instructions.

Subsequent to enzymatic digestion, 4 µl stop buffer (30% sucrose, 0.25% bromophenol blue) are added to the DNA solution which is analysed by electrophoresis on 0.8% SeaPlaque-GTG agarose gel having a low melting point (FMC, Rockland) at a constant voltage of 60 volts. The electrophoresis buffer is 0.5×TBE (45 mM Tris borate, 1 mM EDTA (ethylenediaminetetra-acetic acid, pH 8). After migration the gel is stained for 15 min in a solution of 0.5×TBE containing 40 ng/ml ethidium bromide.

The band corresponding to fragment HindIII/HindIII of 4400 bp is cut under UV, deposited in 350 µl of a solution of 20 mM Tris pH8, 1 mM EDTA pH8 and incubated for 5 min at 65° C. After dissolution of the agarose, the sample is extracted with one volume of phenol and centrifuged for 5 min at 10000 g. The aqueous phase is collected, extracted with one volume phenol/chloroform/isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2 M, and precipitated for 16 hours at −20° C. after addition of two volumes ethanol 100.

After centrifuging at 4° C. for 10 min at 12000 g, the DNA residue is washed in 1 ml ethanol 70, freeze dried and collected in 20 µl sterile milli-Q water. An aliquot of 2 µl, and 500 ng of the HindIII-EcoRI fragments of lambda phage (Promega, ™) are analysed on 0.8% type II agarose gel (Sigma™), which enabled us to estimate the concentration of the purified solution of fragment HindIII/HindIII of clone pUC18 minusKpnI-fragment ADEFGphe 159 or ADEFH159 or BCDEFGphe159 at 25 ng/µl.

The plasmid used to clone fragment HindIII/HindIII of clone pUC18minusKpnI-fragment ADEFGphe 159 or ADEFHphe159 or BCDEFGphe159 is the pBIOC21 clone linearized by the HindIII enzyme. This clone comprises a tetracycline-resistant gene.

1 µg of plasmid pBIOC21 is subjected to digestion by the HindIII restriction endonuclease. This digestion is conducted in a volume of 20 µl in the presence of 2 µl B buffer (Promega, ™), 1 µl HindIII enzyme (12 u/µl; Promega™) for 2 hours at 37° C. After digestion, 80 µl TE buffer (10 mM Tris, 1 mM EDTA pH 8) are added to the DNA solution which is extracted with one volume phenol/chloroform/isoamyl alcohol (ratio 50/48/2) and centrifuged for 2 min at 10000 g. The aqueous phase is extracted with chloroform/isoamyl alcohol (ratio 42/1) and centrifuged for a few second at 10000 g. The aqueous phase is collected, adjusted to a final NaCl concentration of 0.2 M and precipitated for 16 hours at −20° C. after addition of two volumes ethanol 100.

After centrifuging at 4° C. for 10 min at 12000 g, the DNA residue is washed in 1 ml ethanol 70, freeze dried and collected in 17 µl sterile milli-Q water. To this DNA solution are added 2 µl 10×buffer of calf intestine alkaline phosphatase (CIP, Promega, ™), 1 µl CIP (1 u/µl; Promega, ™). Dephosphorylation is conducted for 1 hour at 37° C. This stage prevents self-ligation of this clone during the ligation stage.

After digestion, 80 µl TE buffer (10 mM Tris, 1 mM EDTA, pH 8) are added to the DNA solution which is extracted with one volume phenol/chloroform/isoamyl alcohol (ratio 50/48/2) and centrifuged for 2 min at 10000 g. The aqueous phase is extracted with chloroform/isoamyl alcohol (ratio 24/1) and centrifuged for a few seconds at 10000 g. The aqueous phase is collected, adjusted to a final NaCl concentration of 0.2 M and precipitated for 16 hours at −20° C. after addition of two volumes ethanol 100.

After centrifuging at 4° C. for 10 min at 12000 g, the DNA residue is washed in 1 ml ethanol 70, freeze dried and collected in 20 µl sterile milli-Q water in order to obtain a 40 ng/ml solution of the plasmid pBIOC21 (HindIII, dephosphorylated).

Ligation of fragment HindIII/HindIII of the clone pUC18minusKpnI-fragment ADEFGphe159 or ADEFHphe159 or BCDEFGphe159 to the clone pBIOC21 (HindIII, dephosphorylated) is conducted for 4 hours at room temperature.

For transformation, the competent bacteria used are DH5-Alpha (Gibco BRL, Paris).

Several white colonies are tested. For testing, they are deposited individually in 3 ml L-Broth supplemented with tetracycline (40 pg/ml), and these cultures are incubated overnight under shaking at 37° C.

To purify the plasmid DNA, the culture is first centrifuged at 1500 g for 10 min at 4° C., and the bacterial residue is treated with the Wizard kit (Promega™) which permits purification of the supercoiled plasmid DNA. This manipulation is conducted following the manufacturer's instructions. Approximately 1–2 µg plasmid DAN can be purified with this kit if the plasmid used is pBIOC21.

An aliquot (5 µl out of the 60 obtained) is subjected to enzymatic digestion by the KpnI restriction endonuclease in order to verify the cloning orientation of the HindIII fragment of clone pUC18minusKpnI-fragment ADEFGphe159 or ADEFHphe159 or BCDEFGphe159 to the clone pBIOC21 (HindIII). Detection of a KpnI fragment of 950 bp is specific to proper orientation. This KpnI fragment of 950 bp results from a KpnI restriction site at position 2.8 kb of the vector pBIOC21 and from a KpnI site at position 137 of the sequence coding for the human proα1 (I) chain. After electrophoresis, the gel is stained for 15 min in a 40 ng/ml solution of ethidium bromide, and the presence of the KpnI fragment of 950 bp is verified under UV illumination.

The sequencing reactions conducted with the "T7 sequencing" kit (Pharmacia™) which uses the chain termination technique and T7 DNA polymerase (cf. PREPARATION I) permits validation of cloning integrity.

The pBIOC21-collagen constructs obtained in this way shall be designated as follows:

pBIOC708 for the construct containing the fragment ADEFGphe159 pBIOC709 for the construct containing fragment ADEFHphe159, pBIOC710 for the construct containing fragment BCDEFHphe159.

EXAMPLE 2

Construction of Chimeric Genes Coding for the Recombinant Protein of Human Collagen and Permitting Expression in Maize Seeds.

Constitutive expression in maize seeds of the cDNA coding for the human collagen pro-[α1 (I) chain required the following regulatory sequences 1. the maize zein gene promoter (Pzein) contained in plasmid p63. This permits expression in the albumin of maize seeds;

2. the transcription terminator sequence, terminator polyA NOS, which corresponds to the 3' region non-coding for the nopaline synthase gene of the Ti plasmid of *Agrobacterium tumefaciens*, nopaline strain.

The different elements which permit the reproduction of these constructs are for example contained in the description in patent application WO909633277 which is incorporated by reference.

Fragments ADEFG, ADEFH, BDEFG and BCDEFG were isolated from the plasmids by digestion with HindIII, purified by electrophoresis on 0.8% agarose gel, electroeluted, subjected to alcohol precipitation and dried. These DNA fragments were then treated with the Klenow enzyme (New England Biolabs™) following the manufacturer's instructions, subjected to phenol-chloroform extraction, alcohol precipitation and collected in 10 µl H20.

The p63 plasmid was double digested by SacI and BamHI, purified by electrophoresis on 0.8% agarose gel, electroeluted, subjected to alcohol precipitation and dried. It was then treated with the T4 polymerase enzyme (New England Biolabs™) and dephosphorylated with calf intestine alkaline phosphatase enzyme (Boehringer Mannheim) following the manufacturer's instructions.

Each ADEFG, ADEFH, BDEFG and BCDEFG fragment obtained as described above was ligated to plasmid p63 treated as described above.

Ligation and transformation of the competent *Escherichia coli* bacteria, strain DH5a were conducted using standard methods. The plasmids obtained are denoted pBIOC700, pBIOC701, pBIOC702 and pBIOC703 respectively, and respectively contain fragments ADEFG, ADEFH, BDEFG and BCDEFG.

Amino acids Asn and Phe at positions 158 and 159 of the human proα1 (I) chain were restored into clones ADEFG, ADEFH and BCDEFG to obtain ADEFGphe159, ADEFHphe159 and BCDEFHphe159 respectively. This modification is described in example 1.

Fragments ADEFGphe159, ADEFHphe159 and BCDEFHphe159 were isolated from the plasmids by digestion with HindIII, purified by electrophoresis on 0.8% agarose gel, electroeluted, subjected to alcohol precipitation and collected in 10 µl H20. The fragments thus prepared were ligated to plasmid p63 treated as described above. The plasmids obtained are denoted pBIOC711, pBIOC712 and pBIOC713, and respectively contain fragments ADEFGphe159, ADEFHphe159 and BCDEFHphe159.

EXAMPLE 3

Obtaining Transgenic Colza Plants

Grains of Spring rape (Brassica napus cv WESTAR or Limagrain lines) are disinfected for 40 minutes in a 15% Domestos™ solution. After rinsing 4 times in sterile water, the grains are left to germinate, 20 grains per pot 7 cm in diameter and 10 cm high, on Murashige and Skoog mineral medium (Sigma M 5519) with 30 g/l sucrose and solidified with 5 g/l agargel. These pots are placed in a culture chamber at 26° C. with a photoperiod of 16 h/8 h under a light intensity in the region of 80 µE m$^{-2}$ After germinating for 5 days, the cotyledons are collected in sterile manner, cutting each petiole approximately 1 mm above the cotyledon node.

At the same time a preculture of *Agrobacterium tumefaciens* strain LBA4404 containing the plasmids is grown in a 50 ml erlenmeyer tube for 36 h at 28° C. in 10 ml 2YT bacterium medium supplemented with antibiotics appropriate for the selection of the strain used.

This preculture is used for 1% seeding of a new bacterial culture made under the same conditions. After 14 h the culture is centrifuged for 15 min at 3000 g and the bacteria are collected in an equivalent volume of liquid germination medium. This suspension is spread into petri dishes 5 cm in diameter to a density of 5 ml/dish.

The cut end of the petiole is immersed for a few seconds in the solution of agrobacteria prepared in this way, then the petiole is planted a few millimetres deep into the regeneration medium. This medium has the same basic composition as the germination medium with, in addition, 4 mg/l of benzyl-amino-purine (BAP) a phytohormone which promotes bud neoformation. Ten explants (cotyledon with petiole) are cultured per Petri dish 9 cm in diameter.

After 2 days' co-culture under the same environmental conditions as for germination, the explants are replanted into phytatrays (Sigma reference P1552) containing the preceding medium supplemented with a selective agent: 45 mg/l kanamycine sulfate (Sigma, reference K4000) and a bacteriostatic: mixture of 1/6 (by weight) of potassium salt of clavulanic acid and 5/6 sodium salt of amoxicillin (injectable Augmentin™) to 600 mg/l.

The explants are replanted two consecutive times at a 3-week interval in sterile manner in a fresh medium under the same conditions.

The green buds which appear at the end of the second or third replanting are separated from the explant and cultured separately in transparent pots 5 cm in diameter and 10 cm high containing an identical medium to the previous one but without BAP. After 3 week's culture, the stalk of the transformed bud is cut and the bud is replanted in a pot of fresh medium. After three to four weeks, the roots have sufficiently developed to allow acclimatisation of the seedling in a phytotron. Any buds that are not green or have not taken root are removed. These seedlings are then transplanted into square pots with 7 cm sides filled with compost soil (NF standard U4451: 40% brown peat: 30% sifted heath-mould: 30% sand) saturated in water. After two weeks' phytotron acclimatisation (temperature 21° C., photoperiod 16 h/8 h and 84% relative humidity) the seedlings are transferred to pots 12 cm in diameter filled with the same compost soil enriched with slow release fertiliser and transferred to a greenhouse (class S2) regulated at 18° C. with two daily water sprinklings lasting 2 minutes.

As soon as the flowers appear they are packed in sachets such as to prevent cross-fertilisation.

When the siliquae reach maturity they are harvested, dried and threshed. The grains obtained are used to titre biochemical activity. Selection of transgenic descent is made by germination on a medium containing kanamycine sulfate to the proportion of 100 to 150 mg/l (according to genotype). Operating conditions are identical to those described above except that germination is conducted in glass tubes with a single grain per tube. Only those seedlings which develop secondary roots during the first three weeks are acclimatised in a phytotron before being transferred to a greenhouse.

EXAMPLE 4

Obtaining Transgenic Tobacco Plants

The tobacco plants used for transformation experiments (*Nicotiana tabacum* var. *Xanthi* NC and PBD6) are cultured in vitro in a Marashige and Skoog basic medium (1962) supplemented with vitamins described by Gamborg et al. (1968, Sigma reference M0404), 20 g/l sucrose and 8 g/l agar. The pH of the medium is adjusted to 5.8 with a potash solution before autoclaving at 120° C. for 20 min. Inter-node cuttings are taken from the tobacco plants every 30 days and planted in this MS20 proliferation medium.

All in vitro cultures are conducted in an air-conditioned enclosure under the following conditions:
light intensity of 30 $\mu$E·m$^{-2}$,s$^{-1}$; photoperiod of 16 h;
thermnoperiod of 26° C. during the daytime, 24° C. at night.

The transformation technique used is derived from that described by Holsters et al. (1985).

A preculture of *Agrobacterium tumefaciens*, LBA4404 strain, containing the plasmids is made for 48 h at 28° C. under stirring in an LB medium supplemented with appropriate antibiotics (rifampicin and tetracycline). The preculture is then diluted to 1/50 in the same medium and cultured under the same conditions. After one night, the culture is centrifuged (10 min., 3000 g), the bacteria are recovered in an equivalent volume of liquid MS30 medium (30 g/l sucrose) and this suspension is diluted to 1/10.

Explants of approximately 1 cm$^2$ are cut from the leaves of the above-described seedlings. They are then placed in contact with the bacterial suspension for 1 h, quickly dried on filter paper and placed on a co-culture medium (solid MS30).

After 2 days, the explants are transferred to Petri dishes on the MS30 regeneration medium, containing a selective agent, kanamycine (200 mg/l), a bacteriostatic, augmentin (400 mg/l) and the hormones necessary for bud induction (BAP, 1 mg/l and ANA, 0.1 mg/l). The explants are replanted onto the same medium after 2 weeks' culture. After 2 additional weeks, the buds are replanted into Petri dishes on a development medium made up of MS20 medium supplemented with kanamycine and augmentin. After 15 days, one half of the buds are transplanted. Root growth requires approximately 20 days after which the seedlings can be cloned by inter-node propagation or transferred to a greenhouse.

EXAMPLE 5

Obtaining Transgenic Maize Plants

Obtaining Transgenic Maize Plants a) Obtaining Maize Calli and Their use as a Target for Genetic Transformation.

The genetic transformation of maize, irrespective of the method used (electroporation, Agrobacterium, microfibres, particle gun) generally requires the use of fast division undifferentiated cells which have maintained the ability to regenerate full plants. This type of cell makes up the friable embryogenous callus (so-called type II) of maize.

These calli are obtained from immature embryo of genotype HI II or (A188×B73) using the method and media described by Armstrong (1994). The calli obtained in this way are multiplied and maintained by successive transplanting every fifteen days onto the initiation medium.

Seedlings are then regenerated from these calli by modifying the hormonal and osmotic equilibrium of,the cells in accordance with the method described by Vain et al. (1989). These plants are then acclimatised in a greenhouse where they can be cross-bred or self-fertilised.

b) Use of a Particle Gun for the Genetic Transformation of Maize

The preceding paragraph describes how to obtain and regenerate the cell lines needed for transformation; here a genetic transformation method is described leading to stable incorporation of the modified genes into the plant genome.

This method is based on the use of a particle gun; the target cells are callus fragments described in paragraph 1. These fragments with a surface area of 10 to 20 mm$^2$ were deposited, 4 h before bombardment, in the centre of a Petri dish, 16 fragments per dish, containing a culture medium identical to the initiation medium supplemented with 0.2 M mannitol+0.2 M sorbitol. The plasmids carrying the genes to be incorporated are purified on a Qiagen™ column following the manufacturer's instructions. They are then precipitated onto tungsten particles (M10) according to the protocol described by Klein (1987 327:70–73). The particles coated in this way are gun sprayed onto the target cells.

The bombarded callus dishes are sealed and cultured in the dark at 27° C. The first transplanting is made 24 h later, and then every fifteen days for 3 months onto an identical medium to the initiation medium supplemented with a selective agent whose type and concentration may vary according to the gene used (see paragraph 3). Suitable selective agents are generally active compounds of some herbicides (Basta®, Round-up®) or certain antibiotics (Hydromycine, Kanamycine . . . ).

After 3 months, and sometimes earlier, calli are obtained whose growth is not inhibited by the selection agent, and are usually and chiefly made up of cells resulting from the division of a cell having incorporated into its genetic inheritance one or more copies of the selection gene. The incidence rate of obtaining such calli is approximately 0.8 callus per bombarded dish.

These calli are identified, individualised, amplified, then cultured such as to regenerate seedlings (cf. paragraph a). In order to avoid any interference with non-transformed cells, all these operations are conducted on culture media containing the selective agent.

The plants regenerated in this manner are acclimatised and cultured in a greenhouse where they can be cross-bred or self-fertilised.

EXAMPLE 6

EXTRACTION AND SCREENING

Extraction From Tobacco Plants That are Genetically Transformed in Accordance With the Invention 45 plants numbered 1 to 22 at the time of transfection with the pBIOC707 construct (comprising the N-propeptide, the major triple coil and the C-propeptide) and from 23 to 45 at the time of transfection with the pBIOC706 construct (comprising the major triple coil and the C-propeptide) are cut and weighed and frozen in liquid nitrogen. The different plants are then crushed in liquid nitrogen using a homogenizer for 2 min in order to obtain a fine powder, then stored until required for use at −20° C.

Extraction With Acetic Acid

The powder obtained for each plant, including non-transformed control plants, is collected in a 0.5 M solution of acetic acid containing 200 mM NaCl and protease inhibitors: 1 mM phenyl methyl sulfonide (PMSF), 1 mM N-ethyl maleimide (NEM), 2.5 mM ethylenediaminetetra-acetic acid (EDTA) to a proportion of 1 gram of powder per 4 ml of solution. The mixture is shaken at 4° C. for 60 hours. After centrifuging each sample at 20000 g(12148 rotor, Sigma™) for 30 minutes at 4° C., the residues are washed twice in distilled water and stored at −20° C. An aliquot (100 μl) of the supernatants is collected to conduct protein titration on the total extract. The remaining supernatants are stored at −20° C.

Protein Titration of the Total Extract

The collected aliquots of 100 μl for the acid-soluble extract and 20 μl for the neutral buffer extract are titrated using a ready prepared Coomassie solution. Titration is conducted in multi-well trays and results are read using a plate reader (SLT Lab Instruments, Austria) at a wavelength of 620 nm. A template range is made with a 100 μg/ml BSA solution from 0 to 10 μg/well: 0,10, 20, 30, 40, 50, 60, 70, 80, 90, 100 μl are deposited in each well and completed if necessary to a final volume of 100 μl. The different samples are also deposited in the wells and completed if necessary to 100 μl in the extraction buffer. References are made per 100 μl distilled water for the template range and per 100 μl extraction buffer for the samples. 100 μl of reagent are then added to each well and the values read immediately. The values obtained for each reference are respectively deducted from the values obtained for the template range and those of samples. A template curve is plotted and the protein concentration of the samples is deduced from this tracing.

Screening of Positives

Screening is Conducted in Two Manners:

1. Plant screening (after crushing and extraction) by gel electrophoresis followed by immunotransfer. The control collagen used is collagen I extracted from human or bovine tissue with acetic acid and purified by salt precipitation. The molecular form of collagen I that is most widely found in tissues is the heterotrimer containing two chains α1 and α2: [α1 (1) 2α2 (I). In this case the chain of interest α1 migrates slightly above 116 KDa, it only contains the major triple coil and the telopeptides; the N and C-propeptides were cleaved during maturation of the collagen and are therefore no longer present.

2. Screening of positives by indirect immunofluorescence on frozen sections of the different plants.

In both cases, the antibody used is a polyclonal antibody made in rabbit specific to collagen I; it recognises human and bovine collagen I and chains α1 (I) and α2 (I) indifferently (reference 20121, Institut Pasteur, Lyon). Another antibody may also be used: a Sp1D8 monoclonal antibody (Hybridoma Bank, USA) directed against the cleavage site of the type I N-propeptide. These two antibodies may be used on denatured collagen I (after gel electrophoresis and protein transfer) and on native collagen (by immunofluorescence).

1. Screening After Electrophoresis Analysis of Plants Followed by Immunotransfer Analytical Method Screening is made on the acetic acid extracts. The supernatants and residues are analysed.

Electrophoresis

500 μl of supernatants, i.e. 15 to 25 μg of total proteins, are precipitated by the addition of 50 μl 100% trichloroacetic acid for 30 minutes at room temperature. The samples are centrifuged at 20000 g for 15 minutes at 4° C., the residues washed twice in 100% cold ethanol. The precipitates are collected in 20 μl carrier buffer (60 mM Tris-Hcl, pH 6.8) containing 2% sodium dodecyl sulfate, 10% glycerol, 0.002% bromophenol blue) in the presence of final 10 mM dithiothreitol (DTT) reducing agent, then denatured for 3 minutes at 100° C.

The Residues

The residues, washed in distilled water to prevent the presence of acid and salts derived from the extraction buffer, are collected in 50 μl distilled water, 10 μl of the suspension are collected to which are added 20 μl carrier buffer concentrated 3 times (180 mM Tris-Hcl pH 6.8 containing 6% sodium dodecyl sulfate, 30% glycerol, 0.006% bromophneol blue) in the presence of final 10 mM dithiothreitol (DTT) reducing agent, then denatured for 3 minutes at 100° C.

The different samples are deposited on 6% acrylamide gel in a solution of 0.4 M Tris-HCl pH 8.8 containing 0.1% sodium dodecyl sulfate with a 4% concentration gel in a solution of 0.4% Tris-HCl pH 6.8 containing 0.1% sodium dodecyl sulfate. On each gel three wells are reserved respectively for the standard molecular weights (6H Sigma™), control collagen I (bovine or human, 3 μg/well) and the sample corresponding to the non-transformed plant. Migration takes place in a migration buffer of 0.025 M Tris-0.2 μlycine containing 0.1% sodium dodecyl sulfate under a voltage of 100 volts in the concentration gel, increased to 200 volts for the separation gel.

Immunotransfer:

After migration, the gels are spotted on a poly(vinylidene difluoride) membrane (Immobilon-P, Millipore™) previously moistened with 100% methanol then soaked in the CAPS transfer buffer (10 mM cyclohexylamino-1-propanesulfonic acid, pH 11, 5% methanol). The gel and membrane are placed in a transfer apparatus (Biorad™) and subjected to a voltage of 60 volts for 16 hours, cooled by a cold water circulation system.

To verify transfer efficiency, the gels are stained blue with Coomassie R-250 (0.2% solution in 40% methanol and 10% acid) for 30 minutes. They are then selectively discoloured in a solution of 15% methanol and 7.5% acetic acid and those proteins that are not or only partially transferred are detected by the presence of bands remaining on the gel. Also, the membranes are stained with Ponceau S (0.2% in 1% acetic acid) for 10 minutes then discoloured in distilled water. The different proteins that are properly transferred are detected, the lane corresponding to molecular weight standards is excised, air dried and stored between two sheets of filter paper. The remainder of the membranes is entirely discoloured.

The membranes are then saturated for one hour in 10% skimmed milk powder then quickly rinsed in 25 mM Tris-HCl pH 7.4, 150 mM NaCl, 2.5 mM KCl (TBS). The membranes are subsequently incubated with the polyclonal antibodies directed against the major triple coil of bovine collagen I made in rabbit diluted to 1:400 in TBS buffer containing 0.05% Tween 20 (TTBS), 1% bovine serum albumin for 2 hours at room temperature. After incubating with the antibodies the membranes are rinsed 6 times for 5 minutes in TTBS, then incubated with the conjugate diluted to 1:2000 (anti-IgC of rabbit made in pig, coupled to alkaline phosphatase (Dako™, Denmark) for 1 hour at room temperature. The membranes are again rinsed in TTBS (6 times 5 minutes) then developed with APColor kit reagents (Biorad™). The lanes having one or more bands with the expected molecular weights correspond to the positives, and the corresponding plant numbers are recorded. All the positives are subjected to a second screening (gel+ immunotransfer).

Results:

pBIOC706

The pBIOC706 construct has 40% positives in the form of a major band migrating at the level of the control α1 (I) chain. This result suggests that the C-propeptide (approximately 30 KDa) of the recombinant α1 (I) chain has been cleaved. The lanes corresponding to the non-transformed control plant show no band developed by the anti-collagen I antibody.

plants 23, 25, 28, 32, 36, 38, 39, 40, 45 are identified as positive, plants 40 and 45 are determined as being the most productive through their presence in the supernatants and their abundance in the residues.

pBIOC707

Figure 2:
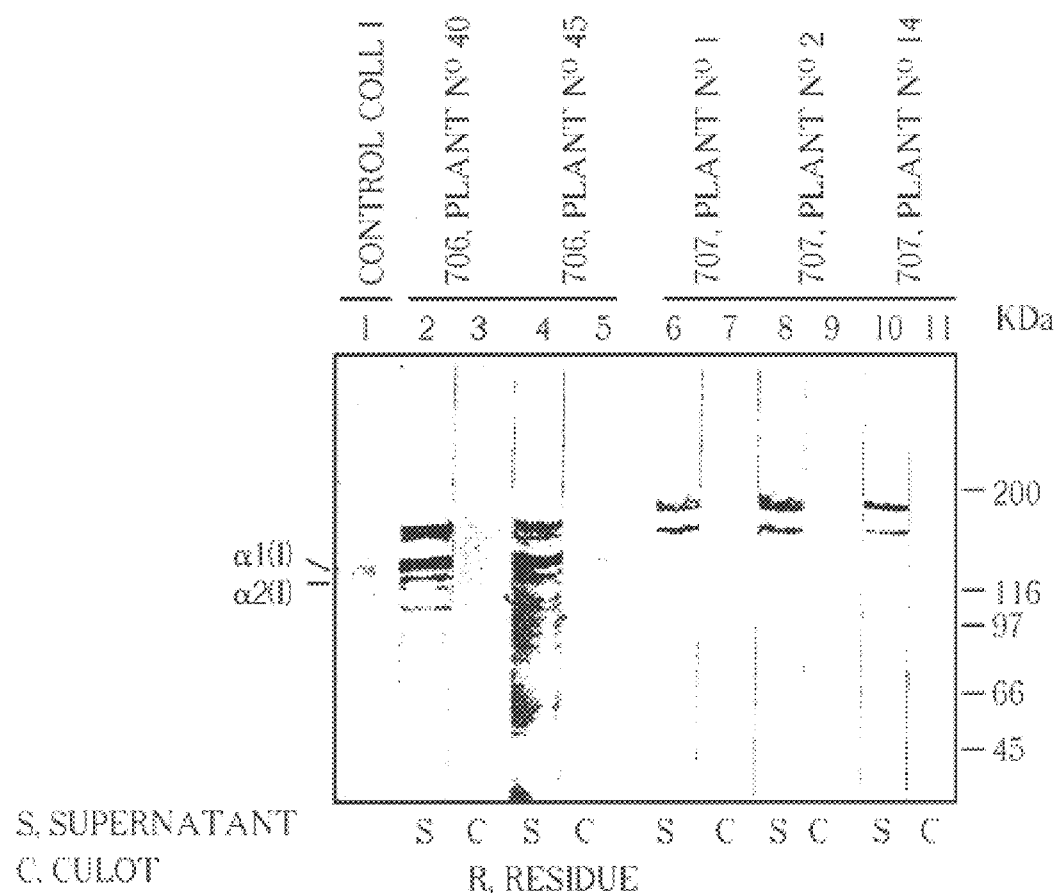

The pBIOC707 construct shows 27% positives in the form of a major band migrating above the control alpha1 (I) chain corresponding to a molecular weight of approximately 140 KDa. The expected molecular mass for the entire recombinant chain being approximately 160 KDa, this result suggests that the N-propeptide (approximately 20 KDa) or C-propeptide (approximately 30 KDa) of the recombinant α1 (I) chain has been cleaved. The lanes corresponding to the non-transformed control plant show no band developed by the anti-collagen I antibody.

plants 1, 2, 14, 16, 17, 19 are identified as positive, plants 1, 2 and 14 are determined as being the most productive through their presence in the supernatants and abundance in the residues (FIG. 2).

2. Immunofluorescence

Analytical Method

The plant leaves are coated in a cold inclusion medium (Tissue-Tek, Miles, USA) and frozen on the cryostat platinum cooled to −30° C.

Histological slides treated with aminoalkylsilane are prepared using the following method:

Immersion in a 2% solution of 3-aminopropyltriethoxy-silanel in acetone, for 5 seconds Washing in acetone, 2×1 minute Washing in distilled water Drying overnight at 42° C.

Freezing 7 μm sections are taken of all plants using a cryostat and deposited on the treated slides. The slides are then treated as follows Rinsing the slides in a phosphate buffer (PBS for phosphate buffer saline, 137 mM NaCl, 2.7 mM KCl, 10 mM sodium phosphate, pH 7.2).

blocking aspecific sites by incubation of the slides in PBS containing 1% bovine serum albumin (BSA), Incubation in the anti-collagen I antibodies (reference 20121, Institut Pasteur, Lyon) diluted to 1:50 in 1% PBS-BSA for 2 hours at room temperature. Control slides are made in which the anti-collagen I antibodies are replaced by PBS alone or by a polyclonal antibody specific to collagen IV.

Rinsing in PBS, 3 times 10 minutes,

Incubation in the conjugate (rabbit anti-IgG made in goat coupled to fluoresceine isothiocyanate (Biosys TM, France) diluted to 1:300 in 1% PBS-BSA for 1 h at room temperature. During incubation and up until the time of observation, the slides are placed in the dark.

Rinsing with PBS, 3 times 10 minutes

Treatment of the slides with 0.3% Eriochrome Black T in PBS to mask autofluorescence of the samples, for 1 minute;

Vigorous rinsing in PBS

Mounting cover glasses on slides with one drop of PBS-glycerol 1:1.

Slide observation is made using an epifluroescence Zeiss™ Universal microscope fitted with the Zeiss™ filter exciter BP 430–490.

Results

Slide observation enabled us to draw the following conclusions:

the clusters formed by the chloroplasts autofluorescence to red but do not hinder observation of the yellowish-green fluorescence of the positive plants, Yellowish-green autofluorescence is also observed on particular plant structures that are well delimited (channels).

The positive plants are however easily identifiable through the presence of small highly coloured clusters in the cells. In the plants corresponding to construct pBIOC706 (α1+C-pro) is also seen a diffuse filamentous network which appears to be localized in the extracellular part of the leaf Perfect correspondence is noted between the positive plants determined by the gel+transfer method and by immunofluorescence especially for those most positive, that is to say 1, 2, 14, 40 and 45.

Extraction in Neutral buffer:

In order to improve extraction, extraction in a neutral medium is also used for tissue collagen and procollagen (collagen molecule still containing N- and C-propeptides) is conducted on the residues of the positives from the preceding extraction: 1, 2, 14, 40 and 45.

The residues derived from extraction in an acid medium of each plant including non-transformed control plants are washed in distilled water two times before being collected in a buffer of 50 mM Tris-Hcl pH 7.4 containing 150 mM NaCt and protease inhibitors: 1 mM phenyl methyl sulfonide (PMSF), 1 mM N-ethyl maleimide (NEM), 2.5 mM ethylenediaminetetra-acetic acid (EDTA) to the proportion of 1 gram initial powder per 4 ml of solution. The mixture is shaken at 4° C. for 60 hours. After centrifuging each sample at 20000 g (rotor 12148, Sigma™) for 30 minutes at 4° C., the residues are washed 2 times in distilled water and stored at −20° C. An aliquot of the supernatants (20 µl) is collected to carry out protein titration on the total extract. The remainder of the supernatants is stored at −20° C.

Analytical Method cf. above

Results

1. Lanes Corresponding to the Plants Transformed With Construct pBIOC706:

For plants 40 and 45 the major band observed in the supernatants after extraction in an acid medium is found migrating at the α1 chain of control collagen I, but also another band of equal intensity migrating at approximately 140 KDa. This result indicates the presence of a complete recombinant α1 (I) chain corresponding to the pBIOC706 construct, since the upper band corresponds to the expected molecular mass for the recombinant α1 (I) chain comprising the C-propeptide.

2. Lanes Corresponding to the Plants Transformed With the Construct pBIOC707:

For each plant (1, 2 and 14) the major band observed in the supernatants after extraction in an acid medium is found migrating at approximately 140 KDa, but another band of equal intensity is also found migrating at approximately 160 KDa. This result indicates the presence of a complete recombinant α1 (I) chain for construct pBIOC707, since the upper band corresponds to the expected molecular mass for the recombinant α1 (I) chain comprising the N- and C-propeptides.

Figure 3:
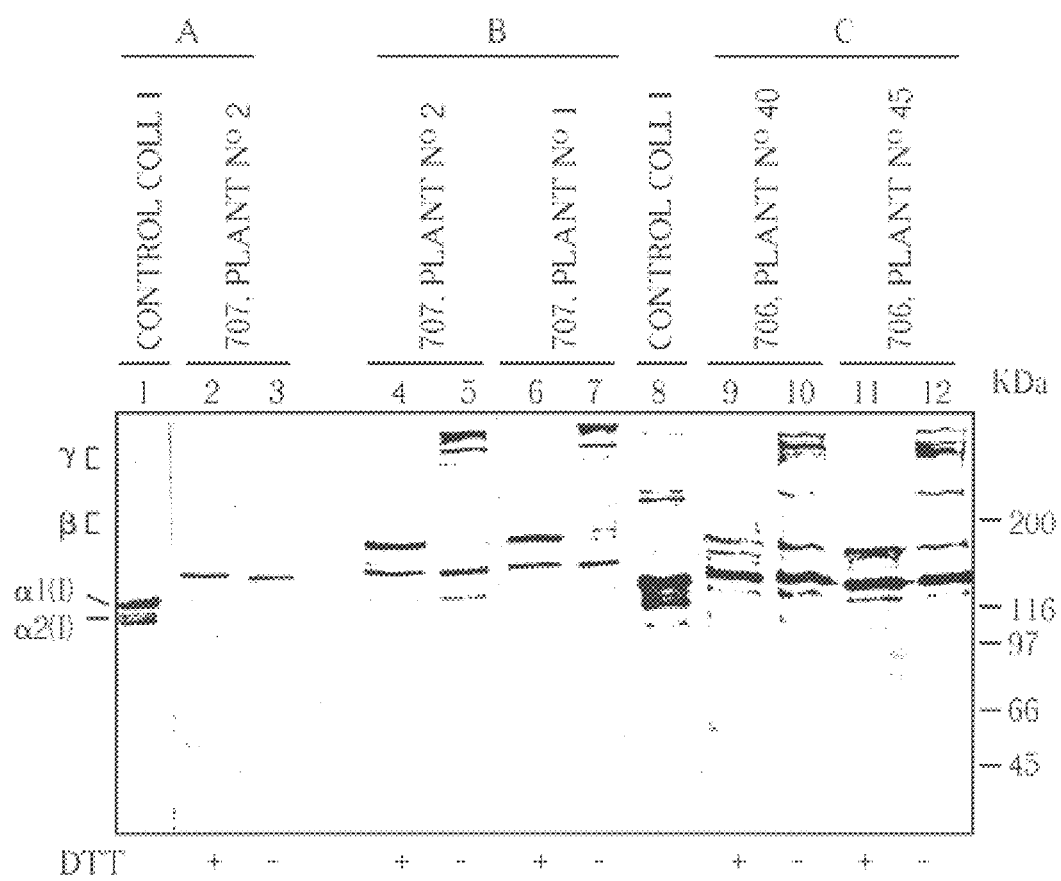

For the two constructs pBIOC706 and pBIOC707, the lanes corresponding to the residues after extraction and centrifuging of the samples no longer show any lane developed by the anti-collagen I antibody, demonstrating the efficiency of extraction in a neutral pH (FIG. 3).

EXAMPLE 7

COLLAGEN CONFORMITY

Determination of the presence of the N- and C-terminal Propeptides in the Recombinant α1 (I) Chains Extracted in an Acid Medium Extraction of the plants transformed with the pBIOC707 construct in an acid medium only permits extraction of a single band migrating slightly above the control α1 (I) band. The expected molecular mass for the entire recombinant polypeptide being 160 KDa, the assumption of cleaving during maturation of the recombinant α1 (I) chain is a considered possibility. The same applies to construct pBIOC706 for which a major band is observed at the level of control band α1 (I). This migration can only be attributed to cleavage of part of the recombinant chain. To give support to our assumption that the major bands obtained for constructs pBIOC706 and pBIOC707 correspond to the recombinant α1 (I) chains whose C-propeptide may have been cleaved during the production of the collagen chains, gel electrophoresis in the presence or absence of a reducing medium is conducted on a positive plant of each construct and analysed after immunotransfer. Since the N-propeptide, if it is properly folded, comprises intrachain bonding between the cysteines, whereas the cysteines of the C-propeptide are interchain bonded, a process which initiates the formation of the triple coil.

Analytical Method

Two 500 µl aliquots of plant 2 (positive of construct pBIOC707) and 40 (positive of pBIOC706 construct) are precipitated with the addition of 50 µl 100% trichloroacetic acid (TCA) for 30 minutes at room temperature. The samples are centrifuged at 20000 g for 15 minutes at 4° C. (rotor 12148, Sigma™), the residues are washed twice in cold 100% ethanol. The precipitates are then collected in 20 µl carrier buffer (60 mM Tris-HCl pH 6.8 containing 2% sodium dodecyl sulfate, 10% glycerol, 0.002% bromophenol blue) by alternating a lane in the presence of final 10 mM DTT and a lane without DTT, then denatured for 3 minutes at 100° C. The gels are analysed after immunotransfer.

After transfer and development with the anti-collagen I antibodies (reference 20121, Institut Pasteur, Lyon) it is observed that the recombinant chain of plant 2 migrates in the presence of a reducing agent slightly more slowly than the recombinant chain in the absence of a reducing agent. This slight difference in migration is not observed in the recombinant chain of plant 40 (N-propeptide deleted construct). It is deduced that this difference in migration is due to the correct folding of the N-propeptide permitting intrachain bonding of the cysteines. The C-propeptide is therefore apparently absent from the two recombinant polypeptides (FIG. 3, part A).

Presence of Interchain Bonding Between the Cysteines of the C-propeptide

Gel electrophoresis in the presence or absence of a reducing agent is conducted on samples extracted in a neutral pH for which two major bands are obtained of which the upper band must comprise the C-propeptide. This upper band migrates at the molecular mass expected for the non-cleaved polypeptide whether in respect of construct pBIOC706 (major triple coil +C-propeptide) or pBIOC707 (N-propeptide+major triple coil+C-propeptide), that is to say at 140 KDa and 160 KDa respectively. For bonding between the cysteines of three chains, a necessary stage for initiation of the formation of the triple coil, migration of the non-reduced upper band should migrate at the level of bands γ of the control collagen I corresponding to migration of three non-dissociated chains (approximately 300 KDa).

Analytical Method

Tests were conducted on plants 1, 2 and 14 (construct pBIOC707) and plants 40 and 45 (construct pBIOC706)

extracted in a neutral buffer. 2 times 150 μl of each sample, that is to say 7.5 μg to 11 μg of total proteins per test sample, are collected and precipitated with 15 μl 100% trichloroacetic acid (TCA) as described previously. A sample series is then collected in 20 μl carrier buffer in the absence of a reducing agent, the other series in 20 μl carrier buffer in the presence of 10 mM DTT. On each gel two wells are respectively reserved for standard molecular weights (6H Sigma ™), control collagen I (bovine or human, 3 μg/well). Migration takes place in a migration buffer (0.025 M Tris–0.2 M glycine) containing 0.1% sodium dodecyl sulfate under a voltage of 100 volts in the concentration gel, increased to 200 volts for the separation gel.

Immunotransfer:

Cf. above under Screening through plant analysis by electrophoresis followed by immunotransfer.

Results

1. Lanes Corresponding to the Plants Transformed With Construct pBIOC707:

In the presence of the reducing agent, for each plant 1, 2 and 14 two major bands are found one migrating in the region of 140 KDa, the other in the region of 160 KDa. In the absence of a reducing agent, the band at 140 KDa migrates slightly faster (intrachain bonding of the cysteines contained in the N-pro giving it a more compact structure and therefore migrating faster in the gel than the non-folded reduced form). The band at 160 KDa in the absence of a reducing agent disappears and a major band appears migrating in the region of 300 KDa (slightly above bands γ of control collagen I). This result indicates the presence of interchain bonding between the cysteines of the C-propeptide of the recombinant α1 (I) chain (FIG. 4 part B).

2. Lanes Corresponding to the Plants Transformed With Construct pBIOC706:

In the presence of the reducing agent, for plants 40 and 45 two major bands are found, one migrating at the α1 chain of the control collagen I, the other in the region of 140 KDa. In the absence of reducing agent, migration of the lower band is not modified (confirming the absence of the C-propeptide). The band at 140 KDa in the absence of a reducing agent partly disappears and a major band appears migrating in the region of 300 KDa (at the γ bands of the control collagen I). This result indicates the presence of interchain bonding between the cysteines of the C-propeptide of the recombinant α1 (I) chain (FIG. 4 part C).

EXAMPLE 8

Formation of the Triple Coil

Proteolytic Digestion

Careful digestion with trypsin or pepsin can indicate the formation of a triple coil and therefore of the homotrimer [α1 (I) 3, since the N and C-terminal ends are sensitive to proteases whereas the central part of the molecule, when the triple coil is formed, is resistant. Digestion conditions are chosen allowing digestion of the denatured collagen I without impairing native collagen I. The samples extracted in a neutral medium are digested by trypsin with an enzyme-substrate ratio of 1:20 at 25° C. for 10 minutes. The reaction is halted through the addition of 10% final TCA followed by two washings in cold 100% ethanol. The samples are collected in sample buffer containing 10 mM DTT, heated to 100° C. for 3 minutes and deposited on 6% electrophoresis gel. The gels are stained with Coomassie's blue or immunotransferred and developed by anti-collagen I antibodies (reference 20121, Institut Pasteur, Lyon) as described previously. The plants for which the triple coil was formed will permit observation of a single band migrating at the control α1 (I) chain.

Triple coil formation may also be demonstrated by use of pepsin. In this case, the samples are dialysed against 0.5 M acetic acid, 200 mM NaCl, pH 2/5, then subjected to pepsin digestion. The digestion conditions used are those which permit complete digestion of the denatured control collagen I. The reaction is halted by neutralising the digestion medium. The samples are then precipitated with 10% final TCA and treated as described above.

Digestion with proteases may also be used to determine the denaturing temperature of recombinant collagen and therefore the stability of the triple coil formed in the plants. In this case the samples are digested by trypsin at increasing reaction temperatures (from 25° C. to 45° C.) then treated as described above. The onset of bands corresponding to proteolytic degradation indicates the denaturing temperature of recombinant collagen. The temperature of native collagen is 41° C.; that of the recombinant α1 (I) homotrimer made in eukaryotic cells is similar to that of control collagen I but nonetheless the homotrimer is partly cleaved on and after a temperature of 38° C. (Geddis et al., 1993).

After trypsin digestion of the collagen extracted from the plants transformed with constructs pBIOC707 and pBIOC706 as described previously, a band is seen to persist migrating at the α1 (I) chain of control collagen I. This result demonstrates that the homotrimeric collagen extracted from the transformed plants is folded into a triple coil (FIG. 1, part A).

Shade Rotation

Formation of the triple coil can also be demonstrated by observation under a transmission electron microscope of replicas of molecules obtained after shade rotation. This is possible because the collagen molecule, when it is folded into a triple coil, has the characteristic shape of a rod 300 nm in length and 1.4 nm in diameter. Only the chains α1 (I) cannot be identified by this technique. The samples at a concentration of 10 to 20 μg/ml are dialysed against 200 mM ammonium bicarbonate overnight at 4° C. then mixed to a ratio of 1:1 with glycerol. 5 μl are deposited on a freshly split mica sheet 1 cm² in size, then placed in an evaporator (Med 10, Balzers™. Approximately 2 nm of platinum-carbon are evaporated over the samples at an angle of 8° under a vacuum of $2.10^{-6}$ Torr, followed by carbon evaporation at 90° for a few seconds. The replicas are detached by penetration of the micas at 45° in a container of filtered distilled water and they are assembled onto electron microscope grids (600 mesh size, copper). Observation is made under a transmission microscope (CM120, Philipps™).

Formation of a triple coil was confirmed by observations under electron microscope of collagen purified from positive plants after shade rotation. The molecules observed have the characteristic shape of rods 300 nm in length (FIG. 6 part B). The absence will be noted of a globular domain at one of the 2 ends of the triple coil confirming cleavage of the C-propeptide.

EXAMPLE 9

Ultrastructure of the Transformed Plants

A leaf fragment of each positive transformed plant and of a non-transformed control are fixed in a fixing mixture of 2% glutaraldehyde, 0.5% paraformaldehyde in a 0.1 M citrate-phosphate buffer for 8 hours at room temperature. During fixation and subsequently if required, the samples are placed under a vacuum bell for degasing. The samples are rinsed in the citrate-phosphate buffer with several 15 minute baths then post-fixed in a 2% osmic acid solution in the 0.1 M citrate-phosphate buffer for 2 hours at room temperature. The samples are then dehydrated with successive ethanol baths from 30° to 100°. The absolute ethanol is replaced by a bath of pure propylene oxide renewed twice. Substitution is made in baths containing a mixture of pure propylene oxide and Epoxy resin to the proportion of 1 volume per 3 volumes respectively, then 1:1 and finally 3:1. Impregnation is made in the pure Epoxy resin overnight and may be continued by changing the baths until complete immersion of the samples. The samples are then inserted in the capsules and left to polymerise for 3 days at 60° C. Ultrafine sections are taken, contrasted with 7% uranyl acetate in methanol for 10 minutes then with lead citrate for 5 minutes. Observations are made under a transmission electron microscope (CM120, Philipps™).

EXAMPLE 10

Purification of the Recombinant Collagen

The recombinant collagen is purified from plant extracts using its particular physico-chemical properties. The acid causes precipitation of many proteins and the electrophoretic tracings obtained from the extraction of control plants in an acid medium show that few endogenous proteins are extracted. Also, chlorophyll is not present in these extracts. Since collagen is soluble in acid, the different extracts are dialysed against 0.5 M acetic acid when they are not directly extracted in an acid medium. After centrifuging to remove insoluble material, the collagen is purified by fraction precipitation with salts in an acid medium: at 0.7 M NaCl in 0.5 M acetic acid, then after centrifuging the supernatant is filtered, precipitated with 0.9 NaCl in 0.5 M acetic acid, again centrifuged to obtain the precipitate in the residue. The 0.7 and 0.9 M precipitates containing the sample are collected in 0.5 M acetic acid then subjected to electrophoresis on 6% acrylamide. Purity of the fractions is estimated after staining the gels with Coomassie's blue. For those samples estimated to be insufficiently pure, a second precipitation cycle with salts may be conducted after dialysis of the fraction against 0.5 M acetic acid to remove residual salt traces. Should an additional purification stage be required, an ion exchange column is used with a NaCl gradient of 0 to 0.5 M for elution. The fractions are then subjected to gel electrophoresis as described previously.

Results show that most of the plant proteins are eliminated by a precipitation stage with 0.4 M NaCl. After precipitation with 0.7 M followed by 0.9 M NaCl as indicated in example 10, the homotrimeric collagen is observed to be 80–90% pure in the 0.9 M NaCl precipitate.

A heparin bonding site situated on heterotrimeric collagen has been described in the literature (San Antonio et al., 1994, J. Cell Biol., 125:1179–1188). Such sites are responsible for the fixation of proteoglycanns present in the extracellular matrix, but also for cell adhesion via receptors of membrane proteoglycann type. These interactions therefore ensure cohesion of the collagen network. Persistence of this site on the homotrimer is analysed by fixing the homotrimer on a heparin affinity column under physiological conditions of pH (7.4) and ion strength (0.15 M NaCl). This method can serve as a second purification stage.

EXAMPLE 11

Amino Acid Composition and Microsequencing

The different products obtained after extraction of transformed plants are vacuum hydrolysed with 6N HCl at 115° C. for 24 hours in a PicoTag system (Waters, ™). The amino acid composition is determined using an automatic Beckman™ analyser. With this analysis it is possible in particular to verify the level of hydroxylated proline, as proline hydroxylation guarantees the stability of the triple coil.

Microsequencing is conducted using Edman's method with apparatus permitting automatic N-terminal sequencing of proteins (Applied Biosystems 473 A protein sequencer™). The recombinant collagens or procollagens may be loaded into the apparatus in 2 manners:

after purification, the protein is in the form of a concentrated solution.

The protein is fixed by hydrophobic bonds on a fibreglass pellet treated with polybrene. The glass pellet is placed directly in the apparatus.

after electrophoresis and electrotransfer, the bands of interest are identified after staining with 0.02% Ponceau's red in 0.1% acetic acid and discolouring with filtered distilled water, cut with a scalpel and then placed in a cell appropriate for the apparatus.

According to the principle of Edman's method, each cycle releases an amino acid in the form of a phenylthiohydantoine-amino acid complex. They are successively and automatically injected into the high pressure chromatography column (HPLC) in reverse phase and detected by UV absorbency at 269 nm. By comparison between their retention times and standard spectra, it is possible to determine cycle per cycle the N-terminal sequence of the analysed protein.

The collagen obtained by precipitation with 0.9 M NaCl is subjected to an additional purification stage (reverse phase chromatographic column (C8) HPLC) before proceeding with amino acid analysis. The analysis obtained conforms to the above-described analysis with cDNA of the human α1 (I) chain, in particular for the characteristic residues of collagen, Glycine and Proline

| Glycine | (Pro + OHPro) | Proline |
| --- | --- | --- |
| α1 (I) predicted cDNA | 32.8% | 22.7% |
| α1 (I) extracted from plants | 28.4% | 20.6% |

Also, to verify whether cleavage of the plant peptide signal present in constructs pBIOC707 and pBIOC706 occurred properly, and to ensure also that no proteolytic degradation occurred at the N-terminal end during extraction, each of the lower bands observed on electrophoresis gel for the collagen extracted from plants transformed with constructs pBIOC707 and pBIOC706 was subjected to N-terminal sequencing by Edman degradation after electrotransfer.

The sequences obtained are: ELAPQLSY (SEQ. ID. NO.: 19) for the collagen corresponding to construct pBIOC706 and AQVEGQDE (SEQ. ID. NO.: 20) for construct pBIOC707. These results show that cleavage of the peptide signal did actually occur and also confirm that the N-terminal ends (the N-telopeptide for construct pBIOC706 and the N-propeptide for construct pBIOC707) are intact. Also, all results (examples 6, 7, 8 and 11) show that the collagen extracted from mature plants corresponds to a homotrimeric collagen whose C-propeptide is cleaved.

EXAMPLE 12

Accumulation of Collagen in Mature Plants

The young, transformed plants which proved to be positive by immunotransfer were brought to maturity. The plant leaves were picked and either directly frozen and cold crushed, or freeze dried. Irrespective of the storage method used for the leaves (freezing or freeze drying) the collagen is easily extracted in an acid medium using the conditions described in example 6. After extraction, a single major band is found for each of the extracts obtained from the plants transformed with constructs pBIOC707 and pBIOC706. In each case this band corresponds to the homotrimer after cleaving of the C-propeptide (see example 6). Furthermore, it is shown that the collagen can accumulate in mature plants and thereby generate a substantial quantity of collagen per gram of fresh weight. A young plant (plant 45 for example) can provide an extract containing approximately 6–8 μg/ml of homotrimeric collagen, whereas on reaching maturity the same plant can allow extraction of 40–50 μg/ml, i.e. 0.5 mg/g fresh weight. The collagen molecule containing the N- and C-propeptides is called procollagen, and the name pN-collagen and pC-collagen is given to those molecules containing either one of the terminal domains. Finally the collagen is in the molecular form which only contains the triple coil domain and corresponds in animal tissue to the mature form. Consequently, the extracted products are identified as pN-collagen (construct pBIOC707) and collagen (construct pBIOC706).

EXAMPLE 13

Fibrillogenesis and Adhesion Test

The purified collagen is diluted to 0.2–0.5 mg/ml in 0.1 M acetic acid, then dialysed against a phosphate buffer saline (PBS), pH 7.4 at 4° C. overnight. The sample is then placed in a waterbath and the temperature progressively increased up to 30° C. and stabilised at this temperature for 2 hours. The formation of fibres is observed under an electron microscope after negative or positive staining of the samples. Fibre formation kinetics is observed by turbidimetry using a spectrophotometer, since fibre formation modifies optic density (Wood and Keech, 1960, Biochem. J., 75:588–598).

Collagen I is an adhesive protein, that is to say that numerous cell types are able to recognise it and to fix themselves on it in specific manner via membrane receptors. It is possible to test the adhesive properties of a protein using a microplate colorimetric test (Aumailley et al., 1989, Exp. Cell Res. 181,463–474).

The extracted collagen is adsorbed overnight at 4° C. on multi-well trays then placed in contact with a cell suspension at 37° C. for 20 to 30 minutes. The non-adherent cells are removed by washing, the adherent cells are fixed with 1% glutaraldehyde, then stained with 0.1% crystal violet. After vigorous washing of the trays, the colouring agent fixed by the adherent cells is solubilised in X100 Triton. The trays are read off using a ELISA reader at 570 nm, the optic density value relates to the number of adherent cells.

BIBLIOGRAPHICAL REFERENCES

Armstrong et al., (Maize Handbook; (1994) M. Freeling, V. Walbot Eds.; pp. 665–671).
An et al., Plant Physiol, 81, 301–305 (1986)
Anderson O. I. and Greene F. C., T.A.G., 77, 689–700 (1989).
Barta et al., Plant Mol. Biol., 6, 347–357 (1986).
Bednarek et al., Plant cell 3, 1195–1206 (1991).
Cornelissen et al., Nature, 321, 531–532 (1986).
Depigny-This et al., Plant Mol. Biol., 20, 467–479 (1992).
Gaubier et al., Mol. Gen. Genet., 238, 409–418 (1993).
Gedis et al., Matrix, 13, 399–405 (1993).
Holsters et al., Mol Gen Genet, 163, 181–187 (1978).
Horsch R. B. et al., Science, 227, 1229–1231 (1985).
Kay et al., Science, 236, 1299–1302 (1987).
Li S-W et al., Matrix Biology 14, 593–595 (1994).
McEleroy et al., Mol Gen Genet, 231, 150–160 (1991).
Marx, Science, 216, 1305–1307 (1982).
Matsuoka K, Proc. Natl Acad Sci USA, 88, 834–838 (1991).
Morikawa et al., Biochemistry 19, 2646–2650 (1980).
Murakami et al., Plant Mol. Biol., 7, 343–355 (1986).
Ni et al., Plant J., 7, 661–676 (1995).
Parkany M, Molecular Biomaterials G. W. Hastings, P. Ducheyne eds., CRC Press, Boca Raton, 111–117 (1984).
Reina et al., Nucleic Acid Research, 18, 6426 (1990).
Schroeder M. R. et al., Plant Physiol, 101, 451–458 (1993).
Vain P. et al., Plant Cell Tissue and Organ Culture 18, 143–151 (1989).

---

What is claimed is:

1. An isolated triple coil collagen or derived protein comprising a α1 chain, wherein said α1 chain is prepared by:
   a) transforming a plant cell with a host cell transformed by a vector comprising a recombinant nucleotide sequence that:
      i) encodes said chain, but does not encode the N-propeptide; and
      ii) comprises elements which enable said plant cell to produce said chain encoded by said nucleotide sequence; and
   b) obtaining transformed plants from said transformed plant cells;
   c) collecting said triple coil collagen or derived protein.

2. An isolated triple coil collagen or derived protein according to claim 1, wherein said host cell is a bacterium.

3. An isolated triple coil collagen or derived protein according to claim 2, wherein said bacterium is *Agrobacterium tumefaciens*.

4. An isolated triple coil collagen or derived protein according to claim 1, wherein said vector is a plasmid vector.

5. An isolated triple coil collagen or derived protein according to claim 1, wherein said nucleotide sequence is inserted at a site which is non-essential for replication of said vector.

6. An isolated triple coil collagen or derived protein according to claim 1, wherein said elements are recognized by transcriptional machinery of said plant cell.

7. An isolated triple coil collagen or derived protein according to claim 1, wherein said elements comprises a promoter and a transcription terminator.

8. An isolated triple coil collagen or derived protein according to claim 1, wherein said recombinant nucleotide sequence is incorporated into the genome of said plant cell.

9. An isolated triple coil collagen or derived protein according to claim 1, wherein collecting said triple coil collagen or derived protein comprises extraction.

10. An isolated triple coil collagen or derived protein according to claims 9, further comprising purifying the triple coil collagen or derived protein.

* * * * *

UNITED STATES PATENT AND TRADEMARK OFFICE
CERTIFICATE OF CORRECTION

PATENT NO. : 6,617,431 B1
DATED : January 13, 2004
INVENTOR(S) : Gruber et al.

It is certified that error appears in the above-identified patent and that said Letters Patent is hereby corrected as shown below:

Column 1,
Line 35, now reads "two types (α1 and a2)…", and should read
-- two types (α1 and α2) … --

Column 10,
Line 64, now reads "(50jig/ml), and the culture…", and should read
-- (50 μg/ml), and the culture … --

Column 11,
Line 1, now reads "b/Preparation of Niro-cellulose Replicas: …", and should read
-- b/ Preparation of Nitro-cellulose Replicas … --

Column 14,
Line 15, now reads "encoding the human proc (I) chain.", and should read
-- encoding the human proα (I) chain. --

Column 24,
Line 34, now reads "of 20 f for 2 hours at 37º C.", and should read
-- of 20 μl for 2 hours at 37º C. --

Column 28,
Line 19, now reads "phenol ad centrifuged …", and should read
-- phenol and centrifuged … --
Line 22, now reads "REPARATION II1.", and should read
-- PREPARATION II1 --
Line 27, now reads "(DraIII/BamJI).", and should read -- (DraIII/BamHI). --

Column 30,
Lines 60-61, now reads "TE buffer (1I nM Tris, 1 mM EDTA, pH8)…", and should read -- TE buffer (10 mM Tris, 1 mM EDTA, pH 8) … --

Column 33,
Line 25, now reads "to clone the SacI/HneI fragment…", and should read
-- to clone the SacII/NheI fragment … --

Column 40,
Line 49, now reads "digestion, 4 III stop buffer…", and should read -- digestion, 4 μl stop buffer … --
Line 60, now reads "cut under WV, deposited…", and should read
-- cut under UV, deposited … --

UNITED STATES PATENT AND TRADEMARK OFFICE
CERTIFICATE OF CORRECTION

PATENT NO. : 6,617,431 B1
DATED : January 13, 2004
INVENTOR(S) : Gruber et al.

It is certified that error appears in the above-identified patent and that said Letters Patent is hereby corrected as shown below:

<u>Column 41,</u>
Line 31, now reads "digestion by the NehI restriction…" and should read
-- digestion by the Nhel restriction … --

<u>Column 42,</u>
Line 1, now reads "Cloning of Fragments (HindIII/HindIII) of Bonstructs…",
and should read -- Cloning of Fragments (HindIII/HindIII) of Constructs… --
Line 38, now reads "ADEFH159 or BCDEFGphe159…", and should read
-- ADEFHphe159 or BCDEFGphe159 … --

<u>Column 43,</u>
Line 22, now reads "tetracycline (40 pg/ml),…", and should read
-- tetracysline (40 µg/ml), … --

<u>Column 44,</u>
Line 59, now reads "region of 80 µE m$^{-2}$ …", and should read
-- region of 80 µE m$^{-2}$ S$^{-1}$. … --

Signed and Sealed this

Second Day of March, 2004

JON W. DUDAS
*Acting Director of the United States Patent and Trademark Office*

SEQUENCE LISTING

<160> NUMBER OF SEQ ID NOS: 22

<210> SEQ ID NO 1
<211> LENGTH: 4
<212> TYPE: PRT
<213> ORGANISM: Unknown
<220> FEATURE:
<223> OTHER INFORMATION: peptide localization sequence

<400> SEQUENCE: 1

Lys Asp Glu Leu
1

<210> SEQ ID NO 2
<211> LENGTH: 6
<212> TYPE: PRT

```
<213> ORGANISM: Unknown
<220> FEATURE:
<223> OTHER INFORMATION: peptide localization sequence

<400> SEQUENCE: 2

Ser Glu Lys Asp Glu Leu
1               5

<210> SEQ ID NO 3
<211> LENGTH: 4
<212> TYPE: PRT
<213> ORGANISM: Unknown
<220> FEATURE:
<223> OTHER INFORMATION: peptide localization sequence

<400> SEQUENCE: 3

His Asp Glu Leu
1

<210> SEQ ID NO 4
<211> LENGTH: 17
<212> TYPE: DNA
<213> ORGANISM: Artificial Sequence
<220> FEATURE:
<223> OTHER INFORMATION: oligonucleotide BIOC5

<400> SEQUENCE: 4
ctcgggtttc cacacgt                                                17

<210> SEQ ID NO 5
<211> LENGTH: 17
<212> TYPE: DNA
<213> ORGANISM: Artificial Sequence
<220> FEATURE:
<223> OTHER INFORMATION: oligonucleotide BIOC7

<400> SEQUENCE: 5
gcaagacagt gattgaa                                                17

<210> SEQ ID NO 6
<211> LENGTH: 19
<212> TYPE: DNA
<213> ORGANISM: Artificial Sequence
<220> FEATURE:
<223> OTHER INFORMATION: T7 gene primer

<400> SEQUENCE: 6
tgaggttgta gaagttccg                                              19

<210> SEQ ID NO 7
<211> LENGTH: 19
<212> TYPE: DNA
<213> ORGANISM: Artificial Sequence
<220> FEATURE:
<223> OTHER INFORMATION: T7 terminator primer

<400> SEQUENCE: 7
gctagttatt gctcagcgg                                              19

<210> SEQ ID NO 8
<211> LENGTH: 50
<212> TYPE: DNA
<213> ORGANISM: Artificial Sequence
<220> FEATURE:
<223> OTHER INFORMATION: sense oligonucleotide, BIOC85

<400> SEQUENCE: 8
```
tatccgcgga agcttagaca tgttcagctt tgtggacctc cggctcctgc            50

<210> SEQ ID NO 9
<211> LENGTH: 45
<212> TYPE: DNA
<213> ORGANISM: Artificial Sequence
<220> FEATURE:
<223> OTHER INFORMATION: antisense oligonucleotide, BIOC83

<400> SEQUENCE: 9
tattctagag ctagctttcc tccgaggcca gggggtccgg gaggt                 45

<210> SEQ ID NO 10
<211> LENGTH: 81
<212> TYPE: DNA
<213> ORGANISM: Artificial Sequence
<220> FEATURE:
<223> OTHER INFORMATION: matrix oligonucleotide, 045

<400> SEQUENCE: 10
taaatgaact tcctcaaaag tttccccttt tatgccttcc tttgttttgg ccaatacttt   60
gtagctgtta ctcatgctgc c                                            81

<210> SEQ ID NO 11
<211> LENGTH: 42
<212> TYPE: DNA
<213> ORGANISM: Artificial Sequence
<220> FEATURE:
<223> OTHER INFORMATION: sense oligonucleotide, BIO95

<400> SEQUENCE: 11
tatccgcgga agctttaaat gaacttcctc aaaagtttcc cc                     42

<210> SEQ ID NO 12
<211> LENGTH: 37
<212> TYPE: DNA
<213> ORGANISM: Artificial Sequence
<220> FEATURE:
<223> OTHER INFORMATION: antisense oligonucleotide, BIOC93

<400> SEQUENCE: 12
atgctagctc ttgagcatga gtaacagcta caaagta                           37

<210> SEQ ID NO 13
<211> LENGTH: 31
<212> TYPE: DNA
<213> ORGANISM: Artificial Sequence
<220> FEATURE:
<223> OTHER INFORMATION: sense oligonucleotide, BIOC855

<400> SEQUENCE: 13
atgctagccc aagtcgaggg ccaagacgaa g                                 31

<210> SEQ ID NO 14
<211> LENGTH: 43
<212> TYPE: DNA
<213> ORGANISM: Artificial Sequence
<220> FEATURE:
<223> OTHER INFORMATION: sense oligonucleotide, BIOC65

<400> SEQUENCE: 14
tattctagag ctagctcccc agctgtctta tggctatgat gag                    43

<210> SEQ ID NO 15

```
<211> LENGTH: 20
<212> TYPE: DNA
<213> ORGANISM: Artificial Sequence
<220> FEATURE:
<223> OTHER INFORMATION: antisense oligonucleotide, T7 gene 10 primer

<400> SEQUENCE: 15
ctgaggttgt agaagttccg                                                    20

<210> SEQ ID NO 16
<211> LENGTH: 30
<212> TYPE: DNA
<213> ORGANISM: Artificial Sequence
<220> FEATURE:
<223> OTHER INFORMATION: sense oligonucleotide, BIOC25

<400> SEQUENCE: 16
tatctgcaga tgtggccatc cagctgacct                                         30

<210> SEQ ID NO 17
<211> LENGTH: 30
<212> TYPE: DNA
<213> ORGANISM: Artificial Sequence
<220> FEATURE:
<223> OTHER INFORMATION: antisense oligonucleotide, BIOC23

<400> SEQUENCE: 17
tataagctta caggaagcag acagggccaa                                         30

<210> SEQ ID NO 18
<211> LENGTH: 51
<212> TYPE: DNA
<213> ORGANISM: Artificial Sequence
<220> FEATURE:
<223> OTHER INFORMATION: antisense oligonucleotide, BIOCKDEL

<400> SEQUENCE: 18
tataagctta tagctcatct ttcaggaagc agacagggcc aacgtcgaag c                 51

<210> SEQ ID NO 19
<211> LENGTH: 8
<212> TYPE: PRT
<213> ORGANISM: Unknown
<220> FEATURE:
<223> OTHER INFORMATION: peptide fragment from plant collagen

<400> SEQUENCE: 19

Glu Leu Ala Pro Gln Leu Ser Tyr
1               5

<210> SEQ ID NO 20
<211> LENGTH: 8
<212> TYPE: PRT
<213> ORGANISM: Unknown
<220> FEATURE:
<223> OTHER INFORMATION: peptide fragment from plant collagen

<400> SEQUENCE: 20

Ala Gln Val Glu Gly Gln Asp Glu
1               5

<210> SEQ ID NO 21
<211> LENGTH: 1464
<212> TYPE: PRT
<213> ORGANISM: Homo sapiens

<400> SEQUENCE: 21
```

```
Met Phe Ser Phe Val Asp Leu Arg Leu Leu Leu Leu Ala Ala Thr
 1               5                  10                  15

Ala Leu Leu Thr His Gly Gln Glu Gly Gln Val Glu Gly Gln Asp
            20                  25                  30

Glu Asp Ile Pro Pro Ile Thr Cys Val Gln Asn Gly Leu Arg Tyr His
            35                  40                  45

Asp Arg Asp Val Trp Lys Pro Glu Pro Cys Arg Ile Cys Val Cys Asp
        50                  55                  60

Asn Gly Lys Val Leu Cys Asp Asp Val Ile Cys Asp Glu Thr Lys Asn
 65                  70                  75                  80

Cys Pro Gly Ala Glu Val Pro Glu Gly Glu Cys Cys Pro Val Cys Pro
                    85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
                115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Lys Leu Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
                195                 200                 205

Gly Glu Pro Gly Ala Ser Gly Pro Met Gly Pro Arg Gly Pro Pro Gly
        210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
        260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
        290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
                340                 345                 350

Gly Glu Ala Gly Pro Gln Gly Pro Arg Gly Ser Glu Gly Pro Gln Gly
                355                 360                 365

Val Arg Gly Glu Pro Gly Pro Pro Gly Pro Ala Gly Ala Ala Gly Pro
        370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415
```

```
Pro Ser Gly Pro Gln Gly Pro Gly Pro Pro Gly Lys Gly Asn
            420                 425                 430

Ser Gly Glu Pro Gly Ala Pro Gly Ser Lys Gly Asp Thr Gly Ala Lys
            435                 440                 445

Gly Glu Pro Gly Pro Val Gly Val Gln Gly Pro Pro Gly Pro Ala Gly
            450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
                500                 505                 510

Ser Pro Gly Pro Ala Gly Pro Lys Gly Ser Pro Gly Glu Ala Gly Arg
            515                 520                 525

Pro Gly Glu Ala Gly Leu Pro Gly Ala Lys Gly Leu Thr Gly Ser Pro
            530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
                580                 585                 590

Gly Lys Ala Gly Glu Arg Gly Val Pro Gly Pro Pro Gly Ala Val Gly
            595                 600                 605

Pro Ala Gly Lys Asp Gly Glu Ala Gly Ala Gln Gly Pro Pro Gly Pro
            610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
                660                 665                 670

Ser Gly Ala Arg Gly Glu Arg Gly Phe Pro Gly Glu Arg Gly Val Gln
            675                 680                 685

Gly Pro Pro Gly Pro Ala Gly Pro Arg Gly Ala Asn Gly Ala Pro Gly
            690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
                740                 745                 750

Ala Asp Gly Ser Pro Gly Lys Asp Gly Val Arg Gly Leu Thr Gly Pro
            755                 760                 765

Ile Gly Pro Pro Gly Pro Ala Gly Ala Pro Gly Asp Lys Gly Glu Ser
            770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
                820                 825                 830

Gly Ala Lys Gly Asp Ala Gly Pro Pro Gly Pro Ala Gly Pro Ala Gly
```

-continued

Pro Pro Gly Pro Ile Gly Asn Val Gly Ala Pro Gly Ala Lys Gly Ala
850             855                 860

Arg Gly Ser Ala Gly Pro Pro Gly Ala Thr Gly Phe Pro Gly Ala Ala
865             870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Lys Gly Pro Arg Gly Glu
            900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
                980                 985                 990

Glu Arg Gly Pro Pro Gly Pro Met Gly Pro Pro Gly Leu Ala Gly Pro
                995                 1000                1005

Pro Gly Glu Ser Gly Arg Glu Gly Ala Pro Gly Ala Glu Gly Ser
            1010                1015                1020

Pro Gly Arg Asp Gly Ser Pro Gly Ala Lys Gly Asp Arg Gly Glu
            1025                1030                1035

Thr Gly Pro Ala Gly Pro Pro Gly Ala Pro Gly Ala Pro Gly Ala
            1040                1045                1050

Pro Gly Pro Val Gly Pro Ala Gly Lys Ser Gly Asp Arg Gly Glu
            1055                1060                1065

Thr Gly Pro Ala Gly Pro Ala Gly Pro Val Gly Pro Ala Gly Ala
            1070                1075                1080

Arg Gly Pro Ala Gly Pro Gln Gly Pro Arg Gly Asp Lys Gly Glu
            1085                1090                1095

Thr Gly Glu Gln Gly Asp Arg Gly Ile Lys Gly His Arg Gly Phe
            1100                1105                1110

Ser Gly Leu Gln Gly Pro Pro Gly Pro Pro Gly Ser Pro Gly Glu
            1115                1120                1125

Gln Gly Pro Ser Gly Ala Ser Gly Pro Ala Gly Pro Arg Gly Pro
            1130                1135                1140

Pro Gly Ser Ala Gly Ala Pro Gly Lys Asp Gly Leu Asn Gly Leu
            1145                1150                1155

Pro Gly Pro Ile Gly Pro Pro Gly Pro Arg Gly Arg Thr Gly Asp
            1160                1165                1170

Ala Gly Pro Val Gly Pro Pro Gly Pro Pro Gly Pro Pro Gly Pro
            1175                1180                1185

Pro Gly Pro Pro Ser Ala Gly Phe Asp Phe Ser Phe Leu Pro Gln
            1190                1195                1200

Pro Pro Gln Glu Lys Ala His Asp Gly Gly Arg Tyr Tyr Arg Ala
            1205                1210                1215

Asp Asp Ala Asn Val Val Arg Asp Arg Asp Leu Glu Val Asp Thr
            1220                1225                1230

Thr Leu Lys Ser Leu Ser Gln Gln Ile Glu Asn Ile Arg Ser Pro
            1235                1240                1245

-continued

| | | | | | | | | | |
|---|---|---|---|---|---|---|---|---|---|
| Glu | Gly | Ser | Arg | Lys | Asn | Pro | Ala | Arg | Thr | Cys | Arg | Asp | Leu | Lys |
| | 1250 | | | | 1255 | | | | 1260 | | | | | |

Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
    1265                1270                1275

Asn Gln Gly Cys Asn Leu Asp Ala Ile Lys Val Phe Cys Asn Met
    1280                1285                1290

Glu Thr Gly Glu Thr Cys Val Tyr Pro Thr Gln Pro Ser Val Ala
    1295                1300                1305

Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
    1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
    1370                1375                1380

Leu Lys Lys Ala Leu Leu Leu Lys Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 22
<211> LENGTH: 4409
<212> TYPE: DNA
<213> ORGANISM: Homo sapiens

<400> SEQUENCE: 22

```
aagcttagac atgttcagct ttgtggacct ccggctcctg ctcctcttag cggccaccgc    60
cctcctgacg cacggccaag aggaaggcca agtcgagggc caagacgaag acatcccacc   120
aatcacctgc gtacagaacg gcctcaggta ccatgaccga cgtgtggaa aacccgagcc   180
ctgccggatc tgcgtctgcg acaacggcaa ggtgttgtgc gatgacgtga tctgtgacga   240
gaccaagaac tgccccggcg ccgaagtccc gagggcgag tgctgtcccg tctgccccga   300
cggctcagag tcacccaccg accaagaaac caccggcgtc gagggaccca agggagacac   360
tggcccccga ggcccaaggg gacccgcagg ccccccctggc cgagatggca tcctggaca   420
gcctggactt cccggaccc cggacccc cggacctccc ggaccccctg gcctcggagg   480
aaagctagct ccccagctgt cttatggcta tgatgagaaa tcaaccggag gaatttccgt   540
gcctggcccc atgggtccct ctggtcctcg tggtctccct ggccccctg gtgcacctgg   600
tccccaaggc ttccaaggtc ccctggtga gcctggcgag cctggagctt caggtcccat   660
gggtccccga ggtccccccag gtcccctgg aaagaatgga gatgatgggg aagctggaaa   720
acctggtcgt cctggtgagc gtgggcctcc tgggcctcag ggtgctcgag gattgcccgg   780
```

-continued

```
aacagctggc ctccctggaa tgaagggaca cagaggtttc agtggtttgg atggtgccaa      840
gggagatgct ggtcctgctg gtcctaaggg tgagcctggc agccctggtg aaaatggagc      900
tcctggtcag atgggccccc gtggcctgcc tggtgagaga ggtcgccctg gagcccctgg      960
ccctgctggt gctcgtggaa atgatggtgc tactggtgct gccgggcccc ctggtcccac     1020
cggccccgct ggtcctcctg gcttccctgg tgctgttggt gctaagggtg aagctggtcc     1080
ccaagggccc cgaggctctg aaggtcccca gggtgtgcgt ggtgagcctg gtcccctgg      1140 ccctgctggt gctgctggcc ctgctggaaa ccctggtgct gatggacagc tggtgctaa      1200 aggtgccaat ggtgctcctg gtattgctgg tgctcctggc ttccctggtg cccgaggccc     1260
ctctggaccc cagggccccg gcggccctcc tggtcccaag ggtaacagcg gtgaacctgg     1320
tgctcctggc agcaaaggag acactggtgc taagggagag cctggccctg ttggtgttca     1380
aggaccccct ggccctgctg gagaggaagg aaagcgagga gctcgaggtg aacccggacc     1440
cactggcctg cccggacccc ctggcgagcg tggtggacct ggtagccgtg gtttccctgg     1500
cgcagatggt gttgctggtc caagggtcc cgctggtgaa cgtggttctc ctggccccgc     1560
tggccccaaa ggatctcctg gtgaagctgg tcgtcccggt gaagctggtc tgcctggtgc     1620
caagggtctg actggaagcc ctggcagccc tggtcctgat ggcaaaactg gccccctgg      1680 tcccgccggt caagatggtc gccccggacc cccaggccca cctggtgccc gtggtcaggc     1740
tggtgtgatg ggattccctg gacctaaagg tgctgctgga gagcccggca aggctggaga     1800
gcgaggtgtt cccggacccc ctggcgctgt cggtcctgct ggcaaagatg gagaggctgg     1860
agctcaggga ccccctggcc ctgctggtcc cgctggcgag agaggtgaac aaggccctgc     1920
tggctccccc ggattccagg gtctccctgg tcctgctggt cctccaggtg aagcaggcaa     1980
acctggtgaa cagggtgttc ctggagacct tggcgcccct ggcccctctg agcaagagg      2040 cgagagaggt ttccctggcg agcgtggtgt gcaaggtccc cctggtcctg ctggaccccg     2100
aggggccaac ggtgctcccg gcaacgatgg tgctaagggt gatgctggtg cccctggagc     2160
tcccggtagc cagggcgccc ctggccttca gggaatgcct ggtgaacgtg gtgcagctgg     2220
tcttccaggg cctaagggtg acagaggtga tgctggtccc aaaggtgctg atggctctcc     2280
tggcaaagat ggcgtccgtg gtctgaccgg ccccattggt cctcctggcc ctgctggtgc     2340
ccctggtgac aagggtgaaa gtggtcccag cggccctgct ggtcccactg agctcgtgg      2400 tgcccccgga gaccgtggtg agcctggtcc ccccggcccc gctggctttg ctggcccccc     2460
tggtgctgac ggccaacctg gtgctaaagg cgaacctggt gatgctggtg ccaaaggcga     2520
tgctggtccc cctgggcctg ccggacccgc tggacccccc ggcccccattg gtaatgttgg     2580 tgctcctgga gccaaaggtg ctcgcggcag cgctggtccc cctggtgcta ctggtttccc     2640
tggtgctgct ggccgagtcg gtcctcctgg cccctctgga aatgctggac cccctggccc     2700
tcctggtcct gctggcaaag aaggcggcaa aggtccccgt ggtgagactg gccctgctgg     2760
acgtcctggt gaagttggtc ccctggtcc cctggcctg ctggcgagaa aggatcccc       2820 tggtgctgat ggtcctgctg gtgctcctgg tactcccggg cctcaaggta ttgctggaca     2880
gcgtggtgtg gtcggcctgc ctggtcagag aggagagaga ggcttccctg gtcttcctgg     2940 ccctctggt gaacctggca acaaggtcc ctctggagca agtggtgaac gtggtccccc       3000 cggtccccatg ggcccccctg gattggctgg acccctggt gaatctggac gtgaggggc      3060 tcctggtgcc gaaggttccc ctggacgaga cggttctcct ggcgccaagg gtgaccgtgg     3120
```

-continued

```
tgagaccggc cccgctggac ccctggtgc tcctggtgct cctggtgccc ctggcccgt    3180 tggccctgct ggcaagagtg gtgatcgtgg tgagactggt cctgctggtc ccgccggtcc   3240
cgtcggcccc gctggcgccc gtggcccgc cggaccccaa ggccccgtg gtgacaaggg    3300 tgagacaggc gaacagggcg acagaggcat aaagggtcac cgtggcttct ctggcctcca   3360
gggtccccct ggccctcctg gctctcctgg tgaacaaggt ccctctggag cctctggtcc   3420
tgctggtccc cgaggtcccc ctggctctgc tggtgctcct ggcaaagatg gactcaacgg   3480
tctccctggc cccattgggc ccctggtcc tcgcggtcgc actggtgatg ctggtcctgt    3540 tggtccccc ggccctcctg gacctcctgg tcccctggt cctcccagcg ctggtttcga    3600
cttcagcttc ctgccccagc cacctcaaga gaaggctcac gatggtggcc gctactaccg   3660
ggctgatgat gccaatgtgg ttcgtgaccg tgacctcgag gtggacacca ccctcaagag   3720
cctgagccag cagatcgaga acatccggag cccagaggga agccgcaaga accccgcccg   3780
cacctgccgt gacctcaaga tgtgccactc tgactggaag agtggagagt actggattga   3840
ccccaaccaa ggctgcaacc tggatgccat caaagtcttc tgcaacatgg agactggtga   3900
gacctgcgtg taccccactc agcccagtgt ggcccagaag aactggtaca tcagcaagaa   3960
ccccaaggac aagaggcatg tctggttcgg cgagagcatg accgatggat tccagttcga   4020
gtatggcggc cagggctccg accctgccga tgtggccatc cagctgacct tcctgcgcct   4080
gatgtccacc gaggcctccc agaacatcac ctaccactgc aagaacagcg tggcctacat   4140
ggaccagcag actggcaacc tcaagaaggc cctgctcctc aagggctcca acgagatcga   4200
gatccgcgcc gagggcaaca gccgcttcac ctacagcgtc actgtcgatg gctgcacgag   4260
tcacaccgga gcctggggca agacagtgat tgaatacaaa accaccaaga cctcccgcct   4320
gcccatcatc gatgtggccc ccttggacgt tggtgcccca gaccaggaat tcggcttcga   4380
cgttggccct gtctgcttcc tgtaagctt                                    4409
```